United States Patent
Getts et al.

(10) Patent No.: US 11,215,615 B2
(45) Date of Patent: Jan. 4, 2022

(54) PEPTIDES, REAGENTS AND METHODS FOR DETECTING FOOD ALLERGY

(71) Applicants: Genisphere, LLC, Hatfield, PA (US); ICAHN School of Medicine at Mount Sinai, New York, NY (US)

(72) Inventors: Robert C. Getts, Collegeville, PA (US); James Kadushin, Gilbertsville, PA (US); Hugh A. Sampson, Greenwich, CT (US); Luda Bardina, Red Hook, NY (US); Galina Grishina, Tarrytown, NY (US); Gustavo Gimenez, New York, NY (US); Jing Lin, Guangzhou (CN)

(73) Assignees: AllerGenis LLC, Hatfield, PA (US); ICAHN School of Medicine at Mount Sinai, New York, NY (US)

( * ) Notice: Subject to any disclaimer, the term of this patent is extended or adjusted under 35 U.S.C. 154(b) by 236 days.

(21) Appl. No.: 15/129,979

(22) PCT Filed: Mar. 20, 2015

(86) PCT No.: PCT/US2015/021715
§ 371 (c)(1),
(2) Date: Sep. 28, 2016

(87) PCT Pub. No.: WO2015/153151
PCT Pub. Date: Oct. 8, 2015

(65) Prior Publication Data
US 2017/0219578 A1    Aug. 3, 2017

Related U.S. Application Data

(60) Provisional application No. 61/974,675, filed on Apr. 3, 2014.

(51) Int. Cl.
*G01N 33/564* (2006.01)
*G01N 33/68* (2006.01)

(52) U.S. Cl.
CPC ....... *G01N 33/564* (2013.01); *G01N 33/6854* (2013.01); *G01N 2800/24* (2013.01)

(58) Field of Classification Search
None
See application file for complete search history.

(56) References Cited

U.S. PATENT DOCUMENTS

| 8,802,375 B2 * | 8/2014 | Sampson | G01N 33/6854 435/7.1 |
|---|---|---|---|
| 2008/0075725 A1 | 3/2008 | O'Hehir et al. | |
| 2011/0071043 A1 | 3/2011 | Sampson | |
| 2013/0243814 A1 | 8/2013 | Caplan et al. | |
| 2014/0080730 A1 | 3/2014 | Dreskin et al. | |
| 2015/0168389 A1 | 6/2015 | Sampson et al. | |
| 2016/0263212 A1 | 9/2016 | Friedman et al. | |
| 2017/0219578 A1 | 8/2017 | Getts et al. | |
| 2019/0359660 A1 | 11/2019 | Getts et al. | |

FOREIGN PATENT DOCUMENTS

| EP | 3054300 | | 8/2016 |
|---|---|---|---|
| JP | 2011095132 | | 5/2011 |
| WO | 9939211 | A1 | 8/1999 |
| WO | WO 2005/081628 | * | 9/2005 |
| WO | 2005100995 | A2 | 10/2005 |
| WO | 2008111281 | | 9/2008 |
| WO | 2010052939 | | 5/2010 |
| WO | 2010110454 | | 9/2010 |
| WO | 2015015043 | A1 | 2/2015 |
| WO | 2019226600 | | 11/2019 |

OTHER PUBLICATIONS

Matsumoto et al., "Peptide array-based analysis of the specific IgE and IgG4 in cow's milk allergens and its use in allergy evaluation", Peptides, 2009, vol. 30, No. 10, p. 1840-1847.
Lin et al., "Development of a novel peptide microarray for large-scale epitope mapping of food allergens", Journal of Allergy and Clinical Immunology, 2009, vol. 124, No. 2, p. 315-322.
Wang et al., "Correlation of IgE/IgG4 milk epitopes and affinity of milk-specific IgE antibodies with different phenotypes of clinical milk allergy", Journal of Allergy and Clinical Immunology, 2010, vol. 125, No. 3, p. 695-702.
"International Preliminary Reporton Patentability" in PCT/US2015/021715, dated Oct. 4, 2016, 10 pages.
"International Search Report and Written Opinion in PCT/US2015/021715", dated Jun. 29, 2015, 15 pages.
Lin, et al., "Development of a novel peptide microarray for large-scale epitope mapping of food allergens", Journal of Allergy and Clinical Immunology, 2009, vol. 124, No. 2, pp. 315-322, e3.
Matsumoto, et al., "Peptide array-based analysis of the specific IgE and IgG4 in cow's milk allergens and its use in allergy evaluation", Peptides, 2009, vol. 30, No. 10, pp. 1840-1847.
Pomponi, et al., "Allergen micro-bead array for IgE detection: a feasibility study using allergenic molecules tested on a flexible multiplex flow cytometric immunoassay", PloS One, 2012, vol. 7, Issue No. 4, Article No. e35697 (internal pp. 1-16).
Wang, et al., "Correlation of IgE/IgG4 milk epitopes and affinity of milk-specific IgE antibodies with different phenotypes of clinical milk allergy", Journal of Allergy and Clinical Immunology, 2010, vol. 125, No. 3, pp. 695-702, e6.

(Continued)

*Primary Examiner* — Nora M Rooney
(74) *Attorney, Agent, or Firm* — Stradley Ronon Stevens & Young, LLP

(57) ABSTRACT

Provided are peptide biomarkers for diagnosis of allergy, monitoring development of clinical tolerance in an allergic individual, and predicting whether an allergic subject is likely to develop clinical or natural tolerance over time. The invention also relates to diagnostic methods and diagnostic kits employing the peptide biomarkers.

7 Claims, 3 Drawing Sheets
Specification includes a Sequence Listing.

(56) References Cited

OTHER PUBLICATIONS

Flinterman et al., "Peanut epitopes for IgE and IgG4 in peanut-sensitized children in relation to severity of peanut allergy", Journal Of Allergy And Clinical Immunology, 2008, 121(3),pp. 737-743.
Shrehfler et al., "Microarray immunoassay: Association of clinical history, in vitro IgE function, and heterogeneity of allergenic peanut epitopes", Journal Of Allergy And Clinical Immunology, 2004, 113(4), pp. 776-782.
Gregory et al., "Immunotherapy using algal-produced Ara h 1 core domain suppresses peanut allergy in mice", Plant Biotechnology Journal, 2016, 14, pp. 1541-1550.
Lin et al., "A bioinformatics approach to identify patients with symptomatic peanut allergy using peptide microarray immunoassay", J Allergy Clin Immunol, 2012, 129(5), pp. 1321-1328.
Klemans et al., "The diagnostic value of specific IgE to Ara h 2 to predict peanut allergy in children is comparable to a validated and updated diagnostic prediction model", J Allergy Clin Immunol, 2013, 131, pp. 157-163.
Lieberman et al., "The Utility of Peanut Components in the Diagnosis of IgE-Mediated Peanut Allergy Among Distinct Populations", J Allergy Clin Immunol Pract, 2013, 1, pp. 75-82.

\* cited by examiner

SEQUENCE LISTING

<160> NUMBER OF SEQ ID NOS: 683

<210> SEQ ID NO 1
<211> LENGTH: 20
<212> TYPE: PRT
<213> ORGANISM: Bos taurus

<400> SEQUENCE: 1

Lys His Gln Gly Leu Pro Gln Glu Val Leu Asn Glu Asn Leu Leu Arg
1               5                   10                  15

Phe Phe Val Ala
            20

<210> SEQ ID NO 2
<211> LENGTH: 20
<212> TYPE: PRT
<213> ORGANISM: Bos taurus

<400> SEQUENCE: 2

Val Ala Pro Phe Pro Glu Val Phe Gly Lys Glu Lys Val Asn Glu Leu
1               5                   10                  15

Ser Lys Asp Ile
            20

<210> SEQ ID NO 3
<211> LENGTH: 20
<212> TYPE: PRT
<213> ORGANISM: Bos taurus

<400> SEQUENCE: 3

Ser Ile Ser Ser Ser Glu Glu Ile Val Pro Asn Ser Val Glu Gln Lys
1               5                   10                  15

His Ile Gln Lys
            20

<210> SEQ ID NO 4
<211> LENGTH: 20
<212> TYPE: PRT
<213> ORGANISM: Bos taurus

<400> SEQUENCE: 4

Lys His Ile Gln Lys Glu Asp Val Pro Ser Glu Arg Tyr Leu Gly Tyr
1               5                   10                  15

Leu Glu Gln Leu
            20

<210> SEQ ID NO 5
<211> LENGTH: 20
<212> TYPE: PRT
<213> ORGANISM: Bos taurus

<400> SEQUENCE: 5

Ser Glu Arg Tyr Leu Gly Tyr Leu Glu Gln Leu Leu Arg Leu Lys Lys
1               5                   10                  15

Tyr Lys Val Pro
            20

<210> SEQ ID NO 6
<211> LENGTH: 20
<212> TYPE: PRT
<213> ORGANISM: Bos taurus

<400> SEQUENCE: 6

-continued

```
Lys Tyr Lys Val Pro Gln Leu Glu Ile Val Pro Asn Ser Ala Glu Glu
1               5                   10                  15

Arg Leu His Ser
            20

<210> SEQ ID NO 7
<211> LENGTH: 20
<212> TYPE: PRT
<213> ORGANISM: Bos taurus

<400> SEQUENCE: 7

Gln Gln Lys Glu Pro Met Ile Gly Val Asn Gln Glu Leu Ala Tyr Phe
1               5                   10                  15

Tyr Pro Glu Leu
            20

<210> SEQ ID NO 8
<211> LENGTH: 20
<212> TYPE: PRT
<213> ORGANISM: Bos taurus

<400> SEQUENCE: 8

Leu Gly Thr Gln Tyr Thr Asp Ala Pro Ser Phe Ser Asp Ile Pro Asn
1               5                   10                  15

Pro Ile Gly Ser
            20

<210> SEQ ID NO 9
<211> LENGTH: 20
<212> TYPE: PRT
<213> ORGANISM: Bos taurus

<400> SEQUENCE: 9

Ser Asp Ile Pro Asn Pro Ile Gly Ser Glu Asn Ser Glu Lys Thr Thr
1               5                   10                  15

Met Pro Leu Trp
            20

<210> SEQ ID NO 10
<211> LENGTH: 20
<212> TYPE: PRT
<213> ORGANISM: Bos taurus

<400> SEQUENCE: 10

Gln Glu Lys Asn Met Ala Ile Asn Pro Ser Lys Glu Asn Leu Cys Ser
1               5                   10                  15

Thr Phe Cys Lys
            20

<210> SEQ ID NO 11
<211> LENGTH: 20
<212> TYPE: PRT
<213> ORGANISM: Bos taurus

<400> SEQUENCE: 11

Ser Thr Phe Cys Lys Glu Val Val Arg Asn Ala Asn Glu Glu Glu Tyr
1               5                   10                  15

Ser Ile Gly Ser
            20

<210> SEQ ID NO 12
```

-continued

```
<211> LENGTH: 20
<212> TYPE: PRT
<213> ORGANISM: Bos taurus

<400> SEQUENCE: 12

Lys His Tyr Gln Lys Ala Leu Asn Glu Ile Asn Gln Phe Tyr Gln Lys
1               5                   10                  15

Phe Pro Gln Tyr
            20

<210> SEQ ID NO 13
<211> LENGTH: 20
<212> TYPE: PRT
<213> ORGANISM: Bos taurus

<400> SEQUENCE: 13

Gln Tyr Leu Tyr Gln Gly Pro Ile Val Leu Asn Pro Trp Asp Gln Val
1               5                   10                  15

Lys Arg Asn Ala
            20

<210> SEQ ID NO 14
<211> LENGTH: 20
<212> TYPE: PRT
<213> ORGANISM: Bos taurus

<400> SEQUENCE: 14

Lys Ile Ser Gln Arg Tyr Gln Lys Phe Ala Leu Pro Gln Tyr Leu Lys
1               5                   10                  15

Thr Val Tyr Gln
            20

<210> SEQ ID NO 15
<211> LENGTH: 20
<212> TYPE: PRT
<213> ORGANISM: Bos taurus

<400> SEQUENCE: 15

Gln Tyr Leu Lys Thr Val Tyr Gln His Gln Lys Ala Met Lys Pro Trp
1               5                   10                  15

Ile Gln Pro Lys
            20

<210> SEQ ID NO 16
<211> LENGTH: 20
<212> TYPE: PRT
<213> ORGANISM: Bos taurus

<400> SEQUENCE: 16

Arg Glu Leu Glu Glu Leu Asn Val Pro Gly Glu Ile Val Glu Ser Leu
1               5                   10                  15

Ser Ser Ser Glu
            20

<210> SEQ ID NO 17
<211> LENGTH: 20
<212> TYPE: PRT
<213> ORGANISM: Bos taurus

<400> SEQUENCE: 17

Gln Asp Lys Ile His Pro Phe Ala Gln Thr Gln Ser Leu Val Tyr Pro
1               5                   10                  15
```

```
Phe Pro Gly Pro
            20

<210> SEQ ID NO 18
<211> LENGTH: 20
<212> TYPE: PRT
<213> ORGANISM: Bos taurus

<400> SEQUENCE: 18

Phe Ala Gln Thr Gln Ser Leu Val Tyr Pro Phe Pro Gly Pro Ile Pro
1               5                   10                  15

Asn Ser Leu Pro
            20

<210> SEQ ID NO 19
<211> LENGTH: 20
<212> TYPE: PRT
<213> ORGANISM: Bos taurus

<400> SEQUENCE: 19

Asn Ile Pro Pro Leu Thr Gln Thr Pro Val Val Val Pro Pro Phe Leu
1               5                   10                  15

Gln Pro Glu Val
            20

<210> SEQ ID NO 20
<211> LENGTH: 20
<212> TYPE: PRT
<213> ORGANISM: Bos taurus

<400> SEQUENCE: 20

Lys Val Lys Glu Ala Met Ala Pro Lys His Lys Glu Met Pro Phe Pro
1               5                   10                  15

Lys Tyr Pro Val
            20

<210> SEQ ID NO 21
<211> LENGTH: 20
<212> TYPE: PRT
<213> ORGANISM: Bos taurus

<400> SEQUENCE: 21

Ser Leu Thr Leu Thr Asp Val Glu Asn Leu His Leu Pro Leu Pro Leu
1               5                   10                  15

Leu Gln Ser Trp
            20

<210> SEQ ID NO 22
<211> LENGTH: 20
<212> TYPE: PRT
<213> ORGANISM: Bos taurus

<400> SEQUENCE: 22

Phe Pro Pro Gln Ser Val Leu Ser Leu Ser Gln Ser Lys Val Leu Pro
1               5                   10                  15

Val Pro Gln Lys
            20

<210> SEQ ID NO 23
<211> LENGTH: 20
<212> TYPE: PRT
<213> ORGANISM: Bos taurus
```

```
<400> SEQUENCE: 23

Pro Val Pro Gln Lys Ala Val Pro Tyr Pro Gln Arg Asp Met Pro Ile
1               5                   10                  15

Gln Ala Phe Leu
            20

<210> SEQ ID NO 24
<211> LENGTH: 20
<212> TYPE: PRT
<213> ORGANISM: Bos taurus

<400> SEQUENCE: 24

Arg Val Tyr Val Glu Glu Leu Lys Pro Thr Pro Glu Gly Asp Leu Glu
1               5                   10                  15

Ile Leu Leu Gln
            20

<210> SEQ ID NO 25
<211> LENGTH: 20
<212> TYPE: PRT
<213> ORGANISM: Bos taurus

<400> SEQUENCE: 25

Asp Glu Cys Ala Gln Lys Lys Ile Ile Ala Glu Lys Thr Lys Ile Pro
1               5                   10                  15

Ala Val Phe Lys
            20

<210> SEQ ID NO 26
<211> LENGTH: 20
<212> TYPE: PRT
<213> ORGANISM: Bos taurus

<400> SEQUENCE: 26

Cys Leu Val Arg Thr Pro Glu Val Asp Asp Glu Ala Leu Glu Lys Phe
1               5                   10                  15

Asp Lys Ala Leu
            20

<210> SEQ ID NO 27
<211> LENGTH: 20
<212> TYPE: PRT
<213> ORGANISM: Bos taurus

<400> SEQUENCE: 27

Glu Val Asp Asp Glu Ala Leu Glu Lys Phe Asp Lys Ala Leu Lys Ala
1               5                   10                  15

Leu Pro Met His
            20

<210> SEQ ID NO 28
<211> LENGTH: 20
<212> TYPE: PRT
<213> ORGANISM: Bos taurus

<400> SEQUENCE: 28

Arg Cys Glu Lys Asp Glu Arg Phe Phe Ser Asp Lys Ile Ala Lys Tyr
1               5                   10                  15

Ile Pro Ile Gln
            20
```

```
<210> SEQ ID NO 29
<211> LENGTH: 20
<212> TYPE: PRT
<213> ORGANISM: Bos taurus

<400> SEQUENCE: 29

Lys Pro Val Ala Leu Ile Asn Asn Gln Phe Leu Pro Tyr Pro Tyr Tyr
1               5                   10                  15

Ala Lys Pro Ala
            20

<210> SEQ ID NO 30
<211> LENGTH: 20
<212> TYPE: PRT
<213> ORGANISM: Bos taurus

<400> SEQUENCE: 30

Met Ala Ile Pro Pro Lys Lys Asn Gln Asp Lys Thr Glu Ile Pro Thr
1               5                   10                  15

Ile Asn Thr Ile
            20

<210> SEQ ID NO 31
<211> LENGTH: 20
<212> TYPE: PRT
<213> ORGANISM: Bos taurus

<400> SEQUENCE: 31

Pro Thr Ser Thr Pro Thr Thr Glu Ala Val Glu Ser Thr Val Ala Thr
1               5                   10                  15

Leu Glu Asp Ser
            20

<210> SEQ ID NO 32
<211> LENGTH: 20
<212> TYPE: PRT
<213> ORGANISM: Bos taurus

<400> SEQUENCE: 32

Thr Leu Glu Asp Ser Pro Glu Val Ile Glu Ser Pro Pro Glu Ile Asn
1               5                   10                  15

Thr Val Gln Val
            20

<210> SEQ ID NO 33
<211> LENGTH: 20
<212> TYPE: PRT
<213> ORGANISM: Bos taurus

<400> SEQUENCE: 33

Tyr Ala Lys Pro Ala Ala Val Arg Ser Pro Ala Gln Ile Leu Gln Trp
1               5                   10                  15

Gln Val Leu Ser
            20

<210> SEQ ID NO 34
<211> LENGTH: 20
<212> TYPE: PRT
<213> ORGANISM: Bos taurus

<400> SEQUENCE: 34

Asn Arg Glu Gln Leu Ser Thr Ser Glu Glu Asn Ser Lys Lys Thr Val
1               5                   10                  15
```

```
Asp Met Glu Ser
        20

<210> SEQ ID NO 35
<211> LENGTH: 20
<212> TYPE: PRT
<213> ORGANISM: Bos taurus

<400> SEQUENCE: 35

Arg Ile Asn Lys Lys Ile Glu Lys Phe Gln Ser Glu Glu Gln Gln Gln
1               5                   10                  15

Thr Glu Asp Glu
        20

<210> SEQ ID NO 36
<211> LENGTH: 20
<212> TYPE: PRT
<213> ORGANISM: Bos taurus

<400> SEQUENCE: 36

Lys Val Leu Val Leu Asp Thr Asp Tyr Lys Lys Tyr Leu Leu Val Cys
1               5                   10                  15

Met Glu Asn Ser
        20

<210> SEQ ID NO 37
<211> LENGTH: 20
<212> TYPE: PRT
<213> ORGANISM: Bos taurus

<400> SEQUENCE: 37

Asn Leu Leu Arg Phe Phe Val Ala Pro Phe Pro Glu Val Phe Gly Lys
1               5                   10                  15

Glu Lys Val Asn
        20

<210> SEQ ID NO 38
<211> LENGTH: 20
<212> TYPE: PRT
<213> ORGANISM: Bos taurus

<400> SEQUENCE: 38

Pro Asn Ser Val Glu Gln Lys His Ile Gln Lys Glu Asp Val Pro Ser
1               5                   10                  15

Glu Arg Tyr Leu
        20

<210> SEQ ID NO 39
<211> LENGTH: 20
<212> TYPE: PRT
<213> ORGANISM: Bos taurus

<400> SEQUENCE: 39

Gln Lys Glu Asp Val Pro Ser Glu Arg Tyr Leu Gly Tyr Leu Glu Gln
1               5                   10                  15

Leu Leu Arg Leu
        20

<210> SEQ ID NO 40
<211> LENGTH: 20
<212> TYPE: PRT
<213> ORGANISM: Bos taurus
```

```
<400> SEQUENCE: 40

Leu Glu Ile Val Pro Asn Ser Ala Glu Arg Leu His Ser Met Lys
1               5                   10                  15

Glu Gly Ile His
            20

<210> SEQ ID NO 41
<211> LENGTH: 20
<212> TYPE: PRT
<213> ORGANISM: Bos taurus

<400> SEQUENCE: 41

Glu Arg Leu His Ser Met Lys Glu Gly Ile His Ala Gln Gln Lys Glu
1               5                   10                  15

Pro Met Ile Gly
            20

<210> SEQ ID NO 42
<211> LENGTH: 20
<212> TYPE: PRT
<213> ORGANISM: Bos taurus

<400> SEQUENCE: 42

Ile His Ala Gln Gln Lys Glu Pro Met Ile Gly Val Asn Gln Glu Leu
1               5                   10                  15

Ala Tyr Phe Tyr
            20

<210> SEQ ID NO 43
<211> LENGTH: 20
<212> TYPE: PRT
<213> ORGANISM: Bos taurus

<400> SEQUENCE: 43

Ile Gly Val Asn Gln Glu Leu Ala Tyr Phe Tyr Pro Glu Leu Phe Arg
1               5                   10                  15

Gln Phe Tyr Gln
            20

<210> SEQ ID NO 44
<211> LENGTH: 20
<212> TYPE: PRT
<213> ORGANISM: Bos taurus

<400> SEQUENCE: 44

Pro Ser Gly Ala Trp Tyr Tyr Val Pro Leu Gly Thr Gln Tyr Thr Asp
1               5                   10                  15

Ala Pro Ser Phe
            20

<210> SEQ ID NO 45
<211> LENGTH: 20
<212> TYPE: PRT
<213> ORGANISM: Bos taurus

<400> SEQUENCE: 45

Ala Trp Tyr Tyr Val Pro Leu Gly Thr Gln Tyr Thr Asp Ala Pro Ser
1               5                   10                  15

Phe Ser Asp Ile
            20
```

```
<210> SEQ ID NO 46
<211> LENGTH: 20
<212> TYPE: PRT
<213> ORGANISM: Bos taurus

<400> SEQUENCE: 46

Ser Ile Ile Ser Gln Glu Thr Tyr Lys Gln Glu Lys Asn Met Ala Ile
1               5                   10                  15

Asn Pro Ser Lys
            20

<210> SEQ ID NO 47
<211> LENGTH: 20
<212> TYPE: PRT
<213> ORGANISM: Bos taurus

<400> SEQUENCE: 47

Ile Asn Pro Ser Lys Glu Asn Leu Cys Ser Thr Phe Cys Lys Glu Val
1               5                   10                  15

Val Arg Asn Ala
            20

<210> SEQ ID NO 48
<211> LENGTH: 20
<212> TYPE: PRT
<213> ORGANISM: Bos taurus

<400> SEQUENCE: 48

Ser Ala Glu Val Ala Thr Glu Glu Val Lys Ile Thr Val Asp Asp Lys
1               5                   10                  15

His Tyr Gln Lys
            20

<210> SEQ ID NO 49
<211> LENGTH: 20
<212> TYPE: PRT
<213> ORGANISM: Bos taurus

<400> SEQUENCE: 49

Thr Ser Glu Glu Asn Ser Lys Lys Thr Val Asp Met Glu Ser Thr Glu
1               5                   10                  15

Val Phe Thr Lys
            20

<210> SEQ ID NO 50
<211> LENGTH: 20
<212> TYPE: PRT
<213> ORGANISM: Bos taurus

<400> SEQUENCE: 50

Thr Lys Leu Thr Glu Glu Glu Lys Asn Arg Leu Asn Phe Leu Lys Lys
1               5                   10                  15

Ile Ser Gln Arg
            20

<210> SEQ ID NO 51
<211> LENGTH: 20
<212> TYPE: PRT
<213> ORGANISM: Bos taurus

<400> SEQUENCE: 51

Tyr Gln His Gln Lys Ala Met Lys Pro Trp Ile Gln Pro Lys Thr Lys
```

-continued

```
1               5                   10                  15

Val Ile Pro Tyr
            20

<210> SEQ ID NO 52
<211> LENGTH: 20
<212> TYPE: PRT
<213> ORGANISM: Bos taurus

<400> SEQUENCE: 52

Pro Phe Pro Gly Pro Ile Pro Asn Ser Leu Pro Gln Asn Ile Pro Pro
1               5                   10                  15

Leu Thr Gln Thr
            20

<210> SEQ ID NO 53
<211> LENGTH: 20
<212> TYPE: PRT
<213> ORGANISM: Bos taurus

<400> SEQUENCE: 53

Gln Thr Pro Val Val Val Pro Pro Phe Leu Gln Pro Glu Val Met Gly
1               5                   10                  15

Val Ser Lys Val
            20

<210> SEQ ID NO 54
<211> LENGTH: 20
<212> TYPE: PRT
<213> ORGANISM: Bos taurus

<400> SEQUENCE: 54

Val Glu Asn Leu His Leu Pro Leu Pro Leu Leu Gln Ser Trp Met His
1               5                   10                  15

Gln Pro His Gln
            20

<210> SEQ ID NO 55
<211> LENGTH: 20
<212> TYPE: PRT
<213> ORGANISM: Bos taurus

<400> SEQUENCE: 55

Ser Trp Met His Gln Pro His Gln Pro Leu Pro Pro Thr Val Met Phe
1               5                   10                  15

Pro Pro Gln Ser
            20

<210> SEQ ID NO 56
<211> LENGTH: 20
<212> TYPE: PRT
<213> ORGANISM: Bos taurus

<400> SEQUENCE: 56

Ser Gln Ser Lys Val Leu Pro Val Pro Gln Lys Ala Val Pro Tyr Pro
1               5                   10                  15

Gln Arg Asp Met
            20

<210> SEQ ID NO 57
<211> LENGTH: 20
<212> TYPE: PRT
```

```
<213> ORGANISM: Bos taurus

<400> SEQUENCE: 57

Gly Asp Leu Glu Ile Leu Leu Gln Lys Trp Glu Asn Asp Glu Cys Ala
1               5                   10                  15

Gln Lys Lys Ile
            20

<210> SEQ ID NO 58
<211> LENGTH: 20
<212> TYPE: PRT
<213> ORGANISM: Bos taurus

<400> SEQUENCE: 58

Asp Glu Ala Leu Glu Lys Phe Asp Lys Ala Leu Lys Ala Leu Pro Met
1               5                   10                  15

His Ile Arg Leu
            20

<210> SEQ ID NO 59
<211> LENGTH: 20
<212> TYPE: PRT
<213> ORGANISM: Bos taurus

<400> SEQUENCE: 59

Arg Phe Phe Ser Asp Lys Ile Ala Lys Tyr Ile Pro Ile Gln Tyr Val
1               5                   10                  15

Leu Ser Arg Tyr
            20

<210> SEQ ID NO 60
<211> LENGTH: 20
<212> TYPE: PRT
<213> ORGANISM: Bos taurus

<400> SEQUENCE: 60

Lys Pro Val Ala Leu Ile Asn Asn Gln Phe Leu Pro Tyr Pro Tyr Tyr
1               5                   10                  15

Ala Lys Pro Ala
            20

<210> SEQ ID NO 61
<211> LENGTH: 20
<212> TYPE: PRT
<213> ORGANISM: Bos taurus

<400> SEQUENCE: 61

Tyr Ala Lys Pro Ala Ala Val Arg Ser Pro Ala Gln Ile Leu Gln Trp
1               5                   10                  15

Gln Val Leu Ser
            20

<210> SEQ ID NO 62
<211> LENGTH: 20
<212> TYPE: PRT
<213> ORGANISM: Bos taurus

<400> SEQUENCE: 62

Pro Ala Gln Ile Leu Gln Trp Gln Val Leu Ser Asn Thr Val Pro Ala
1               5                   10                  15

Lys Ser Cys Gln
            20
```

<210> SEQ ID NO 63
<211> LENGTH: 20
<212> TYPE: PRT
<213> ORGANISM: Bos taurus

<400> SEQUENCE: 63

Cys Gln Ala Gln Pro Thr Thr Met Ala Arg His Pro His Pro His Leu
1               5                   10                  15

Ser Phe Met Ala
            20

<210> SEQ ID NO 64
<211> LENGTH: 20
<212> TYPE: PRT
<213> ORGANISM: Bos taurus

<400> SEQUENCE: 64

Arg His Pro His Pro His Leu Ser Phe Met Ala Ile Pro Pro Lys Lys
1               5                   10                  15

Asn Gln Asp Lys
            20

<210> SEQ ID NO 65
<211> LENGTH: 20
<212> TYPE: PRT
<213> ORGANISM: Bos taurus

<400> SEQUENCE: 65

Thr Ile Asn Thr Ile Ala Ser Gly Glu Pro Thr Ser Thr Pro Thr Thr
1               5                   10                  15

Glu Ala Val Glu
            20

<210> SEQ ID NO 66
<211> LENGTH: 20
<212> TYPE: PRT
<213> ORGANISM: Bos taurus

<400> SEQUENCE: 66

Asp Ser Pro Glu Val Ile Glu Ser Pro Pro Glu Ile Asn Thr Val Gln
1               5                   10                  15

Val Thr Ser Thr
            20

<210> SEQ ID NO 67
<211> LENGTH: 20
<212> TYPE: PRT
<213> ORGANISM: Bos taurus

<400> SEQUENCE: 67

Pro Glu Val Ile Glu Ser Pro Pro Glu Ile Asn Thr Val Gln Val Thr
1               5                   10                  15

Ser Thr Ala Val
            20

<210> SEQ ID NO 68
<211> LENGTH: 20
<212> TYPE: PRT
<213> ORGANISM: Bos taurus

<400> SEQUENCE: 68

```
Gln Ser Leu Val Cys Gln Cys Leu Val Arg Thr Pro Glu Val Asp Asp
1               5                   10                  15

Glu Ala Leu Glu
            20
```

<210> SEQ ID NO 69
<211> LENGTH: 15
<212> TYPE: PRT
<213> ORGANISM: Arachis hypogaea

<400> SEQUENCE: 69

```
Val Leu Ala Ser Val Ser Ala Thr His Ala Lys Ser Ser Pro Tyr
1               5                   10                  15
```

<210> SEQ ID NO 70
<211> LENGTH: 15
<212> TYPE: PRT
<213> ORGANISM: Arachis hypogaea

<400> SEQUENCE: 70

```
Ser Val Ser Ala Thr His Ala Lys Ser Ser Pro Tyr Gln Lys Lys
1               5                   10                  15
```

<210> SEQ ID NO 71
<211> LENGTH: 15
<212> TYPE: PRT
<213> ORGANISM: Arachis hypogaea

<400> SEQUENCE: 71

```
Ala Thr His Ala Lys Ser Ser Pro Tyr Gln Lys Lys Thr Glu Asn
1               5                   10                  15
```

<210> SEQ ID NO 72
<211> LENGTH: 15
<212> TYPE: PRT
<213> ORGANISM: Arachis hypogaea

<400> SEQUENCE: 72

```
Thr Glu Asn Pro Cys Ala Gln Arg Cys Leu Gln Ser Cys Gln Gln
1               5                   10                  15
```

<210> SEQ ID NO 73
<211> LENGTH: 15
<212> TYPE: PRT
<213> ORGANISM: Arachis hypogaea

<400> SEQUENCE: 73

```
Pro Cys Ala Gln Arg Cys Leu Gln Ser Cys Gln Gln Glu Pro Asp
1               5                   10                  15
```

<210> SEQ ID NO 74
<211> LENGTH: 15
<212> TYPE: PRT
<213> ORGANISM: Arachis hypogaea

<400> SEQUENCE: 74

```
Leu Gln Ser Cys Gln Gln Glu Pro Asp Asp Leu Lys Gln Lys Ala
1               5                   10                  15
```

<210> SEQ ID NO 75
<211> LENGTH: 15
<212> TYPE: PRT
<213> ORGANISM: Arachis hypogaea

<400> SEQUENCE: 75

Cys Gln Gln Glu Pro Asp Asp Leu Lys Gln Lys Ala Cys Glu Ser
1               5                   10                  15

<210> SEQ ID NO 76
<211> LENGTH: 15
<212> TYPE: PRT
<213> ORGANISM: Arachis hypogaea

<400> SEQUENCE: 76

Glu Pro Asp Asp Leu Lys Gln Lys Ala Cys Glu Ser Arg Cys Thr
1               5                   10                  15

<210> SEQ ID NO 77
<211> LENGTH: 15
<212> TYPE: PRT
<213> ORGANISM: Arachis hypogaea

<400> SEQUENCE: 77

Gln Lys Ala Cys Glu Ser Arg Cys Thr Lys Leu Glu Tyr Asp Pro
1               5                   10                  15

<210> SEQ ID NO 78
<211> LENGTH: 15
<212> TYPE: PRT
<213> ORGANISM: Arachis hypogaea

<400> SEQUENCE: 78

Cys Glu Ser Arg Cys Thr Lys Leu Glu Tyr Asp Pro Arg Cys Val
1               5                   10                  15

<210> SEQ ID NO 79
<211> LENGTH: 15
<212> TYPE: PRT
<213> ORGANISM: Arachis hypogaea

<400> SEQUENCE: 79

Arg Cys Thr Lys Leu Glu Tyr Asp Pro Arg Cys Val Tyr Asp Pro
1               5                   10                  15

<210> SEQ ID NO 80
<211> LENGTH: 15
<212> TYPE: PRT
<213> ORGANISM: Arachis hypogaea

<400> SEQUENCE: 80

Lys Leu Glu Tyr Asp Pro Arg Cys Val Tyr Asp Pro Arg Gly His
1               5                   10                  15

<210> SEQ ID NO 81
<211> LENGTH: 15
<212> TYPE: PRT
<213> ORGANISM: Arachis hypogaea

<400> SEQUENCE: 81

Tyr Asp Pro Arg Cys Val Tyr Asp Pro Arg Gly His Thr Gly Thr
1               5                   10                  15

<210> SEQ ID NO 82
<211> LENGTH: 15
<212> TYPE: PRT
<213> ORGANISM: Arachis hypogaea

<400> SEQUENCE: 82

Tyr Asp Pro Arg Gly His Thr Gly Thr Thr Asn Gln Arg Ser Pro

<210> SEQ ID NO 83
<211> LENGTH: 15
<212> TYPE: PRT
<213> ORGANISM: Arachis hypogaea

<400> SEQUENCE: 83

Arg Gly His Thr Gly Thr Thr Asn Gln Arg Ser Pro Pro Gly Glu
1               5                   10                  15

<210> SEQ ID NO 84
<211> LENGTH: 15
<212> TYPE: PRT
<213> ORGANISM: Arachis hypogaea

<400> SEQUENCE: 84

Thr Asn Gln Arg Ser Pro Pro Gly Glu Arg Thr Arg Gly Arg Gln
1               5                   10                  15

<210> SEQ ID NO 85
<211> LENGTH: 15
<212> TYPE: PRT
<213> ORGANISM: Arachis hypogaea

<400> SEQUENCE: 85

Arg Ser Pro Pro Gly Glu Arg Thr Arg Gly Arg Gln Pro Gly Asp
1               5                   10                  15

<210> SEQ ID NO 86
<211> LENGTH: 15
<212> TYPE: PRT
<213> ORGANISM: Arachis hypogaea

<400> SEQUENCE: 86

Pro Gly Glu Arg Thr Arg Gly Arg Gln Pro Gly Asp Tyr Asp Asp
1               5                   10                  15

<210> SEQ ID NO 87
<211> LENGTH: 15
<212> TYPE: PRT
<213> ORGANISM: Arachis hypogaea

<400> SEQUENCE: 87

Arg Thr Arg Gly Arg Gln Pro Gly Asp Tyr Asp Asp Asp Arg Arg
1               5                   10                  15

<210> SEQ ID NO 88
<211> LENGTH: 15
<212> TYPE: PRT
<213> ORGANISM: Arachis hypogaea

<400> SEQUENCE: 88

Gly Arg Gln Pro Gly Asp Tyr Asp Asp Asp Arg Arg Gln Pro Arg
1               5                   10                  15

<210> SEQ ID NO 89
<211> LENGTH: 15
<212> TYPE: PRT
<213> ORGANISM: Arachis hypogaea

<400> SEQUENCE: 89

Pro Gly Asp Tyr Asp Asp Asp Arg Arg Gln Pro Arg Arg Glu Glu
1               5                   10                  15

<210> SEQ ID NO 90
<211> LENGTH: 15
<212> TYPE: PRT
<213> ORGANISM: Arachis hypogaea

<400> SEQUENCE: 90

Tyr Asp Asp Asp Arg Arg Gln Pro Arg Arg Glu Glu Gly Gly Arg
1               5                   10                  15

<210> SEQ ID NO 91
<211> LENGTH: 15
<212> TYPE: PRT
<213> ORGANISM: Arachis hypogaea

<400> SEQUENCE: 91

Asp Arg Arg Gln Pro Arg Arg Glu Glu Gly Gly Arg Trp Gly Pro
1               5                   10                  15

<210> SEQ ID NO 92
<211> LENGTH: 15
<212> TYPE: PRT
<213> ORGANISM: Arachis hypogaea

<400> SEQUENCE: 92

Gln Pro Arg Arg Glu Glu Gly Gly Arg Trp Gly Pro Ala Gly Pro
1               5                   10                  15

<210> SEQ ID NO 93
<211> LENGTH: 15
<212> TYPE: PRT
<213> ORGANISM: Arachis hypogaea

<400> SEQUENCE: 93

Arg Glu Glu Gly Gly Arg Trp Gly Pro Ala Gly Pro Arg Glu Arg
1               5                   10                  15

<210> SEQ ID NO 94
<211> LENGTH: 15
<212> TYPE: PRT
<213> ORGANISM: Arachis hypogaea

<400> SEQUENCE: 94

Gly Gly Arg Trp Gly Pro Ala Gly Pro Arg Glu Arg Glu Arg Glu
1               5                   10                  15

<210> SEQ ID NO 95
<211> LENGTH: 15
<212> TYPE: PRT
<213> ORGANISM: Arachis hypogaea

<400> SEQUENCE: 95

Trp Gly Pro Ala Gly Pro Arg Glu Arg Glu Arg Glu Glu Asp Trp
1               5                   10                  15

<210> SEQ ID NO 96
<211> LENGTH: 15
<212> TYPE: PRT
<213> ORGANISM: Arachis hypogaea

<400> SEQUENCE: 96

Ala Gly Pro Arg Glu Arg Glu Arg Glu Glu Asp Trp Arg Gln Pro
1               5                   10                  15

<210> SEQ ID NO 97

```
<211> LENGTH: 15
<212> TYPE: PRT
<213> ORGANISM: Arachis hypogaea

<400> SEQUENCE: 97

Arg Glu Arg Glu Arg Glu Glu Asp Trp Arg Gln Pro Arg Glu Asp
1               5                   10                  15

<210> SEQ ID NO 98
<211> LENGTH: 15
<212> TYPE: PRT
<213> ORGANISM: Arachis hypogaea

<400> SEQUENCE: 98

Glu Arg Glu Glu Asp Trp Arg Gln Pro Arg Glu Asp Trp Arg Arg
1               5                   10                  15

<210> SEQ ID NO 99
<211> LENGTH: 15
<212> TYPE: PRT
<213> ORGANISM: Arachis hypogaea

<400> SEQUENCE: 99

Glu Asp Trp Arg Gln Pro Arg Glu Asp Trp Arg Arg Pro Ser His
1               5                   10                  15

<210> SEQ ID NO 100
<211> LENGTH: 15
<212> TYPE: PRT
<213> ORGANISM: Arachis hypogaea

<400> SEQUENCE: 100

Arg Gln Pro Arg Glu Asp Trp Arg Arg Pro Ser His Gln Gln Pro
1               5                   10                  15

<210> SEQ ID NO 101
<211> LENGTH: 15
<212> TYPE: PRT
<213> ORGANISM: Arachis hypogaea

<400> SEQUENCE: 101

Arg Glu Asp Trp Arg Arg Pro Ser His Gln Gln Pro Arg Lys Ile
1               5                   10                  15

<210> SEQ ID NO 102
<211> LENGTH: 15
<212> TYPE: PRT
<213> ORGANISM: Arachis hypogaea

<400> SEQUENCE: 102

Trp Arg Arg Pro Ser His Gln Gln Pro Arg Lys Ile Arg Pro Glu
1               5                   10                  15

<210> SEQ ID NO 103
<211> LENGTH: 15
<212> TYPE: PRT
<213> ORGANISM: Arachis hypogaea

<400> SEQUENCE: 103

Pro Ser His Gln Gln Pro Arg Lys Ile Arg Pro Glu Gly Arg Glu
1               5                   10                  15

<210> SEQ ID NO 104
<211> LENGTH: 15
<212> TYPE: PRT
```

<213> ORGANISM: Arachis hypogaea

<400> SEQUENCE: 104

Gln Gln Pro Arg Lys Ile Arg Pro Glu Gly Arg Glu Gly Glu Gln
1               5                   10                  15

<210> SEQ ID NO 105
<211> LENGTH: 15
<212> TYPE: PRT
<213> ORGANISM: Arachis hypogaea

<400> SEQUENCE: 105

Arg Lys Ile Arg Pro Glu Gly Arg Glu Gly Glu Gln Glu Trp Gly
1               5                   10                  15

<210> SEQ ID NO 106
<211> LENGTH: 15
<212> TYPE: PRT
<213> ORGANISM: Arachis hypogaea

<400> SEQUENCE: 106

Arg Pro Glu Gly Arg Glu Gly Glu Gln Glu Trp Gly Thr Pro Gly
1               5                   10                  15

<210> SEQ ID NO 107
<211> LENGTH: 15
<212> TYPE: PRT
<213> ORGANISM: Arachis hypogaea

<400> SEQUENCE: 107

Gly Arg Glu Gly Glu Gln Glu Trp Gly Thr Pro Gly Ser His Val
1               5                   10                  15

<210> SEQ ID NO 108
<211> LENGTH: 15
<212> TYPE: PRT
<213> ORGANISM: Arachis hypogaea

<400> SEQUENCE: 108

Gly Glu Gln Glu Trp Gly Thr Pro Gly Ser His Val Arg Glu Glu
1               5                   10                  15

<210> SEQ ID NO 109
<211> LENGTH: 15
<212> TYPE: PRT
<213> ORGANISM: Arachis hypogaea

<400> SEQUENCE: 109

Glu Trp Gly Thr Pro Gly Ser His Val Arg Glu Glu Thr Ser Arg
1               5                   10                  15

<210> SEQ ID NO 110
<211> LENGTH: 15
<212> TYPE: PRT
<213> ORGANISM: Arachis hypogaea

<400> SEQUENCE: 110

Arg Glu Glu Thr Ser Arg Asn Asn Pro Phe Tyr Phe Pro Ser Arg
1               5                   10                  15

<210> SEQ ID NO 111
<211> LENGTH: 15
<212> TYPE: PRT
<213> ORGANISM: Arachis hypogaea

<400> SEQUENCE: 111

Thr Ser Arg Asn Asn Pro Phe Tyr Phe Pro Ser Arg Arg Phe Ser
1               5                   10                  15

<210> SEQ ID NO 112
<211> LENGTH: 15
<212> TYPE: PRT
<213> ORGANISM: Arachis hypogaea

<400> SEQUENCE: 112

Asn Asn Pro Phe Tyr Phe Pro Ser Arg Arg Phe Ser Thr Arg Tyr
1               5                   10                  15

<210> SEQ ID NO 113
<211> LENGTH: 15
<212> TYPE: PRT
<213> ORGANISM: Arachis hypogaea

<400> SEQUENCE: 113

Arg Ile Pro Ser Gly Phe Ile Ser Tyr Ile Leu Asn Arg His Asp
1               5                   10                  15

<210> SEQ ID NO 114
<211> LENGTH: 15
<212> TYPE: PRT
<213> ORGANISM: Arachis hypogaea

<400> SEQUENCE: 114

Ser Gly Phe Ile Ser Tyr Ile Leu Asn Arg His Asp Asn Gln Asn
1               5                   10                  15

<210> SEQ ID NO 115
<211> LENGTH: 15
<212> TYPE: PRT
<213> ORGANISM: Arachis hypogaea

<400> SEQUENCE: 115

Asn Gln Asn Leu Arg Val Ala Lys Ile Ser Met Pro Val Asn Thr
1               5                   10                  15

<210> SEQ ID NO 116
<211> LENGTH: 15
<212> TYPE: PRT
<213> ORGANISM: Arachis hypogaea

<400> SEQUENCE: 116

Leu Arg Val Ala Lys Ile Ser Met Pro Val Asn Thr Pro Gly Gln
1               5                   10                  15

<210> SEQ ID NO 117
<211> LENGTH: 15
<212> TYPE: PRT
<213> ORGANISM: Arachis hypogaea

<400> SEQUENCE: 117

Ala Lys Ile Ser Met Pro Val Asn Thr Pro Gly Gln Phe Glu Asp
1               5                   10                  15

<210> SEQ ID NO 118
<211> LENGTH: 15
<212> TYPE: PRT
<213> ORGANISM: Arachis hypogaea

<400> SEQUENCE: 118

Ser Met Pro Val Asn Thr Pro Gly Gln Phe Glu Asp Phe Phe Pro
1               5                   10                  15

<210> SEQ ID NO 119
<211> LENGTH: 15
<212> TYPE: PRT
<213> ORGANISM: Arachis hypogaea

<400> SEQUENCE: 119

Val Asn Thr Pro Gly Gln Phe Glu Asp Phe Phe Pro Ala Ser Ser
1               5                   10                  15

<210> SEQ ID NO 120
<211> LENGTH: 15
<212> TYPE: PRT
<213> ORGANISM: Arachis hypogaea

<400> SEQUENCE: 120

Pro Gly Gln Phe Glu Asp Phe Phe Pro Ala Ser Ser Arg Asp Gln
1               5                   10                  15

<210> SEQ ID NO 121
<211> LENGTH: 15
<212> TYPE: PRT
<213> ORGANISM: Arachis hypogaea

<400> SEQUENCE: 121

Phe Glu Asp Phe Phe Pro Ala Ser Ser Arg Asp Gln Ser Ser Tyr
1               5                   10                  15

<210> SEQ ID NO 122
<211> LENGTH: 15
<212> TYPE: PRT
<213> ORGANISM: Arachis hypogaea

<400> SEQUENCE: 122

Ala Ser Ser Arg Asp Gln Ser Ser Tyr Leu Gln Gly Phe Ser Arg
1               5                   10                  15

<210> SEQ ID NO 123
<211> LENGTH: 15
<212> TYPE: PRT
<213> ORGANISM: Arachis hypogaea

<400> SEQUENCE: 123

Arg Asp Gln Ser Ser Tyr Leu Gln Gly Phe Ser Arg Asn Thr Leu
1               5                   10                  15

<210> SEQ ID NO 124
<211> LENGTH: 15
<212> TYPE: PRT
<213> ORGANISM: Arachis hypogaea

<400> SEQUENCE: 124

Ser Ser Tyr Leu Gln Gly Phe Ser Arg Asn Thr Leu Glu Ala Ala
1               5                   10                  15

<210> SEQ ID NO 125
<211> LENGTH: 15
<212> TYPE: PRT
<213> ORGANISM: Arachis hypogaea

<400> SEQUENCE: 125

Leu Gln Gly Phe Ser Arg Asn Thr Leu Glu Ala Ala Phe Asn Ala
1               5                   10                  15

<210> SEQ ID NO 126
<211> LENGTH: 15
<212> TYPE: PRT
<213> ORGANISM: Arachis hypogaea

<400> SEQUENCE: 126

Arg Val Leu Leu Glu Glu Asn Ala Gly Gly Glu Gln Glu Glu Arg
1               5                   10                  15

<210> SEQ ID NO 127
<211> LENGTH: 15
<212> TYPE: PRT
<213> ORGANISM: Arachis hypogaea

<400> SEQUENCE: 127

Leu Glu Glu Asn Ala Gly Gly Glu Gln Glu Glu Arg Gly Gln Arg
1               5                   10                  15

<210> SEQ ID NO 128
<211> LENGTH: 15
<212> TYPE: PRT
<213> ORGANISM: Arachis hypogaea

<400> SEQUENCE: 128

Asn Ala Gly Gly Glu Gln Glu Glu Arg Gly Gln Arg Arg Trp Ser
1               5                   10                  15

<210> SEQ ID NO 129
<211> LENGTH: 15
<212> TYPE: PRT
<213> ORGANISM: Arachis hypogaea

<400> SEQUENCE: 129

Gly Glu Gln Glu Glu Arg Gly Gln Arg Arg Trp Ser Thr Arg Ser
1               5                   10                  15

<210> SEQ ID NO 130
<211> LENGTH: 15
<212> TYPE: PRT
<213> ORGANISM: Arachis hypogaea

<400> SEQUENCE: 130

Glu Glu Arg Gly Gln Arg Arg Trp Ser Thr Arg Ser Ser Glu Asn
1               5                   10                  15

<210> SEQ ID NO 131
<211> LENGTH: 15
<212> TYPE: PRT
<213> ORGANISM: Arachis hypogaea

<400> SEQUENCE: 131

Lys Lys Gly Ser Glu Glu Glu Gly Asp Ile Thr Asn Pro Ile Asn
1               5                   10                  15

<210> SEQ ID NO 132
<211> LENGTH: 15
<212> TYPE: PRT
<213> ORGANISM: Arachis hypogaea

<400> SEQUENCE: 132

Ser Glu Glu Glu Gly Asp Ile Thr Asn Pro Ile Asn Leu Arg Glu
1               5                   10                  15

```
<210> SEQ ID NO 133
<211> LENGTH: 15
<212> TYPE: PRT
<213> ORGANISM: Arachis hypogaea

<400> SEQUENCE: 133

Glu Gly Asp Ile Thr Asn Pro Ile Asn Leu Arg Glu Gly Glu Pro
1               5                   10                  15

<210> SEQ ID NO 134
<211> LENGTH: 15
<212> TYPE: PRT
<213> ORGANISM: Arachis hypogaea

<400> SEQUENCE: 134

Ile Thr Asn Pro Ile Asn Leu Arg Glu Gly Glu Pro Asp Leu Ser
1               5                   10                  15

<210> SEQ ID NO 135
<211> LENGTH: 15
<212> TYPE: PRT
<213> ORGANISM: Arachis hypogaea

<400> SEQUENCE: 135

Pro Ile Asn Leu Arg Glu Gly Glu Pro Asp Leu Ser Asn Asn Phe
1               5                   10                  15

<210> SEQ ID NO 136
<211> LENGTH: 15
<212> TYPE: PRT
<213> ORGANISM: Arachis hypogaea

<400> SEQUENCE: 136

Leu Arg Glu Gly Glu Pro Asp Leu Ser Asn Asn Phe Gly Lys Leu
1               5                   10                  15

<210> SEQ ID NO 137
<211> LENGTH: 15
<212> TYPE: PRT
<213> ORGANISM: Arachis hypogaea

<400> SEQUENCE: 137

Gly Glu Pro Asp Leu Ser Asn Asn Phe Gly Lys Leu Phe Glu Val
1               5                   10                  15

<210> SEQ ID NO 138
<211> LENGTH: 15
<212> TYPE: PRT
<213> ORGANISM: Arachis hypogaea

<400> SEQUENCE: 138

Asp Leu Ser Asn Asn Phe Gly Lys Leu Phe Glu Val Lys Pro Asp
1               5                   10                  15

<210> SEQ ID NO 139
<211> LENGTH: 15
<212> TYPE: PRT
<213> ORGANISM: Arachis hypogaea

<400> SEQUENCE: 139

Asn Asn Phe Gly Lys Leu Phe Glu Val Lys Pro Asp Lys Lys Asn
1               5                   10                  15

<210> SEQ ID NO 140
<211> LENGTH: 15
```

```
<212> TYPE: PRT
<213> ORGANISM: Arachis hypogaea

<400> SEQUENCE: 140

Gly Lys Leu Phe Glu Val Lys Pro Asp Lys Lys Asn Pro Gln Leu
1               5                   10                  15

<210> SEQ ID NO 141
<211> LENGTH: 15
<212> TYPE: PRT
<213> ORGANISM: Arachis hypogaea

<400> SEQUENCE: 141

Lys Lys Asn Pro Gln Leu Gln Asp Leu Asp Met Met Leu Thr Cys
1               5                   10                  15

<210> SEQ ID NO 142
<211> LENGTH: 15
<212> TYPE: PRT
<213> ORGANISM: Arachis hypogaea

<400> SEQUENCE: 142

Pro Gln Leu Gln Asp Leu Asp Met Met Leu Thr Cys Val Glu Ile
1               5                   10                  15

<210> SEQ ID NO 143
<211> LENGTH: 15
<212> TYPE: PRT
<213> ORGANISM: Arachis hypogaea

<400> SEQUENCE: 143

Gln Asp Leu Asp Met Met Leu Thr Cys Val Glu Ile Lys Glu Gly
1               5                   10                  15

<210> SEQ ID NO 144
<211> LENGTH: 15
<212> TYPE: PRT
<213> ORGANISM: Arachis hypogaea

<400> SEQUENCE: 144

Asp Met Met Leu Thr Cys Val Glu Ile Lys Glu Gly Ala Leu Met
1               5                   10                  15

<210> SEQ ID NO 145
<211> LENGTH: 15
<212> TYPE: PRT
<213> ORGANISM: Arachis hypogaea

<400> SEQUENCE: 145

Leu Thr Cys Val Glu Ile Lys Glu Gly Ala Leu Met Leu Pro His
1               5                   10                  15

<210> SEQ ID NO 146
<211> LENGTH: 15
<212> TYPE: PRT
<213> ORGANISM: Arachis hypogaea

<400> SEQUENCE: 146

Val Glu Ile Lys Glu Gly Ala Leu Met Leu Pro His Phe Asn Ser
1               5                   10                  15

<210> SEQ ID NO 147
<211> LENGTH: 15
<212> TYPE: PRT
<213> ORGANISM: Arachis hypogaea
```

<400> SEQUENCE: 147

Lys Glu Gly Ala Leu Met Leu Pro His Phe Asn Ser Lys Ala Met
1               5                   10                  15

<210> SEQ ID NO 148
<211> LENGTH: 15
<212> TYPE: PRT
<213> ORGANISM: Arachis hypogaea

<400> SEQUENCE: 148

Ser Asn Arg Glu Val Arg Arg Tyr Thr Ala Arg Leu Lys Glu Gly
1               5                   10                  15

<210> SEQ ID NO 149
<211> LENGTH: 15
<212> TYPE: PRT
<213> ORGANISM: Arachis hypogaea

<400> SEQUENCE: 149

Glu Val Arg Arg Tyr Thr Ala Arg Leu Lys Glu Gly Asp Val Phe
1               5                   10                  15

<210> SEQ ID NO 150
<211> LENGTH: 15
<212> TYPE: PRT
<213> ORGANISM: Arachis hypogaea

<400> SEQUENCE: 150

Arg Tyr Thr Ala Arg Leu Lys Glu Gly Asp Val Phe Ile Met Pro
1               5                   10                  15

<210> SEQ ID NO 151
<211> LENGTH: 15
<212> TYPE: PRT
<213> ORGANISM: Arachis hypogaea

<400> SEQUENCE: 151

Ala Arg Leu Lys Glu Gly Asp Val Phe Ile Met Pro Ala Ala His
1               5                   10                  15

<210> SEQ ID NO 152
<211> LENGTH: 15
<212> TYPE: PRT
<213> ORGANISM: Arachis hypogaea

<400> SEQUENCE: 152

Lys Glu Gly Asp Val Phe Ile Met Pro Ala Ala His Pro Val Ala
1               5                   10                  15

<210> SEQ ID NO 153
<211> LENGTH: 15
<212> TYPE: PRT
<213> ORGANISM: Arachis hypogaea

<400> SEQUENCE: 153

Asp Val Phe Ile Met Pro Ala Ala His Pro Val Ala Ile Asn Ala
1               5                   10                  15

<210> SEQ ID NO 154
<211> LENGTH: 15
<212> TYPE: PRT
<213> ORGANISM: Arachis hypogaea

<400> SEQUENCE: 154

```
Pro Val Ala Ile Asn Ala Ser Ser Glu Leu His Leu Leu Gly Phe
1               5                   10                  15

<210> SEQ ID NO 155
<211> LENGTH: 15
<212> TYPE: PRT
<213> ORGANISM: Arachis hypogaea

<400> SEQUENCE: 155

Ile Asn Ala Ser Ser Glu Leu His Leu Leu Gly Phe Gly Ile Asn
1               5                   10                  15

<210> SEQ ID NO 156
<211> LENGTH: 15
<212> TYPE: PRT
<213> ORGANISM: Arachis hypogaea

<400> SEQUENCE: 156

Ser Ser Glu Leu His Leu Leu Gly Phe Gly Ile Asn Ala Glu Asn
1               5                   10                  15

<210> SEQ ID NO 157
<211> LENGTH: 15
<212> TYPE: PRT
<213> ORGANISM: Arachis hypogaea

<400> SEQUENCE: 157

Leu His Leu Leu Gly Phe Gly Ile Asn Ala Glu Asn Asn His Arg
1               5                   10                  15

<210> SEQ ID NO 158
<211> LENGTH: 15
<212> TYPE: PRT
<213> ORGANISM: Arachis hypogaea

<400> SEQUENCE: 158

Leu Gly Phe Gly Ile Asn Ala Glu Asn Asn His Arg Ile Phe Leu
1               5                   10                  15

<210> SEQ ID NO 159
<211> LENGTH: 15
<212> TYPE: PRT
<213> ORGANISM: Arachis hypogaea

<400> SEQUENCE: 159

Gly Ile Asn Ala Glu Asn Asn His Arg Ile Phe Leu Ala Gly Asp
1               5                   10                  15

<210> SEQ ID NO 160
<211> LENGTH: 15
<212> TYPE: PRT
<213> ORGANISM: Arachis hypogaea

<400> SEQUENCE: 160

Ala Glu Asn Asn His Arg Ile Phe Leu Ala Gly Asp Lys Asp Asn
1               5                   10                  15

<210> SEQ ID NO 161
<211> LENGTH: 15
<212> TYPE: PRT
<213> ORGANISM: Arachis hypogaea

<400> SEQUENCE: 161

Asn His Arg Ile Phe Leu Ala Gly Asp Lys Asp Asn Val Ile Asp
```

<210> SEQ ID NO 162
<211> LENGTH: 15
<212> TYPE: PRT
<213> ORGANISM: Arachis hypogaea

<400> SEQUENCE: 162

Ile Phe Leu Ala Gly Asp Lys Asp Asn Val Ile Asp Gln Ile Glu
1               5                   10                  15

<210> SEQ ID NO 163
<211> LENGTH: 15
<212> TYPE: PRT
<213> ORGANISM: Arachis hypogaea

<400> SEQUENCE: 163

Ala Gly Asp Lys Asp Asn Val Ile Asp Gln Ile Glu Lys Gln Ala
1               5                   10                  15

<210> SEQ ID NO 164
<211> LENGTH: 15
<212> TYPE: PRT
<213> ORGANISM: Arachis hypogaea

<400> SEQUENCE: 164

Lys Asp Asn Val Ile Asp Gln Ile Glu Lys Gln Ala Lys Asp Leu
1               5                   10                  15

<210> SEQ ID NO 165
<211> LENGTH: 15
<212> TYPE: PRT
<213> ORGANISM: Arachis hypogaea

<400> SEQUENCE: 165

Val Ile Asp Gln Ile Glu Lys Gln Ala Lys Asp Leu Ala Phe Pro
1               5                   10                  15

<210> SEQ ID NO 166
<211> LENGTH: 15
<212> TYPE: PRT
<213> ORGANISM: Arachis hypogaea

<400> SEQUENCE: 166

Gln Ile Glu Lys Gln Ala Lys Asp Leu Ala Phe Pro Gly Ser Gly
1               5                   10                  15

<210> SEQ ID NO 167
<211> LENGTH: 15
<212> TYPE: PRT
<213> ORGANISM: Arachis hypogaea

<400> SEQUENCE: 167

Lys Gln Ala Lys Asp Leu Ala Phe Pro Gly Ser Gly Glu Gln Val
1               5                   10                  15

<210> SEQ ID NO 168
<211> LENGTH: 15
<212> TYPE: PRT
<213> ORGANISM: Arachis hypogaea

<400> SEQUENCE: 168

Lys Asp Leu Ala Phe Pro Gly Ser Gly Glu Gln Val Glu Lys Leu
1               5                   10                  15

<210> SEQ ID NO 169
<211> LENGTH: 15
<212> TYPE: PRT
<213> ORGANISM: Arachis hypogaea

<400> SEQUENCE: 169

Ala Phe Pro Gly Ser Gly Glu Gln Val Glu Lys Leu Ile Lys Asn
1               5                   10                  15

<210> SEQ ID NO 170
<211> LENGTH: 15
<212> TYPE: PRT
<213> ORGANISM: Arachis hypogaea

<400> SEQUENCE: 170

Gly Ser Gly Glu Gln Val Glu Lys Leu Ile Lys Asn Gln Lys Glu
1               5                   10                  15

<210> SEQ ID NO 171
<211> LENGTH: 15
<212> TYPE: PRT
<213> ORGANISM: Arachis hypogaea

<400> SEQUENCE: 171

Glu Gln Val Glu Lys Leu Ile Lys Asn Gln Lys Glu Ser His Phe
1               5                   10                  15

<210> SEQ ID NO 172
<211> LENGTH: 15
<212> TYPE: PRT
<213> ORGANISM: Arachis hypogaea

<400> SEQUENCE: 172

Glu Lys Leu Ile Lys Asn Gln Lys Glu Ser His Phe Val Ser Ala
1               5                   10                  15

<210> SEQ ID NO 173
<211> LENGTH: 15
<212> TYPE: PRT
<213> ORGANISM: Arachis hypogaea

<400> SEQUENCE: 173

Ile Lys Asn Gln Lys Glu Ser His Phe Val Ser Ala Arg Pro Gln
1               5                   10                  15

<210> SEQ ID NO 174
<211> LENGTH: 15
<212> TYPE: PRT
<213> ORGANISM: Arachis hypogaea

<400> SEQUENCE: 174

Gln Lys Glu Ser His Phe Val Ser Ala Arg Pro Gln Ser Gln Ser
1               5                   10                  15

<210> SEQ ID NO 175
<211> LENGTH: 15
<212> TYPE: PRT
<213> ORGANISM: Arachis hypogaea

<400> SEQUENCE: 175

Ser His Phe Val Ser Ala Arg Pro Gln Ser Gln Ser Gln Ser Pro
1               5                   10                  15

<210> SEQ ID NO 176

-continued

```
<211> LENGTH: 15
<212> TYPE: PRT
<213> ORGANISM: Arachis hypogaea

<400> SEQUENCE: 176

Val Ser Ala Arg Pro Gln Ser Gln Ser Gln Ser Pro Ser Ser Pro
1               5                   10                  15

<210> SEQ ID NO 177
<211> LENGTH: 15
<212> TYPE: PRT
<213> ORGANISM: Arachis hypogaea

<400> SEQUENCE: 177

Arg Pro Gln Ser Gln Ser Gln Ser Pro Ser Ser Pro Glu Lys Glu
1               5                   10                  15

<210> SEQ ID NO 178
<211> LENGTH: 15
<212> TYPE: PRT
<213> ORGANISM: Arachis hypogaea

<400> SEQUENCE: 178

Ser Gln Ser Gln Ser Pro Ser Ser Pro Glu Lys Glu Ser Pro Glu
1               5                   10                  15

<210> SEQ ID NO 179
<211> LENGTH: 15
<212> TYPE: PRT
<213> ORGANISM: Arachis hypogaea

<400> SEQUENCE: 179

Gln Ser Pro Ser Ser Pro Glu Lys Glu Ser Pro Glu Lys Glu Asp
1               5                   10                  15

<210> SEQ ID NO 180
<211> LENGTH: 15
<212> TYPE: PRT
<213> ORGANISM: Arachis hypogaea

<400> SEQUENCE: 180

Ser Ser Pro Glu Lys Glu Ser Pro Glu Lys Glu Asp Gln Glu Glu
1               5                   10                  15

<210> SEQ ID NO 181
<211> LENGTH: 15
<212> TYPE: PRT
<213> ORGANISM: Arachis hypogaea

<400> SEQUENCE: 181

Glu Lys Glu Ser Pro Lys Glu Asp Gln Glu Glu Glu Asn Gln
1               5                   10                  15

<210> SEQ ID NO 182
<211> LENGTH: 15
<212> TYPE: PRT
<213> ORGANISM: Arachis hypogaea

<400> SEQUENCE: 182

Ser Pro Glu Lys Glu Asp Gln Glu Glu Glu Asn Gln Gly Gly Lys
1               5                   10                  15

<210> SEQ ID NO 183
<211> LENGTH: 15
<212> TYPE: PRT
```

<213> ORGANISM: Arachis hypogaea

<400> SEQUENCE: 183

Lys Glu Asp Gln Glu Glu Asn Gln Gly Gly Lys Gly Pro Leu
1               5                   10                  15

<210> SEQ ID NO 184
<211> LENGTH: 15
<212> TYPE: PRT
<213> ORGANISM: Arachis hypogaea

<400> SEQUENCE: 184

Gln Glu Glu Asn Gln Gly Gly Lys Gly Pro Leu Leu Ser Ile
1               5                   10                  15

<210> SEQ ID NO 185
<211> LENGTH: 15
<212> TYPE: PRT
<213> ORGANISM: Arachis hypogaea

<400> SEQUENCE: 185

Ala Ala His Ala Ser Ala Arg Gln Gln Trp Glu Leu Gln Gly Asp
1               5                   10                  15

<210> SEQ ID NO 186
<211> LENGTH: 15
<212> TYPE: PRT
<213> ORGANISM: Arachis hypogaea

<400> SEQUENCE: 186

Ala Ser Ala Arg Gln Gln Trp Glu Leu Gln Gly Asp Arg Arg Cys
1               5                   10                  15

<210> SEQ ID NO 187
<211> LENGTH: 15
<212> TYPE: PRT
<213> ORGANISM: Arachis hypogaea

<400> SEQUENCE: 187

Arg Gln Gln Trp Glu Leu Gln Gly Asp Arg Arg Cys Gln Ser Gln
1               5                   10                  15

<210> SEQ ID NO 188
<211> LENGTH: 15
<212> TYPE: PRT
<213> ORGANISM: Arachis hypogaea

<400> SEQUENCE: 188

Trp Glu Leu Gln Gly Asp Arg Arg Cys Gln Ser Gln Leu Glu Arg
1               5                   10                  15

<210> SEQ ID NO 189
<211> LENGTH: 15
<212> TYPE: PRT
<213> ORGANISM: Arachis hypogaea

<400> SEQUENCE: 189

Gln Gly Asp Arg Arg Cys Gln Ser Gln Leu Glu Arg Ala Asn Leu
1               5                   10                  15

<210> SEQ ID NO 190
<211> LENGTH: 15
<212> TYPE: PRT
<213> ORGANISM: Arachis hypogaea -continued

<400> SEQUENCE: 190

Arg Arg Cys Gln Ser Gln Leu Glu Arg Ala Asn Leu Arg Pro Cys
1               5                   10                  15

<210> SEQ ID NO 191
<211> LENGTH: 15
<212> TYPE: PRT
<213> ORGANISM: Arachis hypogaea

<400> SEQUENCE: 191

Gln Ser Gln Leu Glu Arg Ala Asn Leu Arg Pro Cys Glu Gln His
1               5                   10                  15

<210> SEQ ID NO 192
<211> LENGTH: 15
<212> TYPE: PRT
<213> ORGANISM: Arachis hypogaea

<400> SEQUENCE: 192

Leu Glu Arg Ala Asn Leu Arg Pro Cys Glu Gln His Leu Met Gln
1               5                   10                  15

<210> SEQ ID NO 193
<211> LENGTH: 15
<212> TYPE: PRT
<213> ORGANISM: Arachis hypogaea

<400> SEQUENCE: 193

Ala Asn Leu Arg Pro Cys Glu Gln His Leu Met Gln Lys Ile Gln
1               5                   10                  15

<210> SEQ ID NO 194
<211> LENGTH: 15
<212> TYPE: PRT
<213> ORGANISM: Arachis hypogaea

<400> SEQUENCE: 194

Arg Pro Cys Glu Gln His Leu Met Gln Lys Ile Gln Arg Asp Glu
1               5                   10                  15

<210> SEQ ID NO 195
<211> LENGTH: 15
<212> TYPE: PRT
<213> ORGANISM: Arachis hypogaea

<400> SEQUENCE: 195

Glu Gln His Leu Met Gln Lys Ile Gln Arg Asp Glu Asp Ser Tyr
1               5                   10                  15

<210> SEQ ID NO 196
<211> LENGTH: 15
<212> TYPE: PRT
<213> ORGANISM: Arachis hypogaea

<400> SEQUENCE: 196

Leu Met Gln Lys Ile Gln Arg Asp Glu Asp Ser Tyr Glu Arg Asp
1               5                   10                  15

<210> SEQ ID NO 197
<211> LENGTH: 15
<212> TYPE: PRT
<213> ORGANISM: Arachis hypogaea

<400> SEQUENCE: 197

Lys Ile Gln Arg Asp Glu Asp Ser Tyr Glu Arg Asp Pro Tyr Ser
1               5                   10                  15

<210> SEQ ID NO 198
<211> LENGTH: 15
<212> TYPE: PRT
<213> ORGANISM: Arachis hypogaea

<400> SEQUENCE: 198

Arg Asp Glu Asp Ser Tyr Glu Arg Asp Pro Tyr Ser Pro Ser Gln
1               5                   10                  15

<210> SEQ ID NO 199
<211> LENGTH: 15
<212> TYPE: PRT
<213> ORGANISM: Arachis hypogaea

<400> SEQUENCE: 199

Asp Ser Tyr Glu Arg Asp Pro Tyr Ser Pro Ser Gln Asp Pro Tyr
1               5                   10                  15

<210> SEQ ID NO 200
<211> LENGTH: 15
<212> TYPE: PRT
<213> ORGANISM: Arachis hypogaea

<400> SEQUENCE: 200

Glu Arg Asp Pro Tyr Ser Pro Ser Gln Asp Pro Tyr Ser Pro Ser
1               5                   10                  15

<210> SEQ ID NO 201
<211> LENGTH: 15
<212> TYPE: PRT
<213> ORGANISM: Arachis hypogaea

<400> SEQUENCE: 201

Pro Tyr Ser Pro Ser Gln Asp Pro Tyr Ser Pro Ser Pro Tyr Asp
1               5                   10                  15

<210> SEQ ID NO 202
<211> LENGTH: 15
<212> TYPE: PRT
<213> ORGANISM: Arachis hypogaea

<400> SEQUENCE: 202

Pro Ser Gln Asp Pro Tyr Ser Pro Ser Pro Tyr Asp Arg Arg Gly
1               5                   10                  15

<210> SEQ ID NO 203
<211> LENGTH: 15
<212> TYPE: PRT
<213> ORGANISM: Arachis hypogaea

<400> SEQUENCE: 203

Asp Pro Tyr Ser Pro Ser Pro Tyr Asp Arg Arg Gly Ala Gly Ser
1               5                   10                  15

<210> SEQ ID NO 204
<211> LENGTH: 15
<212> TYPE: PRT
<213> ORGANISM: Arachis hypogaea

<400> SEQUENCE: 204

Ser Pro Ser Pro Tyr Asp Arg Arg Gly Ala Gly Ser Ser Gln His
1               5                   10                  15

```
<210> SEQ ID NO 205
<211> LENGTH: 15
<212> TYPE: PRT
<213> ORGANISM: Arachis hypogaea

<400> SEQUENCE: 205

Pro Tyr Asp Arg Arg Gly Ala Gly Ser Ser Gln His Gln Glu Arg
1               5                   10                  15

<210> SEQ ID NO 206
<211> LENGTH: 15
<212> TYPE: PRT
<213> ORGANISM: Arachis hypogaea

<400> SEQUENCE: 206

Gln Glu Arg Cys Cys Asn Glu Leu Asn Glu Phe Glu Asn Asn Gln
1               5                   10                  15

<210> SEQ ID NO 207
<211> LENGTH: 15
<212> TYPE: PRT
<213> ORGANISM: Arachis hypogaea

<400> SEQUENCE: 207

Cys Cys Asn Glu Leu Asn Glu Phe Glu Asn Asn Gln Arg Cys Met
1               5                   10                  15

<210> SEQ ID NO 208
<211> LENGTH: 15
<212> TYPE: PRT
<213> ORGANISM: Arachis hypogaea

<400> SEQUENCE: 208

Glu Leu Asn Glu Phe Glu Asn Asn Gln Arg Cys Met Cys Glu Ala
1               5                   10                  15

<210> SEQ ID NO 209
<211> LENGTH: 15
<212> TYPE: PRT
<213> ORGANISM: Arachis hypogaea

<400> SEQUENCE: 209

Glu Phe Glu Asn Asn Gln Arg Cys Met Cys Glu Ala Leu Gln Gln
1               5                   10                  15

<210> SEQ ID NO 210
<211> LENGTH: 15
<212> TYPE: PRT
<213> ORGANISM: Arachis hypogaea

<400> SEQUENCE: 210

Arg Cys Met Cys Glu Ala Leu Gln Gln Ile Met Glu Asn Gln Ser
1               5                   10                  15

<210> SEQ ID NO 211
<211> LENGTH: 15
<212> TYPE: PRT
<213> ORGANISM: Arachis hypogaea

<400> SEQUENCE: 211

Cys Glu Ala Leu Gln Gln Ile Met Glu Asn Gln Ser Asp Arg Leu
1               5                   10                  15
```

```
<210> SEQ ID NO 212
<211> LENGTH: 15
<212> TYPE: PRT
<213> ORGANISM: Arachis hypogaea

<400> SEQUENCE: 212

Leu Gln Gln Ile Met Glu Asn Gln Ser Asp Arg Leu Gln Gly Arg
1               5                  10                  15

<210> SEQ ID NO 213
<211> LENGTH: 15
<212> TYPE: PRT
<213> ORGANISM: Arachis hypogaea

<400> SEQUENCE: 213

Ile Met Glu Asn Gln Ser Asp Arg Leu Gln Gly Arg Gln Gln Glu
1               5                  10                  15

<210> SEQ ID NO 214
<211> LENGTH: 15
<212> TYPE: PRT
<213> ORGANISM: Arachis hypogaea

<400> SEQUENCE: 214

Asn Gln Ser Asp Arg Leu Gln Gly Arg Gln Gln Glu Gln Gln Phe
1               5                  10                  15

<210> SEQ ID NO 215
<211> LENGTH: 15
<212> TYPE: PRT
<213> ORGANISM: Arachis hypogaea

<400> SEQUENCE: 215

Asp Arg Leu Gln Gly Arg Gln Gln Glu Gln Gln Phe Lys Arg Glu
1               5                  10                  15

<210> SEQ ID NO 216
<211> LENGTH: 15
<212> TYPE: PRT
<213> ORGANISM: Arachis hypogaea

<400> SEQUENCE: 216

Gln Gly Arg Gln Gln Glu Gln Gln Phe Lys Arg Glu Leu Arg Asn
1               5                  10                  15

<210> SEQ ID NO 217
<211> LENGTH: 15
<212> TYPE: PRT
<213> ORGANISM: Arachis hypogaea

<400> SEQUENCE: 217

Gln Gln Glu Gln Gln Phe Lys Arg Glu Leu Arg Asn Leu Pro Gln
1               5                  10                  15

<210> SEQ ID NO 218
<211> LENGTH: 15
<212> TYPE: PRT
<213> ORGANISM: Arachis hypogaea

<400> SEQUENCE: 218

Gln Gln Phe Lys Arg Glu Leu Arg Asn Leu Pro Gln Gln Cys Gly
1               5                  10                  15

<210> SEQ ID NO 219
<211> LENGTH: 15
```

```
<212> TYPE: PRT
<213> ORGANISM: Arachis hypogaea

<400> SEQUENCE: 219

Lys Arg Glu Leu Arg Asn Leu Pro Gln Gln Cys Gly Leu Arg Ala
1               5                   10                  15

<210> SEQ ID NO 220
<211> LENGTH: 15
<212> TYPE: PRT
<213> ORGANISM: Arachis hypogaea

<400> SEQUENCE: 220

Leu Pro Gln Gln Cys Gly Leu Arg Ala Pro Gln Arg Cys Asp Leu
1               5                   10                  15

<210> SEQ ID NO 221
<211> LENGTH: 15
<212> TYPE: PRT
<213> ORGANISM: Arachis hypogaea

<400> SEQUENCE: 221

Gln Cys Gly Leu Arg Ala Pro Gln Arg Cys Asp Leu Asp Val Glu
1               5                   10                  15

<210> SEQ ID NO 222
<211> LENGTH: 15
<212> TYPE: PRT
<213> ORGANISM: Arachis hypogaea

<400> SEQUENCE: 222

Leu Arg Ala Pro Gln Arg Cys Asp Leu Asp Val Glu Ser Gly Gly
1               5                   10                  15

<210> SEQ ID NO 223
<211> LENGTH: 15
<212> TYPE: PRT
<213> ORGANISM: Arachis hypogaea

<400> SEQUENCE: 223

Arg Ile Glu Ser Glu Gly Gly Tyr Ile Glu Thr Trp Asn Pro Asn
1               5                   10                  15

<210> SEQ ID NO 224
<211> LENGTH: 15
<212> TYPE: PRT
<213> ORGANISM: Arachis hypogaea

<400> SEQUENCE: 224

Asn Gln Glu Phe Glu Cys Ala Gly Val Ala Leu Ser Arg Leu Val
1               5                   10                  15

<210> SEQ ID NO 225
<211> LENGTH: 15
<212> TYPE: PRT
<213> ORGANISM: Arachis hypogaea

<400> SEQUENCE: 225

Ala Gly Val Ala Leu Ser Arg Leu Val Leu Arg Arg Asn Ala Leu
1               5                   10                  15

<210> SEQ ID NO 226
<211> LENGTH: 15
<212> TYPE: PRT
<213> ORGANISM: Arachis hypogaea
```

<400> SEQUENCE: 226

Ala Leu Ser Arg Leu Val Leu Arg Arg Asn Ala Leu Arg Arg Pro
1               5                   10                  15

<210> SEQ ID NO 227
<211> LENGTH: 15
<212> TYPE: PRT
<213> ORGANISM: Arachis hypogaea

<400> SEQUENCE: 227

Arg Leu Val Leu Arg Arg Asn Ala Leu Arg Arg Pro Phe Tyr Ser
1               5                   10                  15

<210> SEQ ID NO 228
<211> LENGTH: 15
<212> TYPE: PRT
<213> ORGANISM: Arachis hypogaea

<400> SEQUENCE: 228

Leu Arg Arg Asn Ala Leu Arg Arg Pro Phe Tyr Ser Asn Ala Pro
1               5                   10                  15

<210> SEQ ID NO 229
<211> LENGTH: 15
<212> TYPE: PRT
<213> ORGANISM: Arachis hypogaea

<400> SEQUENCE: 229

Asn Ala Leu Arg Arg Pro Phe Tyr Ser Asn Ala Pro Gln Glu Ile
1               5                   10                  15

<210> SEQ ID NO 230
<211> LENGTH: 15
<212> TYPE: PRT
<213> ORGANISM: Arachis hypogaea

<400> SEQUENCE: 230

His Tyr Glu Glu Pro His Thr Gln Gly Arg Arg Ser Gln Ser Gln
1               5                   10                  15

<210> SEQ ID NO 231
<211> LENGTH: 15
<212> TYPE: PRT
<213> ORGANISM: Arachis hypogaea

<400> SEQUENCE: 231

Glu Pro His Thr Gln Gly Arg Arg Ser Gln Ser Gln Arg Pro Pro
1               5                   10                  15

<210> SEQ ID NO 232
<211> LENGTH: 15
<212> TYPE: PRT
<213> ORGANISM: Arachis hypogaea

<400> SEQUENCE: 232

Thr Gln Gly Arg Arg Ser Gln Ser Gln Arg Pro Pro Arg Arg Leu
1               5                   10                  15

<210> SEQ ID NO 233
<211> LENGTH: 15
<212> TYPE: PRT
<213> ORGANISM: Arachis hypogaea

<400> SEQUENCE: 233

```
Arg Arg Ser Gln Ser Gln Arg Pro Pro Arg Leu Gln Gly Glu
1               5                   10                  15

<210> SEQ ID NO 234
<211> LENGTH: 15
<212> TYPE: PRT
<213> ORGANISM: Arachis hypogaea

<400> SEQUENCE: 234

Arg Arg Leu Gln Gly Glu Asp Gln Ser Gln Gln Gln Arg Asp Ser
1               5                   10                  15

<210> SEQ ID NO 235
<211> LENGTH: 15
<212> TYPE: PRT
<213> ORGANISM: Arachis hypogaea

<400> SEQUENCE: 235

Gln Gly Glu Asp Gln Ser Gln Gln Gln Arg Asp Ser His Gln Lys
1               5                   10                  15

<210> SEQ ID NO 236
<211> LENGTH: 15
<212> TYPE: PRT
<213> ORGANISM: Arachis hypogaea

<400> SEQUENCE: 236

Asn Thr Glu Gln Glu Phe Leu Arg Tyr Gln Gln Gln Ser Arg Gln
1               5                   10                  15

<210> SEQ ID NO 237
<211> LENGTH: 15
<212> TYPE: PRT
<213> ORGANISM: Arachis hypogaea

<400> SEQUENCE: 237

Gln Glu Phe Leu Arg Tyr Gln Gln Gln Ser Arg Gln Ser Arg Arg
1               5                   10                  15

<210> SEQ ID NO 238
<211> LENGTH: 15
<212> TYPE: PRT
<213> ORGANISM: Arachis hypogaea

<400> SEQUENCE: 238

Pro Tyr Ser Pro Gln Ser Gln Pro Arg Gln Glu Glu Arg Glu Phe
1               5                   10                  15

<210> SEQ ID NO 239
<211> LENGTH: 15
<212> TYPE: PRT
<213> ORGANISM: Arachis hypogaea

<400> SEQUENCE: 239

Pro Gln Ser Gln Pro Arg Gln Glu Glu Arg Glu Phe Ser Pro Arg
1               5                   10                  15

<210> SEQ ID NO 240
<211> LENGTH: 15
<212> TYPE: PRT
<213> ORGANISM: Arachis hypogaea

<400> SEQUENCE: 240

Gln Pro Arg Gln Glu Glu Arg Glu Phe Ser Pro Arg Gly Gln His
```

<210> SEQ ID NO 241
<211> LENGTH: 15
<212> TYPE: PRT
<213> ORGANISM: Arachis hypogaea

<400> SEQUENCE: 241

Gln Glu Glu Arg Glu Phe Ser Pro Arg Gly Gln His Ser Arg Arg
1               5                   10                  15

<210> SEQ ID NO 242
<211> LENGTH: 15
<212> TYPE: PRT
<213> ORGANISM: Arachis hypogaea

<400> SEQUENCE: 242

Ser Pro Arg Gly Gln His Ser Arg Arg Glu Arg Ala Gly Gln Glu
1               5                   10                  15

<210> SEQ ID NO 243
<211> LENGTH: 15
<212> TYPE: PRT
<213> ORGANISM: Arachis hypogaea

<400> SEQUENCE: 243

Gly Gln His Ser Arg Arg Glu Arg Ala Gly Gln Glu Glu Glu Asn
1               5                   10                  15

<210> SEQ ID NO 244
<211> LENGTH: 15
<212> TYPE: PRT
<213> ORGANISM: Arachis hypogaea

<400> SEQUENCE: 244

Ser Arg Arg Glu Arg Ala Gly Gln Glu Glu Glu Asn Glu Gly Gly
1               5                   10                  15

<210> SEQ ID NO 245
<211> LENGTH: 15
<212> TYPE: PRT
<213> ORGANISM: Arachis hypogaea

<400> SEQUENCE: 245

Gly Gln Glu Glu Glu Asn Glu Gly Gly Asn Ile Phe Ser Gly Phe
1               5                   10                  15

<210> SEQ ID NO 246
<211> LENGTH: 15
<212> TYPE: PRT
<213> ORGANISM: Arachis hypogaea

<400> SEQUENCE: 246

Glu Glu Asn Glu Gly Gly Asn Ile Phe Ser Gly Phe Thr Pro Glu
1               5                   10                  15

<210> SEQ ID NO 247
<211> LENGTH: 15
<212> TYPE: PRT
<213> ORGANISM: Arachis hypogaea

<400> SEQUENCE: 247

Glu Gly Gly Asn Ile Phe Ser Gly Phe Thr Pro Glu Phe Leu Glu
1               5                   10                  15

```
<210> SEQ ID NO 248
<211> LENGTH: 15
<212> TYPE: PRT
<213> ORGANISM: Arachis hypogaea

<400> SEQUENCE: 248

Asn Ile Phe Ser Gly Phe Thr Pro Glu Phe Leu Glu Gln Ala Phe
1               5                   10                  15

<210> SEQ ID NO 249
<211> LENGTH: 15
<212> TYPE: PRT
<213> ORGANISM: Arachis hypogaea

<400> SEQUENCE: 249

Ser Gly Phe Thr Pro Glu Phe Leu Glu Gln Ala Phe Gln Val Asp
1               5                   10                  15

<210> SEQ ID NO 250
<211> LENGTH: 15
<212> TYPE: PRT
<213> ORGANISM: Arachis hypogaea

<400> SEQUENCE: 250

Thr Pro Glu Phe Leu Glu Gln Ala Phe Gln Val Asp Asp Arg Gln
1               5                   10                  15

<210> SEQ ID NO 251
<211> LENGTH: 15
<212> TYPE: PRT
<213> ORGANISM: Arachis hypogaea

<400> SEQUENCE: 251

Glu Ser Glu Glu Glu Gly Ala Ile Val Thr Val Arg Gly Gly Leu
1               5                   10                  15

<210> SEQ ID NO 252
<211> LENGTH: 15
<212> TYPE: PRT
<213> ORGANISM: Arachis hypogaea

<400> SEQUENCE: 252

Glu Glu Gly Ala Ile Val Thr Val Arg Gly Gly Leu Arg Ile Leu
1               5                   10                  15

<210> SEQ ID NO 253
<211> LENGTH: 15
<212> TYPE: PRT
<213> ORGANISM: Arachis hypogaea

<400> SEQUENCE: 253

Ala Ile Val Thr Val Arg Gly Gly Leu Arg Ile Leu Ser Pro Asp
1               5                   10                  15

<210> SEQ ID NO 254
<211> LENGTH: 15
<212> TYPE: PRT
<213> ORGANISM: Arachis hypogaea

<400> SEQUENCE: 254

Thr Val Arg Gly Gly Leu Arg Ile Leu Ser Pro Asp Arg Lys Arg
1               5                   10                  15

<210> SEQ ID NO 255
```

```
<211> LENGTH: 15
<212> TYPE: PRT
<213> ORGANISM: Arachis hypogaea

<400> SEQUENCE: 255

Gly Gly Leu Arg Ile Leu Ser Pro Asp Arg Lys Arg Arg Ala Asp
1               5                   10                  15

<210> SEQ ID NO 256
<211> LENGTH: 15
<212> TYPE: PRT
<213> ORGANISM: Arachis hypogaea

<400> SEQUENCE: 256

Arg Ile Leu Ser Pro Asp Arg Lys Arg Arg Ala Asp Glu Glu Glu
1               5                   10                  15

<210> SEQ ID NO 257
<211> LENGTH: 15
<212> TYPE: PRT
<213> ORGANISM: Arachis hypogaea

<400> SEQUENCE: 257

Arg Lys Arg Arg Ala Asp Glu Glu Glu Tyr Asp Glu Asp Glu
1               5                   10                  15

<210> SEQ ID NO 258
<211> LENGTH: 15
<212> TYPE: PRT
<213> ORGANISM: Arachis hypogaea

<400> SEQUENCE: 258

Arg Ala Asp Glu Glu Glu Tyr Asp Glu Asp Glu Tyr Glu Tyr
1               5                   10                  15

<210> SEQ ID NO 259
<211> LENGTH: 15
<212> TYPE: PRT
<213> ORGANISM: Arachis hypogaea

<400> SEQUENCE: 259

Glu Glu Glu Glu Tyr Asp Glu Asp Glu Tyr Glu Tyr Asp Glu Glu
1               5                   10                  15

<210> SEQ ID NO 260
<211> LENGTH: 15
<212> TYPE: PRT
<213> ORGANISM: Arachis hypogaea

<400> SEQUENCE: 260

Glu Tyr Asp Glu Asp Glu Tyr Glu Tyr Asp Glu Glu Asp Arg Arg
1               5                   10                  15

<210> SEQ ID NO 261
<211> LENGTH: 15
<212> TYPE: PRT
<213> ORGANISM: Arachis hypogaea

<400> SEQUENCE: 261

Glu Asp Glu Tyr Glu Tyr Asp Glu Glu Asp Arg Arg Arg Gly Arg
1               5                   10                  15

<210> SEQ ID NO 262
<211> LENGTH: 15
<212> TYPE: PRT
```

-continued

<213> ORGANISM: Arachis hypogaea

<400> SEQUENCE: 262

Tyr Glu Tyr Asp Glu Glu Asp Arg Arg Arg Gly Arg Gly Ser Arg
1               5                   10                  15

<210> SEQ ID NO 263
<211> LENGTH: 15
<212> TYPE: PRT
<213> ORGANISM: Arachis hypogaea

<400> SEQUENCE: 263

Asp Glu Glu Asp Arg Arg Gly Arg Gly Ser Arg Gly Arg Gly
1               5                   10                  15

<210> SEQ ID NO 264
<211> LENGTH: 15
<212> TYPE: PRT
<213> ORGANISM: Arachis hypogaea

<400> SEQUENCE: 264

Asp Arg Arg Arg Gly Arg Gly Ser Arg Gly Arg Gly Asn Gly Ile
1               5                   10                  15

<210> SEQ ID NO 265
<211> LENGTH: 15
<212> TYPE: PRT
<213> ORGANISM: Arachis hypogaea

<400> SEQUENCE: 265

Arg Gly Arg Gly Ser Arg Gly Arg Gly Asn Gly Ile Glu Glu Thr
1               5                   10                  15

<210> SEQ ID NO 266
<211> LENGTH: 15
<212> TYPE: PRT
<213> ORGANISM: Arachis hypogaea

<400> SEQUENCE: 266

Gly Ser Arg Gly Arg Gly Asn Gly Ile Glu Glu Thr Ile Cys Thr
1               5                   10                  15

<210> SEQ ID NO 267
<211> LENGTH: 15
<212> TYPE: PRT
<213> ORGANISM: Arachis hypogaea

<400> SEQUENCE: 267

Gly Arg Gly Asn Gly Ile Glu Glu Thr Ile Cys Thr Ala Ser Ala
1               5                   10                  15

<210> SEQ ID NO 268
<211> LENGTH: 15
<212> TYPE: PRT
<213> ORGANISM: Arachis hypogaea

<400> SEQUENCE: 268

Asn Gly Ile Glu Glu Thr Ile Cys Thr Ala Ser Ala Lys Lys Asn
1               5                   10                  15

<210> SEQ ID NO 269
<211> LENGTH: 15
<212> TYPE: PRT
<213> ORGANISM: Arachis hypogaea

```
<400> SEQUENCE: 269

Ile Ala Asn Leu Ala Gly Glu Asn Ser Val Ile Asp Asn Leu Pro
1               5                   10                  15

<210> SEQ ID NO 270
<211> LENGTH: 15
<212> TYPE: PRT
<213> ORGANISM: Arachis hypogaea

<400> SEQUENCE: 270

Leu Ala Gly Glu Asn Ser Val Ile Asp Asn Leu Pro Glu Glu Val
1               5                   10                  15

<210> SEQ ID NO 271
<211> LENGTH: 15
<212> TYPE: PRT
<213> ORGANISM: Arachis hypogaea

<400> SEQUENCE: 271

Glu Asn Ser Val Ile Asp Asn Leu Pro Glu Glu Val Val Ala Asn
1               5                   10                  15

<210> SEQ ID NO 272
<211> LENGTH: 15
<212> TYPE: PRT
<213> ORGANISM: Arachis hypogaea

<400> SEQUENCE: 272

Val Ile Asp Asn Leu Pro Glu Glu Val Val Ala Asn Ser Tyr Gly
1               5                   10                  15

<210> SEQ ID NO 273
<211> LENGTH: 15
<212> TYPE: PRT
<213> ORGANISM: Arachis hypogaea

<400> SEQUENCE: 273

Glu Gln Ala Arg Gln Leu Lys Asn Asn Asn Pro Phe Lys Phe Phe
1               5                   10                  15

<210> SEQ ID NO 274
<211> LENGTH: 15
<212> TYPE: PRT
<213> ORGANISM: Arachis hypogaea

<400> SEQUENCE: 274

Arg Gln Leu Lys Asn Asn Asn Pro Phe Lys Phe Phe Val Pro Pro
1               5                   10                  15

<210> SEQ ID NO 275
<211> LENGTH: 15
<212> TYPE: PRT
<213> ORGANISM: Arachis hypogaea

<400> SEQUENCE: 275

Lys Asn Asn Asn Pro Phe Lys Phe Phe Val Pro Pro Ser Gln Gln
1               5                   10                  15

<210> SEQ ID NO 276
<211> LENGTH: 15
<212> TYPE: PRT
<213> ORGANISM: Arachis hypogaea

<400> SEQUENCE: 276
```

Asn Pro Phe Lys Phe Phe Val Pro Pro Ser Gln Gln Ser Pro Arg
1               5                   10                  15

<210> SEQ ID NO 277
<211> LENGTH: 15
<212> TYPE: PRT
<213> ORGANISM: Arachis hypogaea

<400> SEQUENCE: 277

Lys Phe Phe Val Pro Pro Ser Gln Gln Ser Pro Arg Ala Val Ala
1               5                   10                  15

<210> SEQ ID NO 278
<211> LENGTH: 15
<212> TYPE: PRT
<213> ORGANISM: Gallus gallus

<400> SEQUENCE: 278

Met Gly Ser Ile Gly Ala Ala Ser Met Glu Phe Cys Phe Asp Val
1               5                   10                  15

<210> SEQ ID NO 279
<211> LENGTH: 15
<212> TYPE: PRT
<213> ORGANISM: Gallus gallus

<400> SEQUENCE: 279

Ile Gly Ala Ala Ser Met Glu Phe Cys Phe Asp Val Phe Lys Glu
1               5                   10                  15

<210> SEQ ID NO 280
<211> LENGTH: 15
<212> TYPE: PRT
<213> ORGANISM: Gallus gallus

<400> SEQUENCE: 280

Ala Ser Met Glu Phe Cys Phe Asp Val Phe Lys Glu Leu Lys Val
1               5                   10                  15

<210> SEQ ID NO 281
<211> LENGTH: 15
<212> TYPE: PRT
<213> ORGANISM: Gallus gallus

<400> SEQUENCE: 281

Glu Phe Cys Phe Asp Val Phe Lys Glu Leu Lys Val His His Ala
1               5                   10                  15

<210> SEQ ID NO 282
<211> LENGTH: 15
<212> TYPE: PRT
<213> ORGANISM: Gallus gallus

<400> SEQUENCE: 282

Phe Asp Val Phe Lys Glu Leu Lys Val His His Ala Asn Glu Asn
1               5                   10                  15

<210> SEQ ID NO 283
<211> LENGTH: 15
<212> TYPE: PRT
<213> ORGANISM: Gallus gallus

<400> SEQUENCE: 283

Phe Lys Glu Leu Lys Val His His Ala Asn Glu Asn Ile Phe Tyr
1               5                   10                  15

<210> SEQ ID NO 284
<211> LENGTH: 15
<212> TYPE: PRT
<213> ORGANISM: Gallus gallus

<400> SEQUENCE: 284

Leu Lys Val His His Ala Asn Glu Asn Ile Phe Tyr Cys Pro Ile
1               5                   10                  15

<210> SEQ ID NO 285
<211> LENGTH: 15
<212> TYPE: PRT
<213> ORGANISM: Gallus gallus

<400> SEQUENCE: 285

His His Ala Asn Glu Asn Ile Phe Tyr Cys Pro Ile Ala Ile Met
1               5                   10                  15

<210> SEQ ID NO 286
<211> LENGTH: 15
<212> TYPE: PRT
<213> ORGANISM: Gallus gallus

<400> SEQUENCE: 286

Asn Glu Asn Ile Phe Tyr Cys Pro Ile Ala Ile Met Ser Ala Leu
1               5                   10                  15

<210> SEQ ID NO 287
<211> LENGTH: 15
<212> TYPE: PRT
<213> ORGANISM: Gallus gallus

<400> SEQUENCE: 287

Ile Phe Tyr Cys Pro Ile Ala Ile Met Ser Ala Leu Ala Met Val
1               5                   10                  15

<210> SEQ ID NO 288
<211> LENGTH: 15
<212> TYPE: PRT
<213> ORGANISM: Gallus gallus

<400> SEQUENCE: 288

Cys Pro Ile Ala Ile Met Ser Ala Leu Ala Met Val Tyr Leu Gly
1               5                   10                  15

<210> SEQ ID NO 289
<211> LENGTH: 15
<212> TYPE: PRT
<213> ORGANISM: Gallus gallus

<400> SEQUENCE: 289

Ala Ile Met Ser Ala Leu Ala Met Val Tyr Leu Gly Ala Lys Asp
1               5                   10                  15

<210> SEQ ID NO 290
<211> LENGTH: 15
<212> TYPE: PRT
<213> ORGANISM: Gallus gallus

<400> SEQUENCE: 290

Ser Ala Leu Ala Met Val Tyr Leu Gly Ala Lys Asp Ser Thr Arg
1               5                   10                  15

```
<210> SEQ ID NO 291
<211> LENGTH: 15
<212> TYPE: PRT
<213> ORGANISM: Gallus gallus

<400> SEQUENCE: 291

Ala Met Val Tyr Leu Gly Ala Lys Asp Ser Thr Arg Thr Gln Ile
1               5                   10                  15

<210> SEQ ID NO 292
<211> LENGTH: 15
<212> TYPE: PRT
<213> ORGANISM: Gallus gallus

<400> SEQUENCE: 292

Tyr Leu Gly Ala Lys Asp Ser Thr Arg Thr Gln Ile Asn Lys Val
1               5                   10                  15

<210> SEQ ID NO 293
<211> LENGTH: 15
<212> TYPE: PRT
<213> ORGANISM: Gallus gallus

<400> SEQUENCE: 293

Ala Lys Asp Ser Thr Arg Thr Gln Ile Asn Lys Val Val Arg Phe
1               5                   10                  15

<210> SEQ ID NO 294
<211> LENGTH: 15
<212> TYPE: PRT
<213> ORGANISM: Gallus gallus

<400> SEQUENCE: 294

Ser Thr Arg Thr Gln Ile Asn Lys Val Val Arg Phe Asp Lys Leu
1               5                   10                  15

<210> SEQ ID NO 295
<211> LENGTH: 15
<212> TYPE: PRT
<213> ORGANISM: Gallus gallus

<400> SEQUENCE: 295

Thr Gln Ile Asn Lys Val Val Arg Phe Asp Lys Leu Pro Gly Phe
1               5                   10                  15

<210> SEQ ID NO 296
<211> LENGTH: 15
<212> TYPE: PRT
<213> ORGANISM: Gallus gallus

<400> SEQUENCE: 296

Asn Lys Val Val Arg Phe Asp Lys Leu Pro Gly Phe Gly Asp Ser
1               5                   10                  15

<210> SEQ ID NO 297
<211> LENGTH: 15
<212> TYPE: PRT
<213> ORGANISM: Gallus gallus

<400> SEQUENCE: 297

Val Arg Phe Asp Lys Leu Pro Gly Phe Gly Asp Ser Ile Glu Ala
1               5                   10                  15

<210> SEQ ID NO 298
<211> LENGTH: 15
```

```
<212> TYPE: PRT
<213> ORGANISM: Gallus gallus

<400> SEQUENCE: 298

Asp Lys Leu Pro Gly Phe Gly Asp Ser Ile Glu Ala Gln Cys Gly
1               5                   10                  15

<210> SEQ ID NO 299
<211> LENGTH: 15
<212> TYPE: PRT
<213> ORGANISM: Gallus gallus

<400> SEQUENCE: 299

Pro Gly Phe Gly Asp Ser Ile Glu Ala Gln Cys Gly Thr Ser Val
1               5                   10                  15

<210> SEQ ID NO 300
<211> LENGTH: 15
<212> TYPE: PRT
<213> ORGANISM: Gallus gallus

<400> SEQUENCE: 300

Gly Asp Ser Ile Glu Ala Gln Cys Gly Thr Ser Val Asn Val His
1               5                   10                  15

<210> SEQ ID NO 301
<211> LENGTH: 15
<212> TYPE: PRT
<213> ORGANISM: Gallus gallus

<400> SEQUENCE: 301

Ile Glu Ala Gln Cys Gly Thr Ser Val Asn Val His Ser Ser Leu
1               5                   10                  15

<210> SEQ ID NO 302
<211> LENGTH: 15
<212> TYPE: PRT
<213> ORGANISM: Gallus gallus

<400> SEQUENCE: 302

Gln Cys Gly Thr Ser Val Asn Val His Ser Ser Leu Arg Asp Ile
1               5                   10                  15

<210> SEQ ID NO 303
<211> LENGTH: 15
<212> TYPE: PRT
<213> ORGANISM: Gallus gallus

<400> SEQUENCE: 303

Thr Ser Val Asn Val His Ser Ser Leu Arg Asp Ile Leu Asn Gln
1               5                   10                  15

<210> SEQ ID NO 304
<211> LENGTH: 15
<212> TYPE: PRT
<213> ORGANISM: Gallus gallus

<400> SEQUENCE: 304

Asn Val His Ser Ser Leu Arg Asp Ile Leu Asn Gln Ile Thr Lys
1               5                   10                  15

<210> SEQ ID NO 305
<211> LENGTH: 15
<212> TYPE: PRT
<213> ORGANISM: Gallus gallus
```

<400> SEQUENCE: 305

Ser Ser Leu Arg Asp Ile Leu Asn Gln Ile Thr Lys Pro Asn Asp
1               5                   10                  15

<210> SEQ ID NO 306
<211> LENGTH: 15
<212> TYPE: PRT
<213> ORGANISM: Gallus gallus

<400> SEQUENCE: 306

Arg Asp Ile Leu Asn Gln Ile Thr Lys Pro Asn Asp Val Tyr Ser
1               5                   10                  15

<210> SEQ ID NO 307
<211> LENGTH: 15
<212> TYPE: PRT
<213> ORGANISM: Gallus gallus

<400> SEQUENCE: 307

Leu Asn Gln Ile Thr Lys Pro Asn Asp Val Tyr Ser Phe Ser Leu
1               5                   10                  15

<210> SEQ ID NO 308
<211> LENGTH: 15
<212> TYPE: PRT
<213> ORGANISM: Gallus gallus

<400> SEQUENCE: 308

Ile Thr Lys Pro Asn Asp Val Tyr Ser Phe Ser Leu Ala Ser Arg
1               5                   10                  15

<210> SEQ ID NO 309
<211> LENGTH: 15
<212> TYPE: PRT
<213> ORGANISM: Gallus gallus

<400> SEQUENCE: 309

Pro Asn Asp Val Tyr Ser Phe Ser Leu Ala Ser Arg Leu Tyr Ala
1               5                   10                  15

<210> SEQ ID NO 310
<211> LENGTH: 15
<212> TYPE: PRT
<213> ORGANISM: Gallus gallus

<400> SEQUENCE: 310

Val Tyr Ser Phe Ser Leu Ala Ser Arg Leu Tyr Ala Glu Glu Arg
1               5                   10                  15

<210> SEQ ID NO 311
<211> LENGTH: 15
<212> TYPE: PRT
<213> ORGANISM: Gallus gallus

<400> SEQUENCE: 311

Phe Ser Leu Ala Ser Arg Leu Tyr Ala Glu Glu Arg Tyr Pro Ile
1               5                   10                  15

<210> SEQ ID NO 312
<211> LENGTH: 15
<212> TYPE: PRT
<213> ORGANISM: Gallus gallus

<400> SEQUENCE: 312

Ala Ser Arg Leu Tyr Ala Glu Glu Arg Tyr Pro Ile Leu Pro Glu
1               5                   10                  15

<210> SEQ ID NO 313
<211> LENGTH: 15
<212> TYPE: PRT
<213> ORGANISM: Gallus gallus

<400> SEQUENCE: 313

Leu Tyr Ala Glu Glu Arg Tyr Pro Ile Leu Pro Glu Tyr Leu Gln
1               5                   10                  15

<210> SEQ ID NO 314
<211> LENGTH: 15
<212> TYPE: PRT
<213> ORGANISM: Gallus gallus

<400> SEQUENCE: 314

Glu Glu Arg Tyr Pro Ile Leu Pro Glu Tyr Leu Gln Cys Val Lys
1               5                   10                  15

<210> SEQ ID NO 315
<211> LENGTH: 15
<212> TYPE: PRT
<213> ORGANISM: Gallus gallus

<400> SEQUENCE: 315

Tyr Pro Ile Leu Pro Glu Tyr Leu Gln Cys Val Lys Glu Leu Tyr
1               5                   10                  15

<210> SEQ ID NO 316
<211> LENGTH: 15
<212> TYPE: PRT
<213> ORGANISM: Gallus gallus

<400> SEQUENCE: 316

Leu Pro Glu Tyr Leu Gln Cys Val Lys Glu Leu Tyr Arg Gly Gly
1               5                   10                  15

<210> SEQ ID NO 317
<211> LENGTH: 15
<212> TYPE: PRT
<213> ORGANISM: Gallus gallus

<400> SEQUENCE: 317

Tyr Leu Gln Cys Val Lys Glu Leu Tyr Arg Gly Gly Leu Glu Pro
1               5                   10                  15

<210> SEQ ID NO 318
<211> LENGTH: 15
<212> TYPE: PRT
<213> ORGANISM: Gallus gallus

<400> SEQUENCE: 318

Cys Val Lys Glu Leu Tyr Arg Gly Gly Leu Glu Pro Ile Asn Phe
1               5                   10                  15

<210> SEQ ID NO 319
<211> LENGTH: 15
<212> TYPE: PRT
<213> ORGANISM: Gallus gallus

<400> SEQUENCE: 319

Glu Leu Tyr Arg Gly Gly Leu Glu Pro Ile Asn Phe Gln Thr Ala

<210> SEQ ID NO 320
<211> LENGTH: 15
<212> TYPE: PRT
<213> ORGANISM: Gallus gallus

<400> SEQUENCE: 320

Arg Gly Gly Leu Glu Pro Ile Asn Phe Gln Thr Ala Ala Asp Gln
1               5                   10                  15

<210> SEQ ID NO 321
<211> LENGTH: 15
<212> TYPE: PRT
<213> ORGANISM: Gallus gallus

<400> SEQUENCE: 321

Leu Glu Pro Ile Asn Phe Gln Thr Ala Ala Asp Gln Ala Arg Glu
1               5                   10                  15

<210> SEQ ID NO 322
<211> LENGTH: 15
<212> TYPE: PRT
<213> ORGANISM: Gallus gallus

<400> SEQUENCE: 322

Ile Asn Phe Gln Thr Ala Ala Asp Gln Ala Arg Glu Leu Ile Asn
1               5                   10                  15

<210> SEQ ID NO 323
<211> LENGTH: 15
<212> TYPE: PRT
<213> ORGANISM: Gallus gallus

<400> SEQUENCE: 323

Gln Thr Ala Ala Asp Gln Ala Arg Glu Leu Ile Asn Ser Trp Val
1               5                   10                  15

<210> SEQ ID NO 324
<211> LENGTH: 15
<212> TYPE: PRT
<213> ORGANISM: Gallus gallus

<400> SEQUENCE: 324

Ala Asp Gln Ala Arg Glu Leu Ile Asn Ser Trp Val Glu Ser Gln
1               5                   10                  15

<210> SEQ ID NO 325
<211> LENGTH: 15
<212> TYPE: PRT
<213> ORGANISM: Gallus gallus

<400> SEQUENCE: 325

Ala Arg Glu Leu Ile Asn Ser Trp Val Glu Ser Gln Thr Asn Gly
1               5                   10                  15

<210> SEQ ID NO 326
<211> LENGTH: 15
<212> TYPE: PRT
<213> ORGANISM: Gallus gallus

<400> SEQUENCE: 326

Leu Ile Asn Ser Trp Val Glu Ser Gln Thr Asn Gly Ile Ile Arg
1               5                   10                  15

<210> SEQ ID NO 327
<211> LENGTH: 15
<212> TYPE: PRT
<213> ORGANISM: Gallus gallus

<400> SEQUENCE: 327

Ser Trp Val Glu Ser Gln Thr Asn Gly Ile Ile Arg Asn Val Leu
1               5                   10                  15

<210> SEQ ID NO 328
<211> LENGTH: 15
<212> TYPE: PRT
<213> ORGANISM: Gallus gallus

<400> SEQUENCE: 328

Glu Ser Gln Thr Asn Gly Ile Ile Arg Asn Val Leu Gln Pro Ser
1               5                   10                  15

<210> SEQ ID NO 329
<211> LENGTH: 15
<212> TYPE: PRT
<213> ORGANISM: Gallus gallus

<400> SEQUENCE: 329

Thr Asn Gly Ile Ile Arg Asn Val Leu Gln Pro Ser Ser Val Asp
1               5                   10                  15

<210> SEQ ID NO 330
<211> LENGTH: 15
<212> TYPE: PRT
<213> ORGANISM: Gallus gallus

<400> SEQUENCE: 330

Ile Ile Arg Asn Val Leu Gln Pro Ser Ser Val Asp Ser Gln Thr
1               5                   10                  15

<210> SEQ ID NO 331
<211> LENGTH: 15
<212> TYPE: PRT
<213> ORGANISM: Gallus gallus

<400> SEQUENCE: 331

Asn Val Leu Gln Pro Ser Ser Val Asp Ser Gln Thr Ala Met Val
1               5                   10                  15

<210> SEQ ID NO 332
<211> LENGTH: 15
<212> TYPE: PRT
<213> ORGANISM: Gallus gallus

<400> SEQUENCE: 332

Gln Pro Ser Ser Val Asp Ser Gln Thr Ala Met Val Leu Val Asn
1               5                   10                  15

<210> SEQ ID NO 333
<211> LENGTH: 15
<212> TYPE: PRT
<213> ORGANISM: Gallus gallus

<400> SEQUENCE: 333

Ser Val Asp Ser Gln Thr Ala Met Val Leu Val Asn Ala Ile Val
1               5                   10                  15

<210> SEQ ID NO 334

```
<211> LENGTH: 15
<212> TYPE: PRT
<213> ORGANISM: Gallus gallus

<400> SEQUENCE: 334

Ser Gln Thr Ala Met Val Leu Val Asn Ala Ile Val Phe Lys Gly
1               5                   10                  15

<210> SEQ ID NO 335
<211> LENGTH: 15
<212> TYPE: PRT
<213> ORGANISM: Gallus gallus

<400> SEQUENCE: 335

Ala Met Val Leu Val Asn Ala Ile Val Phe Lys Gly Leu Trp Glu
1               5                   10                  15

<210> SEQ ID NO 336
<211> LENGTH: 15
<212> TYPE: PRT
<213> ORGANISM: Gallus gallus

<400> SEQUENCE: 336

Leu Val Asn Ala Ile Val Phe Lys Gly Leu Trp Glu Lys Ala Phe
1               5                   10                  15

<210> SEQ ID NO 337
<211> LENGTH: 15
<212> TYPE: PRT
<213> ORGANISM: Gallus gallus

<400> SEQUENCE: 337

Ala Ile Val Phe Lys Gly Leu Trp Glu Lys Ala Phe Lys Asp Glu
1               5                   10                  15

<210> SEQ ID NO 338
<211> LENGTH: 15
<212> TYPE: PRT
<213> ORGANISM: Gallus gallus

<400> SEQUENCE: 338

Phe Lys Gly Leu Trp Glu Lys Ala Phe Lys Asp Glu Asp Thr Gln
1               5                   10                  15

<210> SEQ ID NO 339
<211> LENGTH: 15
<212> TYPE: PRT
<213> ORGANISM: Gallus gallus

<400> SEQUENCE: 339

Leu Trp Glu Lys Ala Phe Lys Asp Glu Asp Thr Gln Ala Met Pro
1               5                   10                  15

<210> SEQ ID NO 340
<211> LENGTH: 15
<212> TYPE: PRT
<213> ORGANISM: Gallus gallus

<400> SEQUENCE: 340

Lys Ala Phe Lys Asp Glu Asp Thr Gln Ala Met Pro Phe Arg Val
1               5                   10                  15

<210> SEQ ID NO 341
<211> LENGTH: 15
<212> TYPE: PRT
```

<213> ORGANISM: Gallus gallus

<400> SEQUENCE: 341

Lys Asp Glu Asp Thr Gln Ala Met Pro Phe Arg Val Thr Glu Gln
1               5                   10                  15

<210> SEQ ID NO 342
<211> LENGTH: 15
<212> TYPE: PRT
<213> ORGANISM: Gallus gallus

<400> SEQUENCE: 342

Asp Thr Gln Ala Met Pro Phe Arg Val Thr Glu Gln Glu Ser Lys
1               5                   10                  15

<210> SEQ ID NO 343
<211> LENGTH: 15
<212> TYPE: PRT
<213> ORGANISM: Gallus gallus

<400> SEQUENCE: 343

Ala Met Pro Phe Arg Val Thr Glu Gln Glu Ser Lys Pro Val Gln
1               5                   10                  15

<210> SEQ ID NO 344
<211> LENGTH: 15
<212> TYPE: PRT
<213> ORGANISM: Gallus gallus

<400> SEQUENCE: 344

Phe Arg Val Thr Glu Gln Glu Ser Lys Pro Val Gln Met Met Tyr
1               5                   10                  15

<210> SEQ ID NO 345
<211> LENGTH: 15
<212> TYPE: PRT
<213> ORGANISM: Gallus gallus

<400> SEQUENCE: 345

Thr Glu Gln Glu Ser Lys Pro Val Gln Met Met Tyr Gln Ile Gly
1               5                   10                  15

<210> SEQ ID NO 346
<211> LENGTH: 15
<212> TYPE: PRT
<213> ORGANISM: Gallus gallus

<400> SEQUENCE: 346

Glu Ser Lys Pro Val Gln Met Met Tyr Gln Ile Gly Leu Phe Arg
1               5                   10                  15

<210> SEQ ID NO 347
<211> LENGTH: 15
<212> TYPE: PRT
<213> ORGANISM: Gallus gallus

<400> SEQUENCE: 347

Pro Val Gln Met Met Tyr Gln Ile Gly Leu Phe Arg Val Ala Ser
1               5                   10                  15

<210> SEQ ID NO 348
<211> LENGTH: 15
<212> TYPE: PRT
<213> ORGANISM: Gallus gallus -continued

<400> SEQUENCE: 348

Met Met Tyr Gln Ile Gly Leu Phe Arg Val Ala Ser Met Ala Ser
1               5                   10                  15

<210> SEQ ID NO 349
<211> LENGTH: 15
<212> TYPE: PRT
<213> ORGANISM: Gallus gallus

<400> SEQUENCE: 349

Gln Ile Gly Leu Phe Arg Val Ala Ser Met Ala Ser Glu Lys Met
1               5                   10                  15

<210> SEQ ID NO 350
<211> LENGTH: 15
<212> TYPE: PRT
<213> ORGANISM: Gallus gallus

<400> SEQUENCE: 350

Leu Phe Arg Val Ala Ser Met Ala Ser Glu Lys Met Lys Ile Leu
1               5                   10                  15

<210> SEQ ID NO 351
<211> LENGTH: 15
<212> TYPE: PRT
<213> ORGANISM: Gallus gallus

<400> SEQUENCE: 351

Val Ala Ser Met Ala Ser Glu Lys Met Lys Ile Leu Glu Leu Pro
1               5                   10                  15

<210> SEQ ID NO 352
<211> LENGTH: 15
<212> TYPE: PRT
<213> ORGANISM: Gallus gallus

<400> SEQUENCE: 352

Met Ala Ser Glu Lys Met Lys Ile Leu Glu Leu Pro Phe Ala Ser
1               5                   10                  15

<210> SEQ ID NO 353
<211> LENGTH: 15
<212> TYPE: PRT
<213> ORGANISM: Gallus gallus

<400> SEQUENCE: 353

Glu Lys Met Lys Ile Leu Glu Leu Pro Phe Ala Ser Gly Thr Met
1               5                   10                  15

<210> SEQ ID NO 354
<211> LENGTH: 15
<212> TYPE: PRT
<213> ORGANISM: Gallus gallus

<400> SEQUENCE: 354

Lys Ile Leu Glu Leu Pro Phe Ala Ser Gly Thr Met Ser Met Leu
1               5                   10                  15

<210> SEQ ID NO 355
<211> LENGTH: 15
<212> TYPE: PRT
<213> ORGANISM: Gallus gallus

<400> SEQUENCE: 355

```
Glu Leu Pro Phe Ala Ser Gly Thr Met Ser Met Leu Val Leu Leu
1               5                   10                  15
```

<210> SEQ ID NO 356
<211> LENGTH: 15
<212> TYPE: PRT
<213> ORGANISM: Gallus gallus

<400> SEQUENCE: 356

```
Phe Ala Ser Gly Thr Met Ser Met Leu Val Leu Leu Pro Asp Glu
1               5                   10                  15
```

<210> SEQ ID NO 357
<211> LENGTH: 15
<212> TYPE: PRT
<213> ORGANISM: Gallus gallus

<400> SEQUENCE: 357

```
Gly Thr Met Ser Met Leu Val Leu Leu Pro Asp Glu Val Ser Gly
1               5                   10                  15
```

<210> SEQ ID NO 358
<211> LENGTH: 15
<212> TYPE: PRT
<213> ORGANISM: Gallus gallus

<400> SEQUENCE: 358

```
Ser Met Leu Val Leu Leu Pro Asp Glu Val Ser Gly Leu Glu Gln
1               5                   10                  15
```

<210> SEQ ID NO 359
<211> LENGTH: 15
<212> TYPE: PRT
<213> ORGANISM: Gallus gallus

<400> SEQUENCE: 359

```
Val Leu Leu Pro Asp Glu Val Ser Gly Leu Glu Gln Leu Glu Ser
1               5                   10                  15
```

<210> SEQ ID NO 360
<211> LENGTH: 15
<212> TYPE: PRT
<213> ORGANISM: Gallus gallus

<400> SEQUENCE: 360

```
Pro Asp Glu Val Ser Gly Leu Glu Gln Leu Glu Ser Ile Ile Asn
1               5                   10                  15
```

<210> SEQ ID NO 361
<211> LENGTH: 15
<212> TYPE: PRT
<213> ORGANISM: Gallus gallus

<400> SEQUENCE: 361

```
Val Ser Gly Leu Glu Gln Leu Glu Ser Ile Ile Asn Phe Glu Lys
1               5                   10                  15
```

<210> SEQ ID NO 362
<211> LENGTH: 15
<212> TYPE: PRT
<213> ORGANISM: Gallus gallus

<400> SEQUENCE: 362

```
Leu Glu Gln Leu Glu Ser Ile Ile Asn Phe Glu Lys Leu Thr Glu
1               5                   10                  15
```

-continued

<210> SEQ ID NO 363
<211> LENGTH: 15
<212> TYPE: PRT
<213> ORGANISM: Gallus gallus

<400> SEQUENCE: 363

Leu Glu Ser Ile Ile Asn Phe Glu Lys Leu Thr Glu Trp Thr Ser
1               5                   10                  15

<210> SEQ ID NO 364
<211> LENGTH: 15
<212> TYPE: PRT
<213> ORGANISM: Gallus gallus

<400> SEQUENCE: 364

Ile Ile Asn Phe Glu Lys Leu Thr Glu Trp Thr Ser Ser Asn Val
1               5                   10                  15

<210> SEQ ID NO 365
<211> LENGTH: 15
<212> TYPE: PRT
<213> ORGANISM: Gallus gallus

<400> SEQUENCE: 365

Phe Glu Lys Leu Thr Glu Trp Thr Ser Ser Asn Val Met Glu Glu
1               5                   10                  15

<210> SEQ ID NO 366
<211> LENGTH: 15
<212> TYPE: PRT
<213> ORGANISM: Gallus gallus

<400> SEQUENCE: 366

Leu Thr Glu Trp Thr Ser Ser Asn Val Met Glu Glu Arg Lys Ile
1               5                   10                  15

<210> SEQ ID NO 367
<211> LENGTH: 15
<212> TYPE: PRT
<213> ORGANISM: Gallus gallus

<400> SEQUENCE: 367

Trp Thr Ser Ser Asn Val Met Glu Glu Arg Lys Ile Lys Val Tyr
1               5                   10                  15

<210> SEQ ID NO 368
<211> LENGTH: 15
<212> TYPE: PRT
<213> ORGANISM: Gallus gallus

<400> SEQUENCE: 368

Ser Asn Val Met Glu Glu Arg Lys Ile Lys Val Tyr Leu Pro Arg
1               5                   10                  15

<210> SEQ ID NO 369
<211> LENGTH: 15
<212> TYPE: PRT
<213> ORGANISM: Gallus gallus

<400> SEQUENCE: 369

Met Glu Glu Arg Lys Ile Lys Val Tyr Leu Pro Arg Met Lys Met
1               5                   10                  15

```
<210> SEQ ID NO 370
<211> LENGTH: 15
<212> TYPE: PRT
<213> ORGANISM: Gallus gallus

<400> SEQUENCE: 370

Arg Lys Ile Lys Val Tyr Leu Pro Arg Met Lys Met Glu Glu Lys
1               5                   10                  15

<210> SEQ ID NO 371
<211> LENGTH: 15
<212> TYPE: PRT
<213> ORGANISM: Gallus gallus

<400> SEQUENCE: 371

Lys Val Tyr Leu Pro Arg Met Lys Met Glu Glu Lys Tyr Asn Leu
1               5                   10                  15

<210> SEQ ID NO 372
<211> LENGTH: 15
<212> TYPE: PRT
<213> ORGANISM: Gallus gallus

<400> SEQUENCE: 372

Leu Pro Arg Met Lys Met Glu Glu Lys Tyr Asn Leu Thr Ser Val
1               5                   10                  15

<210> SEQ ID NO 373
<211> LENGTH: 15
<212> TYPE: PRT
<213> ORGANISM: Gallus gallus

<400> SEQUENCE: 373

Met Lys Met Glu Glu Lys Tyr Asn Leu Thr Ser Val Leu Met Ala
1               5                   10                  15

<210> SEQ ID NO 374
<211> LENGTH: 15
<212> TYPE: PRT
<213> ORGANISM: Gallus gallus

<400> SEQUENCE: 374

Glu Glu Lys Tyr Asn Leu Thr Ser Val Leu Met Ala Met Gly Ile
1               5                   10                  15

<210> SEQ ID NO 375
<211> LENGTH: 15
<212> TYPE: PRT
<213> ORGANISM: Gallus gallus

<400> SEQUENCE: 375

Tyr Asn Leu Thr Ser Val Leu Met Ala Met Gly Ile Thr Asp Val
1               5                   10                  15

<210> SEQ ID NO 376
<211> LENGTH: 15
<212> TYPE: PRT
<213> ORGANISM: Gallus gallus

<400> SEQUENCE: 376

Thr Ser Val Leu Met Ala Met Gly Ile Thr Asp Val Phe Ser Ser
1               5                   10                  15

<210> SEQ ID NO 377
<211> LENGTH: 15
```

```
<212> TYPE: PRT
<213> ORGANISM: Gallus gallus

<400> SEQUENCE: 377

Leu Met Ala Met Gly Ile Thr Asp Val Phe Ser Ser Ser Ala Asn
1               5                   10                  15

<210> SEQ ID NO 378
<211> LENGTH: 15
<212> TYPE: PRT
<213> ORGANISM: Gallus gallus

<400> SEQUENCE: 378

Met Gly Ile Thr Asp Val Phe Ser Ser Ser Ala Asn Leu Ser Gly
1               5                   10                  15

<210> SEQ ID NO 379
<211> LENGTH: 15
<212> TYPE: PRT
<213> ORGANISM: Gallus gallus

<400> SEQUENCE: 379

Thr Asp Val Phe Ser Ser Ser Ala Asn Leu Ser Gly Ile Ser Ser
1               5                   10                  15

<210> SEQ ID NO 380
<211> LENGTH: 15
<212> TYPE: PRT
<213> ORGANISM: Gallus gallus

<400> SEQUENCE: 380

Phe Ser Ser Ser Ala Asn Leu Ser Gly Ile Ser Ser Ala Glu Ser
1               5                   10                  15

<210> SEQ ID NO 381
<211> LENGTH: 15
<212> TYPE: PRT
<213> ORGANISM: Gallus gallus

<400> SEQUENCE: 381

Ser Ala Asn Leu Ser Gly Ile Ser Ser Ala Glu Ser Leu Lys Ile
1               5                   10                  15

<210> SEQ ID NO 382
<211> LENGTH: 15
<212> TYPE: PRT
<213> ORGANISM: Gallus gallus

<400> SEQUENCE: 382

Leu Ser Gly Ile Ser Ser Ala Glu Ser Leu Lys Ile Ser Gln Ala
1               5                   10                  15

<210> SEQ ID NO 383
<211> LENGTH: 15
<212> TYPE: PRT
<213> ORGANISM: Gallus gallus

<400> SEQUENCE: 383

Ile Ser Ser Ala Glu Ser Leu Lys Ile Ser Gln Ala Val His Ala
1               5                   10                  15

<210> SEQ ID NO 384
<211> LENGTH: 15
<212> TYPE: PRT
<213> ORGANISM: Gallus gallus
```

-continued

```
<400> SEQUENCE: 384

Ala Glu Ser Leu Lys Ile Ser Gln Ala Val His Ala Ala His Ala
1               5                   10                  15

<210> SEQ ID NO 385
<211> LENGTH: 15
<212> TYPE: PRT
<213> ORGANISM: Gallus gallus

<400> SEQUENCE: 385

Leu Lys Ile Ser Gln Ala Val His Ala Ala His Ala Glu Ile Asn
1               5                   10                  15

<210> SEQ ID NO 386
<211> LENGTH: 15
<212> TYPE: PRT
<213> ORGANISM: Gallus gallus

<400> SEQUENCE: 386

Ser Gln Ala Val His Ala Ala His Ala Glu Ile Asn Glu Ala Gly
1               5                   10                  15

<210> SEQ ID NO 387
<211> LENGTH: 15
<212> TYPE: PRT
<213> ORGANISM: Gallus gallus

<400> SEQUENCE: 387

Val His Ala Ala His Ala Glu Ile Asn Glu Ala Gly Arg Glu Val
1               5                   10                  15

<210> SEQ ID NO 388
<211> LENGTH: 15
<212> TYPE: PRT
<213> ORGANISM: Gallus gallus

<400> SEQUENCE: 388

Ala His Ala Glu Ile Asn Glu Ala Gly Arg Glu Val Val Gly Ser
1               5                   10                  15

<210> SEQ ID NO 389
<211> LENGTH: 15
<212> TYPE: PRT
<213> ORGANISM: Gallus gallus

<400> SEQUENCE: 389

Glu Ile Asn Glu Ala Gly Arg Glu Val Val Gly Ser Ala Glu Ala
1               5                   10                  15

<210> SEQ ID NO 390
<211> LENGTH: 15
<212> TYPE: PRT
<213> ORGANISM: Gallus gallus

<400> SEQUENCE: 390

Glu Ala Gly Arg Glu Val Val Gly Ser Ala Glu Ala Gly Val Asp
1               5                   10                  15

<210> SEQ ID NO 391
<211> LENGTH: 15
<212> TYPE: PRT
<213> ORGANISM: Gallus gallus

<400> SEQUENCE: 391
```

Arg Glu Val Val Gly Ser Ala Glu Ala Gly Val Asp Ala Ala Ser
1               5                   10                  15

<210> SEQ ID NO 392
<211> LENGTH: 15
<212> TYPE: PRT
<213> ORGANISM: Gallus gallus

<400> SEQUENCE: 392

Val Gly Ser Ala Glu Ala Gly Val Asp Ala Ala Ser Val Ser Glu
1               5                   10                  15

<210> SEQ ID NO 393
<211> LENGTH: 15
<212> TYPE: PRT
<213> ORGANISM: Gallus gallus

<400> SEQUENCE: 393

Ala Glu Ala Gly Val Asp Ala Ala Ser Val Ser Glu Glu Phe Arg
1               5                   10                  15

<210> SEQ ID NO 394
<211> LENGTH: 15
<212> TYPE: PRT
<213> ORGANISM: Gallus gallus

<400> SEQUENCE: 394

Gly Val Asp Ala Ala Ser Val Ser Glu Glu Phe Arg Ala Asp His
1               5                   10                  15

<210> SEQ ID NO 395
<211> LENGTH: 15
<212> TYPE: PRT
<213> ORGANISM: Gallus gallus

<400> SEQUENCE: 395

Ala Ala Ser Val Ser Glu Glu Phe Arg Ala Asp His Pro Phe Leu
1               5                   10                  15

<210> SEQ ID NO 396
<211> LENGTH: 15
<212> TYPE: PRT
<213> ORGANISM: Gallus gallus

<400> SEQUENCE: 396

Val Ser Glu Glu Phe Arg Ala Asp His Pro Phe Leu Phe Cys Ile
1               5                   10                  15

<210> SEQ ID NO 397
<211> LENGTH: 15
<212> TYPE: PRT
<213> ORGANISM: Gallus gallus

<400> SEQUENCE: 397

Glu Phe Arg Ala Asp His Pro Phe Leu Phe Cys Ile Lys His Ile
1               5                   10                  15

<210> SEQ ID NO 398
<211> LENGTH: 15
<212> TYPE: PRT
<213> ORGANISM: Gallus gallus

<400> SEQUENCE: 398

Ala Asp His Pro Phe Leu Phe Cys Ile Lys His Ile Ala Thr Asn

<210> SEQ ID NO 399
<211> LENGTH: 15
<212> TYPE: PRT
<213> ORGANISM: Gallus gallus

<400> SEQUENCE: 399

Pro Phe Leu Phe Cys Ile Lys His Ile Ala Thr Asn Ala Val Leu
1               5                   10                  15

<210> SEQ ID NO 400
<211> LENGTH: 15
<212> TYPE: PRT
<213> ORGANISM: Gallus gallus

<400> SEQUENCE: 400

Phe Cys Ile Lys His Ile Ala Thr Asn Ala Val Leu Phe Phe Gly
1               5                   10                  15

<210> SEQ ID NO 401
<211> LENGTH: 15
<212> TYPE: PRT
<213> ORGANISM: Gallus gallus

<400> SEQUENCE: 401

Lys His Ile Ala Thr Asn Ala Val Leu Phe Phe Gly Arg Cys Val
1               5                   10                  15

<210> SEQ ID NO 402
<211> LENGTH: 14
<212> TYPE: PRT
<213> ORGANISM: Gallus gallus

<400> SEQUENCE: 402

Ala Thr Asn Ala Val Leu Phe Phe Gly Arg Cys Val Ser Pro
1               5                   10

<210> SEQ ID NO 403
<211> LENGTH: 15
<212> TYPE: PRT
<213> ORGANISM: Gallus gallus

<400> SEQUENCE: 403

Ala Glu Val Asp Cys Ser Arg Phe Pro Asn Ala Thr Asp Lys Glu
1               5                   10                  15

<210> SEQ ID NO 404
<211> LENGTH: 15
<212> TYPE: PRT
<213> ORGANISM: Gallus gallus

<400> SEQUENCE: 404

Asp Cys Ser Arg Phe Pro Asn Ala Thr Asp Lys Glu Gly Lys Asp
1               5                   10                  15

<210> SEQ ID NO 405
<211> LENGTH: 15
<212> TYPE: PRT
<213> ORGANISM: Gallus gallus

<400> SEQUENCE: 405

Arg Phe Pro Asn Ala Thr Asp Lys Glu Gly Lys Asp Val Leu Val
1               5                   10                  15

```
<210> SEQ ID NO 406
<211> LENGTH: 15
<212> TYPE: PRT
<213> ORGANISM: Gallus gallus

<400> SEQUENCE: 406

Asn Ala Thr Asp Lys Glu Gly Lys Asp Val Leu Val Cys Asn Lys
1               5                   10                  15

<210> SEQ ID NO 407
<211> LENGTH: 15
<212> TYPE: PRT
<213> ORGANISM: Gallus gallus

<400> SEQUENCE: 407

Asp Lys Glu Gly Lys Asp Val Leu Val Cys Asn Lys Asp Leu Arg
1               5                   10                  15

<210> SEQ ID NO 408
<211> LENGTH: 15
<212> TYPE: PRT
<213> ORGANISM: Gallus gallus

<400> SEQUENCE: 408

Gly Lys Asp Val Leu Val Cys Asn Lys Asp Leu Arg Pro Ile Cys
1               5                   10                  15

<210> SEQ ID NO 409
<211> LENGTH: 15
<212> TYPE: PRT
<213> ORGANISM: Gallus gallus

<400> SEQUENCE: 409

Val Leu Val Cys Asn Lys Asp Leu Arg Pro Ile Cys Gly Thr Asp
1               5                   10                  15

<210> SEQ ID NO 410
<211> LENGTH: 15
<212> TYPE: PRT
<213> ORGANISM: Gallus gallus

<400> SEQUENCE: 410

Cys Asn Lys Asp Leu Arg Pro Ile Cys Gly Thr Asp Gly Val Thr
1               5                   10                  15

<210> SEQ ID NO 411
<211> LENGTH: 15
<212> TYPE: PRT
<213> ORGANISM: Gallus gallus

<400> SEQUENCE: 411

Asp Leu Arg Pro Ile Cys Gly Thr Asp Gly Val Thr Tyr Thr Asn
1               5                   10                  15

<210> SEQ ID NO 412
<211> LENGTH: 15
<212> TYPE: PRT
<213> ORGANISM: Gallus gallus

<400> SEQUENCE: 412

Pro Ile Cys Gly Thr Asp Gly Val Thr Tyr Thr Asn Asp Cys Leu
1               5                   10                  15

<210> SEQ ID NO 413
```

```
<211> LENGTH: 15
<212> TYPE: PRT
<213> ORGANISM: Gallus gallus

<400> SEQUENCE: 413

Gly Thr Asp Gly Val Thr Tyr Thr Asn Asp Cys Leu Leu Cys Ala
1               5                   10                  15

<210> SEQ ID NO 414
<211> LENGTH: 15
<212> TYPE: PRT
<213> ORGANISM: Gallus gallus

<400> SEQUENCE: 414

Gly Val Thr Tyr Thr Asn Asp Cys Leu Leu Cys Ala Tyr Ser Ile
1               5                   10                  15

<210> SEQ ID NO 415
<211> LENGTH: 15
<212> TYPE: PRT
<213> ORGANISM: Gallus gallus

<400> SEQUENCE: 415

Tyr Thr Asn Asp Cys Leu Leu Cys Ala Tyr Ser Ile Glu Phe Gly
1               5                   10                  15

<210> SEQ ID NO 416
<211> LENGTH: 15
<212> TYPE: PRT
<213> ORGANISM: Gallus gallus

<400> SEQUENCE: 416

Asp Cys Leu Leu Cys Ala Tyr Ser Ile Glu Phe Gly Thr Asn Ile
1               5                   10                  15

<210> SEQ ID NO 417
<211> LENGTH: 15
<212> TYPE: PRT
<213> ORGANISM: Gallus gallus

<400> SEQUENCE: 417

Leu Cys Ala Tyr Ser Ile Glu Phe Gly Thr Asn Ile Ser Lys Glu
1               5                   10                  15

<210> SEQ ID NO 418
<211> LENGTH: 15
<212> TYPE: PRT
<213> ORGANISM: Gallus gallus

<400> SEQUENCE: 418

Tyr Ser Ile Glu Phe Gly Thr Asn Ile Ser Lys Glu His Asp Gly
1               5                   10                  15

<210> SEQ ID NO 419
<211> LENGTH: 15
<212> TYPE: PRT
<213> ORGANISM: Gallus gallus

<400> SEQUENCE: 419

Glu Phe Gly Thr Asn Ile Ser Lys Glu His Asp Gly Glu Cys Lys
1               5                   10                  15

<210> SEQ ID NO 420
<211> LENGTH: 15
<212> TYPE: PRT
```

<213> ORGANISM: Gallus gallus

<400> SEQUENCE: 420

Thr Asn Ile Ser Lys Glu His Asp Gly Glu Cys Lys Glu Thr Val
1               5                   10                  15

<210> SEQ ID NO 421
<211> LENGTH: 15
<212> TYPE: PRT
<213> ORGANISM: Gallus gallus

<400> SEQUENCE: 421

Ser Lys Glu His Asp Gly Glu Cys Lys Glu Thr Val Pro Met Asn
1               5                   10                  15

<210> SEQ ID NO 422
<211> LENGTH: 15
<212> TYPE: PRT
<213> ORGANISM: Gallus gallus

<400> SEQUENCE: 422

His Asp Gly Glu Cys Lys Glu Thr Val Pro Met Asn Cys Ser Ser
1               5                   10                  15

<210> SEQ ID NO 423
<211> LENGTH: 15
<212> TYPE: PRT
<213> ORGANISM: Gallus gallus

<400> SEQUENCE: 423

Glu Cys Lys Glu Thr Val Pro Met Asn Cys Ser Ser Tyr Ala Asn
1               5                   10                  15

<210> SEQ ID NO 424
<211> LENGTH: 15
<212> TYPE: PRT
<213> ORGANISM: Gallus gallus

<400> SEQUENCE: 424

Glu Thr Val Pro Met Asn Cys Ser Ser Tyr Ala Asn Thr Thr Ser
1               5                   10                  15

<210> SEQ ID NO 425
<211> LENGTH: 15
<212> TYPE: PRT
<213> ORGANISM: Gallus gallus

<400> SEQUENCE: 425

Pro Met Asn Cys Ser Ser Tyr Ala Asn Thr Thr Ser Glu Asp Gly
1               5                   10                  15

<210> SEQ ID NO 426
<211> LENGTH: 15
<212> TYPE: PRT
<213> ORGANISM: Gallus gallus

<400> SEQUENCE: 426

Cys Ser Ser Tyr Ala Asn Thr Thr Ser Glu Asp Gly Lys Val Met
1               5                   10                  15

<210> SEQ ID NO 427
<211> LENGTH: 15
<212> TYPE: PRT
<213> ORGANISM: Gallus gallus

<400> SEQUENCE: 427

Tyr Ala Asn Thr Thr Ser Glu Asp Gly Lys Val Met Val Leu Cys
1               5                   10                  15

<210> SEQ ID NO 428
<211> LENGTH: 15
<212> TYPE: PRT
<213> ORGANISM: Gallus gallus

<400> SEQUENCE: 428

Thr Thr Ser Glu Asp Gly Lys Val Met Val Leu Cys Asn Arg Ala
1               5                   10                  15

<210> SEQ ID NO 429
<211> LENGTH: 15
<212> TYPE: PRT
<213> ORGANISM: Gallus gallus

<400> SEQUENCE: 429

Glu Asp Gly Lys Val Met Val Leu Cys Asn Arg Ala Phe Asn Pro
1               5                   10                  15

<210> SEQ ID NO 430
<211> LENGTH: 15
<212> TYPE: PRT
<213> ORGANISM: Gallus gallus

<400> SEQUENCE: 430

Lys Val Met Val Leu Cys Asn Arg Ala Phe Asn Pro Val Cys Gly
1               5                   10                  15

<210> SEQ ID NO 431
<211> LENGTH: 15
<212> TYPE: PRT
<213> ORGANISM: Gallus gallus

<400> SEQUENCE: 431

Val Leu Cys Asn Arg Ala Phe Asn Pro Val Cys Gly Thr Asp Gly
1               5                   10                  15

<210> SEQ ID NO 432
<211> LENGTH: 15
<212> TYPE: PRT
<213> ORGANISM: Gallus gallus

<400> SEQUENCE: 432

Asn Arg Ala Phe Asn Pro Val Cys Gly Thr Asp Gly Val Thr Tyr
1               5                   10                  15

<210> SEQ ID NO 433
<211> LENGTH: 15
<212> TYPE: PRT
<213> ORGANISM: Gallus gallus

<400> SEQUENCE: 433

Phe Asn Pro Val Cys Gly Thr Asp Gly Val Thr Tyr Asp Asn Glu
1               5                   10                  15

<210> SEQ ID NO 434
<211> LENGTH: 15
<212> TYPE: PRT
<213> ORGANISM: Gallus gallus

<400> SEQUENCE: 434

-continued

Val Cys Gly Thr Asp Gly Val Thr Tyr Asp Asn Glu Cys Leu Leu
1               5                   10                  15

<210> SEQ ID NO 435
<211> LENGTH: 15
<212> TYPE: PRT
<213> ORGANISM: Gallus gallus

<400> SEQUENCE: 435

Thr Asp Gly Val Thr Tyr Asp Asn Glu Cys Leu Leu Cys Ala His
1               5                   10                  15

<210> SEQ ID NO 436
<211> LENGTH: 15
<212> TYPE: PRT
<213> ORGANISM: Gallus gallus

<400> SEQUENCE: 436

Val Thr Tyr Asp Asn Glu Cys Leu Leu Cys Ala His Lys Val Glu
1               5                   10                  15

<210> SEQ ID NO 437
<211> LENGTH: 15
<212> TYPE: PRT
<213> ORGANISM: Gallus gallus

<400> SEQUENCE: 437

Asp Asn Glu Cys Leu Leu Cys Ala His Lys Val Glu Gln Gly Ala
1               5                   10                  15

<210> SEQ ID NO 438
<211> LENGTH: 15
<212> TYPE: PRT
<213> ORGANISM: Gallus gallus

<400> SEQUENCE: 438

Cys Leu Leu Cys Ala His Lys Val Glu Gln Gly Ala Ser Val Asp
1               5                   10                  15

<210> SEQ ID NO 439
<211> LENGTH: 15
<212> TYPE: PRT
<213> ORGANISM: Gallus gallus

<400> SEQUENCE: 439

Cys Ala His Lys Val Glu Gln Gly Ala Ser Val Asp Lys Arg His
1               5                   10                  15

<210> SEQ ID NO 440
<211> LENGTH: 15
<212> TYPE: PRT
<213> ORGANISM: Gallus gallus

<400> SEQUENCE: 440

Lys Val Glu Gln Gly Ala Ser Val Asp Lys Arg His Asp Gly Gly
1               5                   10                  15

<210> SEQ ID NO 441
<211> LENGTH: 15
<212> TYPE: PRT
<213> ORGANISM: Gallus gallus

<400> SEQUENCE: 441

Gln Gly Ala Ser Val Asp Lys Arg His Asp Gly Gly Cys Arg Lys
1               5                   10                  15

<210> SEQ ID NO 442
<211> LENGTH: 15
<212> TYPE: PRT
<213> ORGANISM: Gallus gallus

<400> SEQUENCE: 442

Ser Val Asp Lys Arg His Asp Gly Gly Cys Arg Lys Glu Leu Ala
1               5                   10                  15

<210> SEQ ID NO 443
<211> LENGTH: 15
<212> TYPE: PRT
<213> ORGANISM: Gallus gallus

<400> SEQUENCE: 443

Lys Arg His Asp Gly Gly Cys Arg Lys Glu Leu Ala Ala Val Ser
1               5                   10                  15

<210> SEQ ID NO 444
<211> LENGTH: 15
<212> TYPE: PRT
<213> ORGANISM: Gallus gallus

<400> SEQUENCE: 444

Asp Gly Gly Cys Arg Lys Glu Leu Ala Ala Val Ser Val Asp Cys
1               5                   10                  15

<210> SEQ ID NO 445
<211> LENGTH: 15
<212> TYPE: PRT
<213> ORGANISM: Gallus gallus

<400> SEQUENCE: 445

Cys Arg Lys Glu Leu Ala Ala Val Ser Val Asp Cys Ser Glu Tyr
1               5                   10                  15

<210> SEQ ID NO 446
<211> LENGTH: 15
<212> TYPE: PRT
<213> ORGANISM: Gallus gallus

<400> SEQUENCE: 446

Glu Leu Ala Ala Val Ser Val Asp Cys Ser Glu Tyr Pro Lys Pro
1               5                   10                  15

<210> SEQ ID NO 447
<211> LENGTH: 15
<212> TYPE: PRT
<213> ORGANISM: Gallus gallus

<400> SEQUENCE: 447

Ala Val Ser Val Asp Cys Ser Glu Tyr Pro Lys Pro Asp Cys Thr
1               5                   10                  15

<210> SEQ ID NO 448
<211> LENGTH: 15
<212> TYPE: PRT
<213> ORGANISM: Gallus gallus

<400> SEQUENCE: 448

Val Asp Cys Ser Glu Tyr Pro Lys Pro Asp Cys Thr Ala Glu Asp
1               5                   10                  15

```
<210> SEQ ID NO 449
<211> LENGTH: 15
<212> TYPE: PRT
<213> ORGANISM: Gallus gallus

<400> SEQUENCE: 449

Ser Glu Tyr Pro Lys Pro Asp Cys Thr Ala Glu Asp Arg Pro Leu
1               5                   10                  15

<210> SEQ ID NO 450
<211> LENGTH: 15
<212> TYPE: PRT
<213> ORGANISM: Gallus gallus

<400> SEQUENCE: 450

Pro Lys Pro Asp Cys Thr Ala Glu Asp Arg Pro Leu Cys Gly Ser
1               5                   10                  15

<210> SEQ ID NO 451
<211> LENGTH: 15
<212> TYPE: PRT
<213> ORGANISM: Gallus gallus

<400> SEQUENCE: 451

Asp Cys Thr Ala Glu Asp Arg Pro Leu Cys Gly Ser Asp Asn Lys
1               5                   10                  15

<210> SEQ ID NO 452
<211> LENGTH: 15
<212> TYPE: PRT
<213> ORGANISM: Gallus gallus

<400> SEQUENCE: 452

Ala Glu Asp Arg Pro Leu Cys Gly Ser Asp Asn Lys Thr Tyr Gly
1               5                   10                  15

<210> SEQ ID NO 453
<211> LENGTH: 15
<212> TYPE: PRT
<213> ORGANISM: Gallus gallus

<400> SEQUENCE: 453

Arg Pro Leu Cys Gly Ser Asp Asn Lys Thr Tyr Gly Asn Lys Cys
1               5                   10                  15

<210> SEQ ID NO 454
<211> LENGTH: 15
<212> TYPE: PRT
<213> ORGANISM: Gallus gallus

<400> SEQUENCE: 454

Cys Gly Ser Asp Asn Lys Thr Tyr Gly Asn Lys Cys Asn Phe Cys
1               5                   10                  15

<210> SEQ ID NO 455
<211> LENGTH: 15
<212> TYPE: PRT
<213> ORGANISM: Gallus gallus

<400> SEQUENCE: 455

Asp Asn Lys Thr Tyr Gly Asn Lys Cys Asn Phe Cys Asn Ala Val
1               5                   10                  15

<210> SEQ ID NO 456
<211> LENGTH: 15
```

```
<212> TYPE: PRT
<213> ORGANISM: Gallus gallus

<400> SEQUENCE: 456

Thr Tyr Gly Asn Lys Cys Asn Phe Cys Asn Ala Val Val Glu Ser
1               5                   10                  15

<210> SEQ ID NO 457
<211> LENGTH: 15
<212> TYPE: PRT
<213> ORGANISM: Gallus gallus

<400> SEQUENCE: 457

Asn Lys Cys Asn Phe Cys Asn Ala Val Val Glu Ser Asn Gly Thr
1               5                   10                  15

<210> SEQ ID NO 458
<211> LENGTH: 15
<212> TYPE: PRT
<213> ORGANISM: Gallus gallus

<400> SEQUENCE: 458

Asn Phe Cys Asn Ala Val Val Glu Ser Asn Gly Thr Leu Thr Leu
1               5                   10                  15

<210> SEQ ID NO 459
<211> LENGTH: 15
<212> TYPE: PRT
<213> ORGANISM: Gallus gallus

<400> SEQUENCE: 459

Asn Ala Val Val Glu Ser Asn Gly Thr Leu Thr Leu Ser His Phe
1               5                   10                  15

<210> SEQ ID NO 460
<211> LENGTH: 15
<212> TYPE: PRT
<213> ORGANISM: Gallus gallus

<400> SEQUENCE: 460

Val Glu Ser Asn Gly Thr Leu Thr Leu Ser His Phe Gly Lys Cys
1               5                   10                  15

<210> SEQ ID NO 461
<211> LENGTH: 15
<212> TYPE: PRT
<213> ORGANISM: Unknown
<220> FEATURE:
<223> OTHER INFORMATION: Shrimp peptide

<400> SEQUENCE: 461

Met Ala Asp Ala Ala Val Ile Glu Lys Leu Glu Ala Gly Phe Lys
1               5                   10                  15

<210> SEQ ID NO 462
<211> LENGTH: 15
<212> TYPE: PRT
<213> ORGANISM: Unknown
<220> FEATURE:
<223> OTHER INFORMATION: Shrimp peptide

<400> SEQUENCE: 462

Val Ile Glu Lys Leu Glu Ala Gly Phe Lys Lys Leu Glu Ala Ala
1               5                   10                  15
```

```
<210> SEQ ID NO 463
<211> LENGTH: 15
<212> TYPE: PRT
<213> ORGANISM: Unknown
<220> FEATURE:
<223> OTHER INFORMATION: Shrimp peptide

<400> SEQUENCE: 463

Glu Ala Gly Phe Lys Lys Leu Glu Ala Ala Thr Asp Cys Lys Ser
1               5                   10                  15

<210> SEQ ID NO 464
<211> LENGTH: 15
<212> TYPE: PRT
<213> ORGANISM: Unknown
<220> FEATURE:
<223> OTHER INFORMATION: Shrimp peptide

<400> SEQUENCE: 464

Lys Leu Glu Ala Ala Thr Asp Cys Lys Ser Leu Leu Lys Lys Tyr
1               5                   10                  15

<210> SEQ ID NO 465
<211> LENGTH: 15
<212> TYPE: PRT
<213> ORGANISM: Unknown
<220> FEATURE:
<223> OTHER INFORMATION: Shrimp peptide

<400> SEQUENCE: 465

Thr Asp Cys Lys Ser Leu Leu Lys Lys Tyr Leu Thr Lys Glu Val
1               5                   10                  15

<210> SEQ ID NO 466
<211> LENGTH: 15
<212> TYPE: PRT
<213> ORGANISM: Unknown
<220> FEATURE:
<223> OTHER INFORMATION: Shrimp peptide

<400> SEQUENCE: 466

Leu Leu Lys Lys Tyr Leu Thr Lys Glu Val Phe Asp Lys Leu Lys
1               5                   10                  15

<210> SEQ ID NO 467
<211> LENGTH: 15
<212> TYPE: PRT
<213> ORGANISM: Unknown
<220> FEATURE:
<223> OTHER INFORMATION: Shrimp peptide

<400> SEQUENCE: 467

Leu Leu Lys Lys Tyr Leu Thr Lys Glu Val Phe Asp Lys Leu Lys
1               5                   10                  15

<210> SEQ ID NO 468
<211> LENGTH: 15
<212> TYPE: PRT
<213> ORGANISM: Unknown
<220> FEATURE:
<223> OTHER INFORMATION: Shrimp peptide

<400> SEQUENCE: 468

Phe Asp Lys Leu Lys Asp Lys Lys Thr Ser Leu Gly Ala Thr Leu
1               5                   10                  15

<210> SEQ ID NO 469
```

```
<211> LENGTH: 15
<212> TYPE: PRT
<213> ORGANISM: Unknown
<220> FEATURE:
<223> OTHER INFORMATION: Shrimp peptide

<400> SEQUENCE: 469

Asp Lys Lys Thr Ser Leu Gly Ala Thr Leu Leu Asp Val Ile Gln
1               5                   10                  15

<210> SEQ ID NO 470
<211> LENGTH: 15
<212> TYPE: PRT
<213> ORGANISM: Unknown
<220> FEATURE:
<223> OTHER INFORMATION: Shrimp peptide

<400> SEQUENCE: 470

Leu Gly Ala Thr Leu Leu Asp Val Ile Gln Ser Gly Val Glu Asn
1               5                   10                  15

<210> SEQ ID NO 471
<211> LENGTH: 15
<212> TYPE: PRT
<213> ORGANISM: Unknown
<220> FEATURE:
<223> OTHER INFORMATION: Shrimp peptide

<400> SEQUENCE: 471

Leu Asp Val Ile Gln Ser Gly Val Glu Asn Leu Asp Ser Gly Val
1               5                   10                  15

<210> SEQ ID NO 472
<211> LENGTH: 15
<212> TYPE: PRT
<213> ORGANISM: Unknown
<220> FEATURE:
<223> OTHER INFORMATION: Shrimp peptide

<400> SEQUENCE: 472

Ser Gly Val Glu Asn Leu Asp Ser Gly Val Gly Ile Tyr Ala Pro
1               5                   10                  15

<210> SEQ ID NO 473
<211> LENGTH: 15
<212> TYPE: PRT
<213> ORGANISM: Unknown
<220> FEATURE:
<223> OTHER INFORMATION: Shrimp peptide

<400> SEQUENCE: 473

Leu Asp Ser Gly Val Gly Ile Tyr Ala Pro Asp Ala Glu Ala Tyr
1               5                   10                  15

<210> SEQ ID NO 474
<211> LENGTH: 15
<212> TYPE: PRT
<213> ORGANISM: Unknown
<220> FEATURE:
<223> OTHER INFORMATION: Shrimp peptide

<400> SEQUENCE: 474

Gly Ile Tyr Ala Pro Asp Ala Glu Ala Tyr Thr Leu Phe Ala Pro
1               5                   10                  15

<210> SEQ ID NO 475
<211> LENGTH: 15
```

```
<212> TYPE: PRT
<213> ORGANISM: Unknown
<220> FEATURE:
<223> OTHER INFORMATION: Shrimp peptide

<400> SEQUENCE: 475

Asp Ala Glu Ala Tyr Thr Leu Phe Ala Pro Leu Phe Asp Pro Ile
1               5                   10                  15

<210> SEQ ID NO 476
<211> LENGTH: 15
<212> TYPE: PRT
<213> ORGANISM: Unknown
<220> FEATURE:
<223> OTHER INFORMATION: Shrimp peptide

<400> SEQUENCE: 476

Thr Leu Phe Ala Pro Leu Phe Asp Pro Ile Ile Glu Asp Tyr His
1               5                   10                  15

<210> SEQ ID NO 477
<211> LENGTH: 15
<212> TYPE: PRT
<213> ORGANISM: Unknown
<220> FEATURE:
<223> OTHER INFORMATION: Shrimp peptide

<400> SEQUENCE: 477

Leu Phe Asp Pro Ile Ile Glu Asp Tyr His Val Gly Phe Lys Gln
1               5                   10                  15

<210> SEQ ID NO 478
<211> LENGTH: 15
<212> TYPE: PRT
<213> ORGANISM: Unknown
<220> FEATURE:
<223> OTHER INFORMATION: Shrimp peptide

<400> SEQUENCE: 478

Ile Glu Asp Tyr His Val Gly Phe Lys Gln Thr Asp Lys His Pro
1               5                   10                  15

<210> SEQ ID NO 479
<211> LENGTH: 15
<212> TYPE: PRT
<213> ORGANISM: Unknown
<220> FEATURE:
<223> OTHER INFORMATION: Shrimp peptide

<400> SEQUENCE: 479

Val Gly Phe Lys Gln Thr Asp Lys His Pro Asn Lys Asp Phe Gly
1               5                   10                  15

<210> SEQ ID NO 480
<211> LENGTH: 15
<212> TYPE: PRT
<213> ORGANISM: Unknown
<220> FEATURE:
<223> OTHER INFORMATION: Shrimp peptide

<400> SEQUENCE: 480

Thr Asp Lys His Pro Asn Lys Asp Phe Gly Asp Val Asn Ser Phe
1               5                   10                  15

<210> SEQ ID NO 481
<211> LENGTH: 15
<212> TYPE: PRT
```

<213> ORGANISM: Unknown
<220> FEATURE:
<223> OTHER INFORMATION: Shrimp peptide

<400> SEQUENCE: 481

Asn Lys Asp Phe Gly Asp Val Asn Ser Phe Asn Val Asp Pro
1               5                   10                  15

<210> SEQ ID NO 482
<211> LENGTH: 15
<212> TYPE: PRT
<213> ORGANISM: Unknown
<220> FEATURE:
<223> OTHER INFORMATION: Shrimp peptide

<400> SEQUENCE: 482

Asp Val Asn Ser Phe Asn Val Asp Pro Glu Gly Lys Phe Val
1               5                   10                  15

<210> SEQ ID NO 483
<211> LENGTH: 15
<212> TYPE: PRT
<213> ORGANISM: Unknown
<220> FEATURE:
<223> OTHER INFORMATION: Shrimp peptide

<400> SEQUENCE: 483

Val Asn Val Asp Pro Glu Gly Lys Phe Val Ile Ser Thr Arg Val
1               5                   10                  15

<210> SEQ ID NO 484
<211> LENGTH: 15
<212> TYPE: PRT
<213> ORGANISM: Unknown
<220> FEATURE:
<223> OTHER INFORMATION: Shrimp peptide

<400> SEQUENCE: 484

Glu Gly Lys Phe Val Ile Ser Thr Arg Val Arg Cys Gly Arg Ser
1               5                   10                  15

<210> SEQ ID NO 485
<211> LENGTH: 15
<212> TYPE: PRT
<213> ORGANISM: Unknown
<220> FEATURE:
<223> OTHER INFORMATION: Shrimp peptide

<400> SEQUENCE: 485

Ile Ser Thr Arg Val Arg Cys Gly Arg Ser Met Gln Gly Tyr Pro
1               5                   10                  15

<210> SEQ ID NO 486
<211> LENGTH: 15
<212> TYPE: PRT
<213> ORGANISM: Unknown
<220> FEATURE:
<223> OTHER INFORMATION: Shrimp peptide

<400> SEQUENCE: 486

Arg Cys Gly Arg Ser Met Gln Gly Tyr Pro Phe Asn Pro Cys Leu
1               5                   10                  15

<210> SEQ ID NO 487
<211> LENGTH: 15
<212> TYPE: PRT
<213> ORGANISM: Unknown

```
<220> FEATURE:
<223> OTHER INFORMATION: Shrimp peptide

<400> SEQUENCE: 487

Met Gln Gly Tyr Pro Phe Asn Pro Cys Leu Thr Glu Ser Gln Tyr
1               5                   10                  15

<210> SEQ ID NO 488
<211> LENGTH: 15
<212> TYPE: PRT
<213> ORGANISM: Unknown
<220> FEATURE:
<223> OTHER INFORMATION: Shrimp peptide

<400> SEQUENCE: 488

Phe Asn Pro Cys Leu Thr Glu Ser Gln Tyr Lys Glu Met Glu Ala
1               5                   10                  15

<210> SEQ ID NO 489
<211> LENGTH: 15
<212> TYPE: PRT
<213> ORGANISM: Unknown
<220> FEATURE:
<223> OTHER INFORMATION: Shrimp peptide

<400> SEQUENCE: 489

Thr Glu Ser Gln Tyr Lys Glu Met Glu Ala Lys Val Ser Ser Thr
1               5                   10                  15

<210> SEQ ID NO 490
<211> LENGTH: 15
<212> TYPE: PRT
<213> ORGANISM: Unknown
<220> FEATURE:
<223> OTHER INFORMATION: Shrimp peptide

<400> SEQUENCE: 490

Lys Glu Met Glu Ala Lys Val Ser Ser Thr Leu Ser Ser Leu Glu
1               5                   10                  15

<210> SEQ ID NO 491
<211> LENGTH: 15
<212> TYPE: PRT
<213> ORGANISM: Unknown
<220> FEATURE:
<223> OTHER INFORMATION: Shrimp peptide

<400> SEQUENCE: 491

Lys Val Ser Ser Thr Leu Ser Ser Leu Glu Gly Glu Leu Lys Gly
1               5                   10                  15

<210> SEQ ID NO 492
<211> LENGTH: 15
<212> TYPE: PRT
<213> ORGANISM: Unknown
<220> FEATURE:
<223> OTHER INFORMATION: Shrimp peptide

<400> SEQUENCE: 492

Leu Ser Ser Leu Glu Gly Glu Leu Lys Gly Thr Tyr Tyr Pro Leu
1               5                   10                  15

<210> SEQ ID NO 493
<211> LENGTH: 15
<212> TYPE: PRT
<213> ORGANISM: Unknown
<220> FEATURE:
```

<223> OTHER INFORMATION: Shrimp peptide

<400> SEQUENCE: 493

Gly Glu Leu Lys Gly Thr Tyr Tyr Pro Leu Thr Gly Met Ser Lys
1               5                   10                  15

<210> SEQ ID NO 494
<211> LENGTH: 15
<212> TYPE: PRT
<213> ORGANISM: Unknown
<220> FEATURE:
<223> OTHER INFORMATION: Shrimp peptide

<400> SEQUENCE: 494

Thr Tyr Tyr Pro Leu Thr Gly Met Ser Lys Glu Val Gln Gln Lys
1               5                   10                  15

<210> SEQ ID NO 495
<211> LENGTH: 15
<212> TYPE: PRT
<213> ORGANISM: Unknown
<220> FEATURE:
<223> OTHER INFORMATION: Shrimp peptide

<400> SEQUENCE: 495

Thr Gly Met Ser Lys Glu Val Gln Gln Lys Leu Ile Asp Asp His
1               5                   10                  15

<210> SEQ ID NO 496
<211> LENGTH: 15
<212> TYPE: PRT
<213> ORGANISM: Unknown
<220> FEATURE:
<223> OTHER INFORMATION: Shrimp peptide

<400> SEQUENCE: 496

Glu Val Gln Gln Lys Leu Ile Asp Asp His Phe Leu Phe Lys Glu
1               5                   10                  15

<210> SEQ ID NO 497
<211> LENGTH: 15
<212> TYPE: PRT
<213> ORGANISM: Unknown
<220> FEATURE:
<223> OTHER INFORMATION: Shrimp peptide

<400> SEQUENCE: 497

Leu Ile Asp Asp His Phe Leu Phe Lys Glu Gly Asp Arg Phe Leu
1               5                   10                  15

<210> SEQ ID NO 498
<211> LENGTH: 15
<212> TYPE: PRT
<213> ORGANISM: Unknown
<220> FEATURE:
<223> OTHER INFORMATION: Shrimp peptide

<400> SEQUENCE: 498

Phe Leu Phe Lys Glu Gly Asp Arg Phe Leu Gln Ala Ala Asn Ala
1               5                   10                  15

<210> SEQ ID NO 499
<211> LENGTH: 15
<212> TYPE: PRT
<213> ORGANISM: Unknown
<220> FEATURE:
<223> OTHER INFORMATION: Shrimp peptide

```
<400> SEQUENCE: 499

Gly Asp Arg Phe Leu Gln Ala Ala Asn Ala Cys Arg Tyr Trp Pro
1               5                   10                  15

<210> SEQ ID NO 500
<211> LENGTH: 15
<212> TYPE: PRT
<213> ORGANISM: Unknown
<220> FEATURE:
<223> OTHER INFORMATION: Shrimp peptide

<400> SEQUENCE: 500

Gln Ala Ala Asn Ala Cys Arg Tyr Trp Pro Ala Gly Arg Gly Ile
1               5                   10                  15

<210> SEQ ID NO 501
<211> LENGTH: 15
<212> TYPE: PRT
<213> ORGANISM: Unknown
<220> FEATURE:
<223> OTHER INFORMATION: Shrimp peptide

<400> SEQUENCE: 501

Cys Arg Tyr Trp Pro Ala Gly Arg Gly Ile Tyr His Asn Asp Asn
1               5                   10                  15

<210> SEQ ID NO 502
<211> LENGTH: 15
<212> TYPE: PRT
<213> ORGANISM: Unknown
<220> FEATURE:
<223> OTHER INFORMATION: Shrimp peptide

<400> SEQUENCE: 502

Ala Gly Arg Gly Ile Tyr His Asn Asp Asn Lys Thr Phe Leu Val
1               5                   10                  15

<210> SEQ ID NO 503
<211> LENGTH: 15
<212> TYPE: PRT
<213> ORGANISM: Unknown
<220> FEATURE:
<223> OTHER INFORMATION: Shrimp peptide

<400> SEQUENCE: 503

Tyr His Asn Asp Asn Lys Thr Phe Leu Val Trp Val Asn Glu Glu
1               5                   10                  15

<210> SEQ ID NO 504
<211> LENGTH: 15
<212> TYPE: PRT
<213> ORGANISM: Unknown
<220> FEATURE:
<223> OTHER INFORMATION: Shrimp peptide

<400> SEQUENCE: 504

Lys Thr Phe Leu Val Trp Val Asn Glu Glu Asp His Leu Arg Ile
1               5                   10                  15

<210> SEQ ID NO 505
<211> LENGTH: 15
<212> TYPE: PRT
<213> ORGANISM: Unknown
<220> FEATURE:
<223> OTHER INFORMATION: Shrimp peptide
```

```
<400> SEQUENCE: 505

Trp Val Asn Glu Glu Asp His Leu Arg Ile Ile Ser Met Gln Met
1               5                   10                  15

<210> SEQ ID NO 506
<211> LENGTH: 15
<212> TYPE: PRT
<213> ORGANISM: Unknown
<220> FEATURE:
<223> OTHER INFORMATION: Shrimp peptide

<400> SEQUENCE: 506

Asp His Leu Arg Ile Ile Ser Met Gln Met Gly Gly Asp Leu Gly
1               5                   10                  15

<210> SEQ ID NO 507
<211> LENGTH: 15
<212> TYPE: PRT
<213> ORGANISM: Unknown
<220> FEATURE:
<223> OTHER INFORMATION: Shrimp peptide

<400> SEQUENCE: 507

Ile Ser Met Gln Met Gly Gly Asp Leu Gly Gln Val Phe Arg Arg
1               5                   10                  15

<210> SEQ ID NO 508
<211> LENGTH: 15
<212> TYPE: PRT
<213> ORGANISM: Unknown
<220> FEATURE:
<223> OTHER INFORMATION: Shrimp peptide

<400> SEQUENCE: 508

Gly Gly Asp Leu Gly Gln Val Phe Arg Arg Leu Thr Ser Ala Val
1               5                   10                  15

<210> SEQ ID NO 509
<211> LENGTH: 15
<212> TYPE: PRT
<213> ORGANISM: Unknown
<220> FEATURE:
<223> OTHER INFORMATION: Shrimp peptide

<400> SEQUENCE: 509

Gln Val Phe Arg Arg Leu Thr Ser Ala Val Asn Glu Ile Glu Lys
1               5                   10                  15

<210> SEQ ID NO 510
<211> LENGTH: 15
<212> TYPE: PRT
<213> ORGANISM: Unknown
<220> FEATURE:
<223> OTHER INFORMATION: Shrimp peptide

<400> SEQUENCE: 510

Leu Thr Ser Ala Val Asn Glu Ile Glu Lys Arg Ile Pro Phe Ser
1               5                   10                  15

<210> SEQ ID NO 511
<211> LENGTH: 15
<212> TYPE: PRT
<213> ORGANISM: Unknown
<220> FEATURE:
<223> OTHER INFORMATION: Shrimp peptide

<400> SEQUENCE: 511
```

Asn Glu Ile Glu Lys Arg Ile Pro Phe Ser His His Asp Arg Leu
1               5                   10                  15

<210> SEQ ID NO 512
<211> LENGTH: 15
<212> TYPE: PRT
<213> ORGANISM: Unknown
<220> FEATURE:
<223> OTHER INFORMATION: Shrimp peptide

<400> SEQUENCE: 512

Arg Ile Pro Phe Ser His His Asp Arg Leu Gly Phe Leu Thr Phe
1               5                   10                  15

<210> SEQ ID NO 513
<211> LENGTH: 15
<212> TYPE: PRT
<213> ORGANISM: Unknown
<220> FEATURE:
<223> OTHER INFORMATION: Shrimp peptide

<400> SEQUENCE: 513

His His Asp Arg Leu Gly Phe Leu Thr Phe Cys Pro Thr Asn Leu
1               5                   10                  15

<210> SEQ ID NO 514
<211> LENGTH: 15
<212> TYPE: PRT
<213> ORGANISM: Unknown
<220> FEATURE:
<223> OTHER INFORMATION: Shrimp peptide

<400> SEQUENCE: 514

Gly Phe Leu Thr Phe Cys Pro Thr Asn Leu Gly Thr Thr Val Arg
1               5                   10                  15

<210> SEQ ID NO 515
<211> LENGTH: 15
<212> TYPE: PRT
<213> ORGANISM: Unknown
<220> FEATURE:
<223> OTHER INFORMATION: Shrimp peptide

<400> SEQUENCE: 515

Cys Pro Thr Asn Leu Gly Thr Thr Val Arg Ala Ser Val His Ile
1               5                   10                  15

<210> SEQ ID NO 516
<211> LENGTH: 15
<212> TYPE: PRT
<213> ORGANISM: Unknown
<220> FEATURE:
<223> OTHER INFORMATION: Shrimp peptide

<400> SEQUENCE: 516

Gly Thr Thr Val Arg Ala Ser Val His Ile Lys Leu Pro Lys Leu
1               5                   10                  15

<210> SEQ ID NO 517
<211> LENGTH: 15
<212> TYPE: PRT
<213> ORGANISM: Unknown
<220> FEATURE:
<223> OTHER INFORMATION: Shrimp peptide

<400> SEQUENCE: 517

```
Ala Ser Val His Ile Lys Leu Pro Lys Leu Ala Ala Asn Arg Glu
1               5                   10                  15
```

<210> SEQ ID NO 518
<211> LENGTH: 15
<212> TYPE: PRT
<213> ORGANISM: Unknown
<220> FEATURE:
<223> OTHER INFORMATION: Shrimp peptide

<400> SEQUENCE: 518

```
Lys Leu Pro Lys Leu Ala Ala Asn Arg Glu Lys Leu Glu Glu Val
1               5                   10                  15
```

<210> SEQ ID NO 519
<211> LENGTH: 15
<212> TYPE: PRT
<213> ORGANISM: Unknown
<220> FEATURE:
<223> OTHER INFORMATION: Shrimp peptide

<400> SEQUENCE: 519

```
Ala Ala Asn Arg Glu Lys Leu Glu Glu Val Ala Gly Lys Tyr Asn
1               5                   10                  15
```

<210> SEQ ID NO 520
<211> LENGTH: 15
<212> TYPE: PRT
<213> ORGANISM: Unknown
<220> FEATURE:
<223> OTHER INFORMATION: Shrimp peptide

<400> SEQUENCE: 520

```
Lys Leu Glu Glu Val Ala Gly Lys Tyr Asn Leu Gln Val Arg Gly
1               5                   10                  15
```

<210> SEQ ID NO 521
<211> LENGTH: 15
<212> TYPE: PRT
<213> ORGANISM: Unknown
<220> FEATURE:
<223> OTHER INFORMATION: Shrimp peptide

<400> SEQUENCE: 521

```
Ala Gly Lys Tyr Asn Leu Gln Val Arg Gly Thr Arg Gly Glu His
1               5                   10                  15
```

<210> SEQ ID NO 522
<211> LENGTH: 15
<212> TYPE: PRT
<213> ORGANISM: Unknown
<220> FEATURE:
<223> OTHER INFORMATION: Shrimp peptide

<400> SEQUENCE: 522

```
Leu Gln Val Arg Gly Thr Arg Gly Glu His Thr Glu Ala Glu Gly
1               5                   10                  15
```

<210> SEQ ID NO 523
<211> LENGTH: 15
<212> TYPE: PRT
<213> ORGANISM: Unknown
<220> FEATURE:
<223> OTHER INFORMATION: Shrimp peptide

<400> SEQUENCE: 523

Thr Arg Gly Glu His Thr Glu Ala Glu Gly Gly Ile Tyr Asp Ile

```
1               5                  10                 15
```

<210> SEQ ID NO 524
<211> LENGTH: 15
<212> TYPE: PRT
<213> ORGANISM: Unknown
<220> FEATURE:
<223> OTHER INFORMATION: Shrimp peptide

<400> SEQUENCE: 524

```
Thr Glu Ala Glu Gly Gly Ile Tyr Asp Ile Ser Asn Lys Arg Arg
1               5                  10                 15
```

<210> SEQ ID NO 525
<211> LENGTH: 15
<212> TYPE: PRT
<213> ORGANISM: Unknown
<220> FEATURE:
<223> OTHER INFORMATION: Shrimp peptide

<400> SEQUENCE: 525

```
Gly Ile Tyr Asp Ile Ser Asn Lys Arg Arg Met Gly Leu Thr Glu
1               5                  10                 15
```

<210> SEQ ID NO 526
<211> LENGTH: 15
<212> TYPE: PRT
<213> ORGANISM: Unknown
<220> FEATURE:
<223> OTHER INFORMATION: Shrimp peptide

<400> SEQUENCE: 526

```
Ser Asn Lys Arg Arg Met Gly Leu Thr Glu Phe Gln Ala Val Lys
1               5                  10                 15
```

<210> SEQ ID NO 527
<211> LENGTH: 15
<212> TYPE: PRT
<213> ORGANISM: Unknown
<220> FEATURE:
<223> OTHER INFORMATION: Shrimp peptide

<400> SEQUENCE: 527

```
Met Gly Leu Thr Glu Phe Gln Ala Val Lys Glu Met Gln Asp Gly
1               5                  10                 15
```

<210> SEQ ID NO 528
<211> LENGTH: 15
<212> TYPE: PRT
<213> ORGANISM: Unknown
<220> FEATURE:
<223> OTHER INFORMATION: Shrimp peptide

<400> SEQUENCE: 528

```
Phe Gln Ala Val Lys Glu Met Gln Asp Gly Ile Leu Glu Leu Ile
1               5                  10                 15
```

<210> SEQ ID NO 529
<211> LENGTH: 15
<212> TYPE: PRT
<213> ORGANISM: Unknown
<220> FEATURE:
<223> OTHER INFORMATION: Shrimp peptide

<400> SEQUENCE: 529

```
Glu Met Gln Asp Gly Ile Leu Glu Leu Ile Lys Ile Glu Lys Glu
1               5                  10                 15
```

```
<210> SEQ ID NO 530
<211> LENGTH: 15
<212> TYPE: PRT
<213> ORGANISM: Unknown
<220> FEATURE:
<223> OTHER INFORMATION: Shrimp peptide

<400> SEQUENCE: 530

Met Ser Arg Lys Ser Gly Ser Arg Ser Ser Lys Arg Ser Lys
1               5                   10                  15

<210> SEQ ID NO 531
<211> LENGTH: 15
<212> TYPE: PRT
<213> ORGANISM: Unknown
<220> FEATURE:
<223> OTHER INFORMATION: Shrimp peptide

<400> SEQUENCE: 531

Gly Ser Arg Ser Ser Ser Lys Arg Ser Lys Lys Ser Gly Gly Gly
1               5                   10                  15

<210> SEQ ID NO 532
<211> LENGTH: 15
<212> TYPE: PRT
<213> ORGANISM: Unknown
<220> FEATURE:
<223> OTHER INFORMATION: Shrimp peptide

<400> SEQUENCE: 532

Ser Lys Arg Ser Lys Lys Ser Gly Gly Gly Ser Asn Val Phe Asp
1               5                   10                  15

<210> SEQ ID NO 533
<211> LENGTH: 15
<212> TYPE: PRT
<213> ORGANISM: Unknown
<220> FEATURE:
<223> OTHER INFORMATION: Shrimp peptide

<400> SEQUENCE: 533

Lys Ser Gly Gly Gly Ser Asn Val Phe Asp Met Phe Thr Gln Arg
1               5                   10                  15

<210> SEQ ID NO 534
<211> LENGTH: 15
<212> TYPE: PRT
<213> ORGANISM: Unknown
<220> FEATURE:
<223> OTHER INFORMATION: Shrimp peptide

<400> SEQUENCE: 534

Ser Asn Val Phe Asp Met Phe Thr Gln Arg Gln Val Ala Glu Phe
1               5                   10                  15

<210> SEQ ID NO 535
<211> LENGTH: 15
<212> TYPE: PRT
<213> ORGANISM: Unknown
<220> FEATURE:
<223> OTHER INFORMATION: Shrimp peptide

<400> SEQUENCE: 535

Met Phe Thr Gln Arg Gln Val Ala Glu Phe Lys Glu Gly Phe Gln
1               5                   10                  15
```

```
<210> SEQ ID NO 536
<211> LENGTH: 15
<212> TYPE: PRT
<213> ORGANISM: Unknown
<220> FEATURE:
<223> OTHER INFORMATION: Shrimp peptide

<400> SEQUENCE: 536

Gln Val Ala Glu Phe Lys Glu Gly Phe Gln Leu Met Asp Arg Asp
1               5                   10                  15

<210> SEQ ID NO 537
<211> LENGTH: 15
<212> TYPE: PRT
<213> ORGANISM: Unknown
<220> FEATURE:
<223> OTHER INFORMATION: Shrimp peptide

<400> SEQUENCE: 537

Lys Glu Gly Phe Gln Leu Met Asp Arg Asp Lys Asp Gly Val Ile
1               5                   10                  15

<210> SEQ ID NO 538
<211> LENGTH: 15
<212> TYPE: PRT
<213> ORGANISM: Unknown
<220> FEATURE:
<223> OTHER INFORMATION: Shrimp peptide

<400> SEQUENCE: 538

Leu Met Asp Arg Asp Lys Asp Gly Val Ile Gly Lys Thr Asp Leu
1               5                   10                  15

<210> SEQ ID NO 539
<211> LENGTH: 15
<212> TYPE: PRT
<213> ORGANISM: Unknown
<220> FEATURE:
<223> OTHER INFORMATION: Shrimp peptide

<400> SEQUENCE: 539

Lys Asp Gly Val Ile Gly Lys Thr Asp Leu Arg Gly Thr Phe Asp
1               5                   10                  15

<210> SEQ ID NO 540
<211> LENGTH: 15
<212> TYPE: PRT
<213> ORGANISM: Unknown
<220> FEATURE:
<223> OTHER INFORMATION: Shrimp peptide

<400> SEQUENCE: 540

Gly Lys Thr Asp Leu Arg Gly Thr Phe Asp Glu Ile Gly Arg Ile
1               5                   10                  15

<210> SEQ ID NO 541
<211> LENGTH: 15
<212> TYPE: PRT
<213> ORGANISM: Unknown
<220> FEATURE:
<223> OTHER INFORMATION: Shrimp peptide

<400> SEQUENCE: 541

Arg Gly Thr Phe Asp Glu Ile Gly Arg Ile Ala Thr Asp Gln Glu
1               5                   10                  15
```

```
<210> SEQ ID NO 542
<211> LENGTH: 15
<212> TYPE: PRT
<213> ORGANISM: Unknown
<220> FEATURE:
<223> OTHER INFORMATION: Shrimp peptide

<400> SEQUENCE: 542

Glu Ile Gly Arg Ile Ala Thr Asp Gln Glu Leu Asp Glu Met Leu
1               5                   10                  15

<210> SEQ ID NO 543
<211> LENGTH: 15
<212> TYPE: PRT
<213> ORGANISM: Unknown
<220> FEATURE:
<223> OTHER INFORMATION: Shrimp peptide

<400> SEQUENCE: 543

Ala Thr Asp Gln Glu Leu Asp Glu Met Leu Ala Asp Ala Pro Ala
1               5                   10                  15

<210> SEQ ID NO 544
<211> LENGTH: 15
<212> TYPE: PRT
<213> ORGANISM: Unknown
<220> FEATURE:
<223> OTHER INFORMATION: Shrimp peptide

<400> SEQUENCE: 544

Leu Asp Glu Met Leu Ala Asp Ala Pro Ala Pro Ile Asn Phe Thr
1               5                   10                  15

<210> SEQ ID NO 545
<211> LENGTH: 15
<212> TYPE: PRT
<213> ORGANISM: Unknown
<220> FEATURE:
<223> OTHER INFORMATION: Shrimp peptide

<400> SEQUENCE: 545

Ala Asp Ala Pro Ala Pro Ile Asn Phe Thr Met Leu Leu Asn Met
1               5                   10                  15

<210> SEQ ID NO 546
<211> LENGTH: 15
<212> TYPE: PRT
<213> ORGANISM: Unknown
<220> FEATURE:
<223> OTHER INFORMATION: Shrimp peptide

<400> SEQUENCE: 546

Pro Ile Asn Phe Thr Met Leu Leu Asn Met Phe Ala Glu Arg Gln
1               5                   10                  15

<210> SEQ ID NO 547
<211> LENGTH: 15
<212> TYPE: PRT
<213> ORGANISM: Unknown
<220> FEATURE:
<223> OTHER INFORMATION: Shrimp peptide

<400> SEQUENCE: 547

Met Leu Leu Asn Met Phe Ala Glu Arg Gln Thr Gly Glu Ser Asp
1               5                   10                  15

<210> SEQ ID NO 548
```

```
<211> LENGTH: 15
<212> TYPE: PRT
<213> ORGANISM: Unknown
<220> FEATURE:
<223> OTHER INFORMATION: Shrimp peptide

<400> SEQUENCE: 548

Phe Ala Glu Arg Gln Thr Gly Glu Ser Asp Asp Asp Val Val
1               5                   10                  15

<210> SEQ ID NO 549
<211> LENGTH: 15
<212> TYPE: PRT
<213> ORGANISM: Unknown
<220> FEATURE:
<223> OTHER INFORMATION: Shrimp peptide

<400> SEQUENCE: 549

Thr Gly Glu Ser Asp Asp Asp Val Val Ala Lys Ala Phe Leu
1               5                   10                  15

<210> SEQ ID NO 550
<211> LENGTH: 15
<212> TYPE: PRT
<213> ORGANISM: Unknown
<220> FEATURE:
<223> OTHER INFORMATION: Shrimp peptide

<400> SEQUENCE: 550

Asp Asp Asp Val Val Ala Lys Ala Phe Leu Ala Phe Ala Asp Glu
1               5                   10                  15

<210> SEQ ID NO 551
<211> LENGTH: 15
<212> TYPE: PRT
<213> ORGANISM: Unknown
<220> FEATURE:
<223> OTHER INFORMATION: Shrimp peptide

<400> SEQUENCE: 551

Ala Lys Ala Phe Leu Ala Phe Ala Asp Glu Glu Gly Asn Ile Asp
1               5                   10                  15

<210> SEQ ID NO 552
<211> LENGTH: 15
<212> TYPE: PRT
<213> ORGANISM: Unknown
<220> FEATURE:
<223> OTHER INFORMATION: Shrimp peptide

<400> SEQUENCE: 552

Ala Phe Ala Asp Glu Glu Gly Asn Ile Asp Cys Asp Thr Phe Arg
1               5                   10                  15

<210> SEQ ID NO 553
<211> LENGTH: 15
<212> TYPE: PRT
<213> ORGANISM: Unknown
<220> FEATURE:
<223> OTHER INFORMATION: Shrimp peptide

<400> SEQUENCE: 553

Glu Gly Asn Ile Asp Cys Asp Thr Phe Arg His Ala Leu Met Thr
1               5                   10                  15

<210> SEQ ID NO 554
<211> LENGTH: 15
```

<212> TYPE: PRT
<213> ORGANISM: Unknown
<220> FEATURE:
<223> OTHER INFORMATION: Shrimp peptide

<400> SEQUENCE: 554

Cys Asp Thr Phe Arg His Ala Leu Met Thr Trp Gly Asp Lys Phe
1               5                   10                  15

<210> SEQ ID NO 555
<211> LENGTH: 15
<212> TYPE: PRT
<213> ORGANISM: Unknown
<220> FEATURE:
<223> OTHER INFORMATION: Shrimp peptide

<400> SEQUENCE: 555

His Ala Leu Met Thr Trp Gly Asp Lys Phe Ser Ser Gln Glu Ala
1               5                   10                  15

<210> SEQ ID NO 556
<211> LENGTH: 15
<212> TYPE: PRT
<213> ORGANISM: Unknown
<220> FEATURE:
<223> OTHER INFORMATION: Shrimp peptide

<400> SEQUENCE: 556

Trp Gly Asp Lys Phe Ser Ser Gln Glu Ala Asp Ala Leu Asp
1               5                   10                  15

<210> SEQ ID NO 557
<211> LENGTH: 15
<212> TYPE: PRT
<213> ORGANISM: Unknown
<220> FEATURE:
<223> OTHER INFORMATION: Shrimp peptide

<400> SEQUENCE: 557

Ser Ser Gln Glu Ala Asp Ala Leu Asp Gln Met Asp Ile Asp
1               5                   10                  15

<210> SEQ ID NO 558
<211> LENGTH: 15
<212> TYPE: PRT
<213> ORGANISM: Unknown
<220> FEATURE:
<223> OTHER INFORMATION: Shrimp peptide

<400> SEQUENCE: 558

Asp Asp Ala Leu Asp Gln Met Asp Ile Asp Asp Gly Gly Lys Ile
1               5                   10                  15

<210> SEQ ID NO 559
<211> LENGTH: 15
<212> TYPE: PRT
<213> ORGANISM: Unknown
<220> FEATURE:
<223> OTHER INFORMATION: Shrimp peptide

<400> SEQUENCE: 559

Gln Met Asp Ile Asp Asp Gly Gly Lys Ile Asp Val Gln Gly Val
1               5                   10                  15

<210> SEQ ID NO 560
<211> LENGTH: 15
<212> TYPE: PRT

```
<213> ORGANISM: Unknown
<220> FEATURE:
<223> OTHER INFORMATION: Shrimp peptide

<400> SEQUENCE: 560

Asp Gly Gly Lys Ile Asp Val Gln Gly Val Ile Gln Met Leu Thr
1               5                   10                  15

<210> SEQ ID NO 561
<211> LENGTH: 15
<212> TYPE: PRT
<213> ORGANISM: Unknown
<220> FEATURE:
<223> OTHER INFORMATION: Shrimp peptide

<400> SEQUENCE: 561

Asp Val Gln Gly Val Ile Gln Met Leu Thr Ala Gly Gly Gly Asp
1               5                   10                  15

<210> SEQ ID NO 562
<211> LENGTH: 15
<212> TYPE: PRT
<213> ORGANISM: Unknown
<220> FEATURE:
<223> OTHER INFORMATION: Shrimp peptide

<400> SEQUENCE: 562

Ile Gln Met Leu Thr Ala Gly Gly Gly Asp Asp Ala Ala Ala Glu
1               5                   10                  15

<210> SEQ ID NO 563
<211> LENGTH: 12
<212> TYPE: PRT
<213> ORGANISM: Unknown
<220> FEATURE:
<223> OTHER INFORMATION: Shrimp peptide

<400> SEQUENCE: 563

Ala Gly Gly Gly Asp Asp Ala Ala Ala Glu Glu Ala
1               5                   10

<210> SEQ ID NO 564
<211> LENGTH: 15
<212> TYPE: PRT
<213> ORGANISM: Unknown
<220> FEATURE:
<223> OTHER INFORMATION: Shrimp peptide

<400> SEQUENCE: 564

Met Ala Tyr Ser Trp Asp Asn Arg Val Lys Tyr Val Val Arg Tyr
1               5                   10                  15

<210> SEQ ID NO 565
<211> LENGTH: 15
<212> TYPE: PRT
<213> ORGANISM: Unknown
<220> FEATURE:
<223> OTHER INFORMATION: Shrimp peptide

<400> SEQUENCE: 565

Asp Asn Arg Val Lys Tyr Val Val Arg Tyr Met Tyr Asp Ile Asp
1               5                   10                  15

<210> SEQ ID NO 566
<211> LENGTH: 15
<212> TYPE: PRT
<213> ORGANISM: Unknown
```

```
<220> FEATURE:
<223> OTHER INFORMATION: Shrimp peptide

<400> SEQUENCE: 566

Tyr Val Val Arg Tyr Met Tyr Asp Ile Asp Asn Asn Gly Phe Leu
1               5                   10                  15

<210> SEQ ID NO 567
<211> LENGTH: 15
<212> TYPE: PRT
<213> ORGANISM: Unknown
<220> FEATURE:
<223> OTHER INFORMATION: Shrimp peptide

<400> SEQUENCE: 567

Met Tyr Asp Ile Asp Asn Asn Gly Phe Leu Asp Lys Asn Asp Phe
1               5                   10                  15

<210> SEQ ID NO 568
<211> LENGTH: 15
<212> TYPE: PRT
<213> ORGANISM: Unknown
<220> FEATURE:
<223> OTHER INFORMATION: Shrimp peptide

<400> SEQUENCE: 568

Asn Asn Gly Phe Leu Asp Lys Asn Asp Phe Glu Cys Leu Ala Val
1               5                   10                  15

<210> SEQ ID NO 569
<211> LENGTH: 15
<212> TYPE: PRT
<213> ORGANISM: Unknown
<220> FEATURE:
<223> OTHER INFORMATION: Shrimp peptide

<400> SEQUENCE: 569

Asp Lys Asn Asp Phe Glu Cys Leu Ala Val Arg Asn Thr Leu Ile
1               5                   10                  15

<210> SEQ ID NO 570
<211> LENGTH: 15
<212> TYPE: PRT
<213> ORGANISM: Unknown
<220> FEATURE:
<223> OTHER INFORMATION: Shrimp peptide

<400> SEQUENCE: 570

Glu Cys Leu Ala Val Arg Asn Thr Leu Ile Glu Gly Arg Gly Glu
1               5                   10                  15

<210> SEQ ID NO 571
<211> LENGTH: 15
<212> TYPE: PRT
<213> ORGANISM: Unknown
<220> FEATURE:
<223> OTHER INFORMATION: Shrimp peptide

<400> SEQUENCE: 571

Arg Asn Thr Leu Ile Glu Gly Arg Gly Glu Phe Ser Ala Asp Ala
1               5                   10                  15

<210> SEQ ID NO 572
<211> LENGTH: 15
<212> TYPE: PRT
<213> ORGANISM: Unknown
<220> FEATURE:
```

```
<223> OTHER INFORMATION: Shrimp peptide

<400> SEQUENCE: 572

Glu Gly Arg Gly Glu Phe Ser Ala Asp Ala Tyr Ala Asn Asn Gln
1               5                   10                  15

<210> SEQ ID NO 573
<211> LENGTH: 15
<212> TYPE: PRT
<213> ORGANISM: Unknown
<220> FEATURE:
<223> OTHER INFORMATION: Shrimp peptide

<400> SEQUENCE: 573

Phe Ser Ala Asp Ala Tyr Ala Asn Asn Gln Lys Ile Met Arg Asn
1               5                   10                  15

<210> SEQ ID NO 574
<211> LENGTH: 15
<212> TYPE: PRT
<213> ORGANISM: Unknown
<220> FEATURE:
<223> OTHER INFORMATION: Shrimp peptide

<400> SEQUENCE: 574

Tyr Ala Asn Asn Gln Lys Ile Met Arg Asn Leu Trp Asn Glu Ile
1               5                   10                  15

<210> SEQ ID NO 575
<211> LENGTH: 15
<212> TYPE: PRT
<213> ORGANISM: Unknown
<220> FEATURE:
<223> OTHER INFORMATION: Shrimp peptide

<400> SEQUENCE: 575

Lys Ile Met Arg Asn Leu Trp Asn Glu Ile Ala Glu Leu Ala Asp
1               5                   10                  15

<210> SEQ ID NO 576
<211> LENGTH: 15
<212> TYPE: PRT
<213> ORGANISM: Unknown
<220> FEATURE:
<223> OTHER INFORMATION: Shrimp peptide

<400> SEQUENCE: 576

Leu Trp Asn Glu Ile Ala Glu Leu Ala Asp Phe Asn Lys Asp Gly
1               5                   10                  15

<210> SEQ ID NO 577
<211> LENGTH: 15
<212> TYPE: PRT
<213> ORGANISM: Unknown
<220> FEATURE:
<223> OTHER INFORMATION: Shrimp peptide

<400> SEQUENCE: 577

Ala Glu Leu Ala Asp Phe Asn Lys Asp Gly Glu Val Thr Val Asp
1               5                   10                  15

<210> SEQ ID NO 578
<211> LENGTH: 15
<212> TYPE: PRT
<213> ORGANISM: Unknown
<220> FEATURE:
<223> OTHER INFORMATION: Shrimp peptide
```

<400> SEQUENCE: 578

Phe Asn Lys Asp Gly Glu Val Thr Val Asp Glu Phe Lys Gln Ala
1               5                   10                  15

<210> SEQ ID NO 579
<211> LENGTH: 15
<212> TYPE: PRT
<213> ORGANISM: Unknown
<220> FEATURE:
<223> OTHER INFORMATION: Shrimp peptide

<400> SEQUENCE: 579

Glu Val Thr Val Asp Glu Phe Lys Gln Ala Val Gln Lys His Cys
1               5                   10                  15

<210> SEQ ID NO 580
<211> LENGTH: 15
<212> TYPE: PRT
<213> ORGANISM: Unknown
<220> FEATURE:
<223> OTHER INFORMATION: Shrimp peptide

<400> SEQUENCE: 580

Glu Phe Lys Gln Ala Val Gln Lys His Cys Gln Gly Lys Lys Tyr
1               5                   10                  15

<210> SEQ ID NO 581
<211> LENGTH: 15
<212> TYPE: PRT
<213> ORGANISM: Unknown
<220> FEATURE:
<223> OTHER INFORMATION: Shrimp peptide

<400> SEQUENCE: 581

Val Gln Lys His Cys Gln Gly Lys Lys Tyr Gly Asp Phe Pro Gly
1               5                   10                  15

<210> SEQ ID NO 582
<211> LENGTH: 15
<212> TYPE: PRT
<213> ORGANISM: Unknown
<220> FEATURE:
<223> OTHER INFORMATION: Shrimp peptide

<400> SEQUENCE: 582

Gln Gly Lys Lys Tyr Gly Asp Phe Pro Gly Ala Phe Lys Val Phe
1               5                   10                  15

<210> SEQ ID NO 583
<211> LENGTH: 15
<212> TYPE: PRT
<213> ORGANISM: Unknown
<220> FEATURE:
<223> OTHER INFORMATION: Shrimp peptide

<400> SEQUENCE: 583

Gly Asp Phe Pro Gly Ala Phe Lys Val Phe Ile Ala Asn Gln Phe
1               5                   10                  15

<210> SEQ ID NO 584
<211> LENGTH: 15
<212> TYPE: PRT
<213> ORGANISM: Unknown
<220> FEATURE:
<223> OTHER INFORMATION: Shrimp peptide

```
<400> SEQUENCE: 584

Ala Phe Lys Val Phe Ile Ala Asn Gln Phe Lys Ala Ile Asp Val
1               5                   10                  15

<210> SEQ ID NO 585
<211> LENGTH: 15
<212> TYPE: PRT
<213> ORGANISM: Unknown
<220> FEATURE:
<223> OTHER INFORMATION: Shrimp peptide

<400> SEQUENCE: 585

Ile Ala Asn Gln Phe Lys Ala Ile Asp Val Asn Gly Asp Gly Lys
1               5                   10                  15

<210> SEQ ID NO 586
<211> LENGTH: 15
<212> TYPE: PRT
<213> ORGANISM: Unknown
<220> FEATURE:
<223> OTHER INFORMATION: Shrimp peptide

<400> SEQUENCE: 586

Lys Ala Ile Asp Val Asn Gly Asp Gly Lys Val Gly Leu Asp Glu
1               5                   10                  15

<210> SEQ ID NO 587
<211> LENGTH: 15
<212> TYPE: PRT
<213> ORGANISM: Unknown
<220> FEATURE:
<223> OTHER INFORMATION: Shrimp peptide

<400> SEQUENCE: 587

Asn Gly Asp Gly Lys Val Gly Leu Asp Glu Tyr Arg Leu Asp Cys
1               5                   10                  15

<210> SEQ ID NO 588
<211> LENGTH: 15
<212> TYPE: PRT
<213> ORGANISM: Unknown
<220> FEATURE:
<223> OTHER INFORMATION: Shrimp peptide

<400> SEQUENCE: 588

Val Gly Leu Asp Glu Tyr Arg Leu Asp Cys Ile Thr Arg Ser Ala
1               5                   10                  15

<210> SEQ ID NO 589
<211> LENGTH: 15
<212> TYPE: PRT
<213> ORGANISM: Unknown
<220> FEATURE:
<223> OTHER INFORMATION: Shrimp peptide

<400> SEQUENCE: 589

Tyr Arg Leu Asp Cys Ile Thr Arg Ser Ala Phe Ala Glu Val Lys
1               5                   10                  15

<210> SEQ ID NO 590
<211> LENGTH: 15
<212> TYPE: PRT
<213> ORGANISM: Unknown
<220> FEATURE:
<223> OTHER INFORMATION: Shrimp peptide

<400> SEQUENCE: 590
```

```
Ile Thr Arg Ser Ala Phe Ala Glu Val Lys Glu Ile Asp Asp Ala
1               5                   10                  15
```

<210> SEQ ID NO 591
<211> LENGTH: 15
<212> TYPE: PRT
<213> ORGANISM: Unknown
<220> FEATURE:
<223> OTHER INFORMATION: Shrimp peptide

<400> SEQUENCE: 591

```
Phe Ala Glu Val Lys Glu Ile Asp Asp Ala Tyr Asn Lys Leu Thr
1               5                   10                  15
```

<210> SEQ ID NO 592
<211> LENGTH: 15
<212> TYPE: PRT
<213> ORGANISM: Unknown
<220> FEATURE:
<223> OTHER INFORMATION: Shrimp peptide

<400> SEQUENCE: 592

```
Glu Ile Asp Asp Ala Tyr Asn Lys Leu Thr Thr Glu Asp Asp Arg
1               5                   10                  15
```

<210> SEQ ID NO 593
<211> LENGTH: 15
<212> TYPE: PRT
<213> ORGANISM: Unknown
<220> FEATURE:
<223> OTHER INFORMATION: Shrimp peptide

<400> SEQUENCE: 593

```
Tyr Asn Lys Leu Thr Thr Glu Asp Asp Arg Lys Ala Gly Gly Leu
1               5                   10                  15
```

<210> SEQ ID NO 594
<211> LENGTH: 15
<212> TYPE: PRT
<213> ORGANISM: Unknown
<220> FEATURE:
<223> OTHER INFORMATION: Shrimp peptide

<400> SEQUENCE: 594

```
Thr Glu Asp Asp Arg Lys Ala Gly Gly Leu Thr Leu Glu Arg Tyr
1               5                   10                  15
```

<210> SEQ ID NO 595
<211> LENGTH: 15
<212> TYPE: PRT
<213> ORGANISM: Unknown
<220> FEATURE:
<223> OTHER INFORMATION: Shrimp peptide

<400> SEQUENCE: 595

```
Lys Ala Gly Gly Leu Thr Leu Glu Arg Tyr Gln Asp Leu Tyr Ala
1               5                   10                  15
```

<210> SEQ ID NO 596
<211> LENGTH: 15
<212> TYPE: PRT
<213> ORGANISM: Unknown
<220> FEATURE:
<223> OTHER INFORMATION: Shrimp peptide

<400> SEQUENCE: 596

Thr Leu Glu Arg Tyr Gln Asp Leu Tyr Ala Gln Phe Ile Ser Asn
1               5                   10                  15

<210> SEQ ID NO 597
<211> LENGTH: 15
<212> TYPE: PRT
<213> ORGANISM: Unknown
<220> FEATURE:
<223> OTHER INFORMATION: Shrimp peptide

<400> SEQUENCE: 597

Gln Asp Leu Tyr Ala Gln Phe Ile Ser Asn Pro Asp Glu Ser Cys
1               5                   10                  15

<210> SEQ ID NO 598
<211> LENGTH: 15
<212> TYPE: PRT
<213> ORGANISM: Unknown
<220> FEATURE:
<223> OTHER INFORMATION: Shrimp peptide

<400> SEQUENCE: 598

Gln Phe Ile Ser Asn Pro Asp Glu Ser Cys Ser Ala Cys Tyr Leu
1               5                   10                  15

<210> SEQ ID NO 599
<211> LENGTH: 15
<212> TYPE: PRT
<213> ORGANISM: Unknown
<220> FEATURE:
<223> OTHER INFORMATION: Shrimp peptide

<400> SEQUENCE: 599

Pro Asp Glu Ser Cys Ser Ala Cys Tyr Leu Phe Gly Pro Leu Lys
1               5                   10                  15

<210> SEQ ID NO 600
<211> LENGTH: 13
<212> TYPE: PRT
<213> ORGANISM: Unknown
<220> FEATURE:
<223> OTHER INFORMATION: Shrimp peptide

<400> SEQUENCE: 600

Ser Ala Cys Tyr Leu Phe Gly Pro Leu Lys Val Val Gln
1               5                   10

<210> SEQ ID NO 601
<211> LENGTH: 15
<212> TYPE: PRT
<213> ORGANISM: Unknown
<220> FEATURE:
<223> OTHER INFORMATION: Shrimp peptide

<400> SEQUENCE: 601

Met Asp Ala Ile Lys Lys Lys Met Gln Ala Met Lys Leu Glu Lys
1               5                   10                  15

<210> SEQ ID NO 602
<211> LENGTH: 15
<212> TYPE: PRT
<213> ORGANISM: Unknown
<220> FEATURE:
<223> OTHER INFORMATION: Shrimp peptide

<400> SEQUENCE: 602

Lys Lys Met Gln Ala Met Lys Leu Glu Lys Asp Asn Ala Met Asp

```
<210> SEQ ID NO 603
<211> LENGTH: 15
<212> TYPE: PRT
<213> ORGANISM: Unknown
<220> FEATURE:
<223> OTHER INFORMATION: Shrimp peptide

<400> SEQUENCE: 603

Met Lys Leu Glu Lys Asp Asn Ala Met Asp Arg Ala Asp Thr Leu
1               5                   10                  15

<210> SEQ ID NO 604
<211> LENGTH: 15
<212> TYPE: PRT
<213> ORGANISM: Unknown
<220> FEATURE:
<223> OTHER INFORMATION: Shrimp peptide

<400> SEQUENCE: 604

Asp Asn Ala Met Asp Arg Ala Asp Thr Leu Glu Gln Gln Asn Lys
1               5                   10                  15

<210> SEQ ID NO 605
<211> LENGTH: 15
<212> TYPE: PRT
<213> ORGANISM: Unknown
<220> FEATURE:
<223> OTHER INFORMATION: Shrimp peptide

<400> SEQUENCE: 605

Arg Ala Asp Thr Leu Glu Gln Gln Asn Lys Glu Ala Asn Asn Arg
1               5                   10                  15

<210> SEQ ID NO 606
<211> LENGTH: 15
<212> TYPE: PRT
<213> ORGANISM: Unknown
<220> FEATURE:
<223> OTHER INFORMATION: Shrimp peptide

<400> SEQUENCE: 606

Glu Gln Gln Asn Lys Glu Ala Asn Asn Arg Ala Glu Lys Ser Glu
1               5                   10                  15

<210> SEQ ID NO 607
<211> LENGTH: 15
<212> TYPE: PRT
<213> ORGANISM: Unknown
<220> FEATURE:
<223> OTHER INFORMATION: Shrimp peptide

<400> SEQUENCE: 607

Glu Ala Asn Asn Arg Ala Glu Lys Ser Glu Glu Glu Val His Asn
1               5                   10                  15

<210> SEQ ID NO 608
<211> LENGTH: 15
<212> TYPE: PRT
<213> ORGANISM: Unknown
<220> FEATURE:
<223> OTHER INFORMATION: Shrimp peptide

<400> SEQUENCE: 608

Ala Glu Lys Ser Glu Glu Glu Val His Asn Leu Gln Lys Arg Met
1               5                   10                  15
```

```
<210> SEQ ID NO 609
<211> LENGTH: 15
<212> TYPE: PRT
<213> ORGANISM: Unknown
<220> FEATURE:
<223> OTHER INFORMATION: Shrimp peptide

<400> SEQUENCE: 609

Glu Glu Val His Asn Leu Gln Lys Arg Met Gln Gln Leu Glu Asn
1               5                   10                  15

<210> SEQ ID NO 610
<211> LENGTH: 15
<212> TYPE: PRT
<213> ORGANISM: Unknown
<220> FEATURE:
<223> OTHER INFORMATION: Shrimp peptide

<400> SEQUENCE: 610

Leu Gln Lys Arg Met Gln Gln Leu Glu Asn Asp Leu Asp Gln Val
1               5                   10                  15

<210> SEQ ID NO 611
<211> LENGTH: 15
<212> TYPE: PRT
<213> ORGANISM: Unknown
<220> FEATURE:
<223> OTHER INFORMATION: Shrimp peptide

<400> SEQUENCE: 611

Gln Gln Leu Glu Asn Asp Leu Asp Gln Val Gln Glu Ser Leu Leu
1               5                   10                  15

<210> SEQ ID NO 612
<211> LENGTH: 15
<212> TYPE: PRT
<213> ORGANISM: Unknown
<220> FEATURE:
<223> OTHER INFORMATION: Shrimp peptide

<400> SEQUENCE: 612

Asp Leu Asp Gln Val Gln Glu Ser Leu Leu Lys Ala Asn Ile Gln
1               5                   10                  15

<210> SEQ ID NO 613
<211> LENGTH: 15
<212> TYPE: PRT
<213> ORGANISM: Unknown
<220> FEATURE:
<223> OTHER INFORMATION: Shrimp peptide

<400> SEQUENCE: 613

Gln Glu Ser Leu Leu Lys Ala Asn Ile Gln Leu Val Glu Lys Asp
1               5                   10                  15

<210> SEQ ID NO 614
<211> LENGTH: 15
<212> TYPE: PRT
<213> ORGANISM: Unknown
<220> FEATURE:
<223> OTHER INFORMATION: Shrimp peptide

<400> SEQUENCE: 614

Lys Ala Asn Ile Gln Leu Val Glu Lys Asp Lys Ala Leu Ser Asn
1               5                   10                  15
```

```
<210> SEQ ID NO 615
<211> LENGTH: 15
<212> TYPE: PRT
<213> ORGANISM: Unknown
<220> FEATURE:
<223> OTHER INFORMATION: Shrimp peptide

<400> SEQUENCE: 615

Leu Val Glu Lys Asp Lys Ala Leu Ser Asn Ala Glu Gly Glu Val
1               5                   10                  15

<210> SEQ ID NO 616
<211> LENGTH: 15
<212> TYPE: PRT
<213> ORGANISM: Unknown
<220> FEATURE:
<223> OTHER INFORMATION: Shrimp peptide

<400> SEQUENCE: 616

Lys Ala Leu Ser Asn Ala Glu Gly Glu Val Ala Ala Leu Asn Arg
1               5                   10                  15

<210> SEQ ID NO 617
<211> LENGTH: 15
<212> TYPE: PRT
<213> ORGANISM: Unknown
<220> FEATURE:
<223> OTHER INFORMATION: Shrimp peptide

<400> SEQUENCE: 617

Ala Glu Gly Glu Val Ala Ala Leu Asn Arg Arg Ile Gln Leu Leu
1               5                   10                  15

<210> SEQ ID NO 618
<211> LENGTH: 15
<212> TYPE: PRT
<213> ORGANISM: Unknown
<220> FEATURE:
<223> OTHER INFORMATION: Shrimp peptide

<400> SEQUENCE: 618

Ala Ala Leu Asn Arg Arg Ile Gln Leu Leu Glu Glu Asp Leu Glu
1               5                   10                  15

<210> SEQ ID NO 619
<211> LENGTH: 15
<212> TYPE: PRT
<213> ORGANISM: Unknown
<220> FEATURE:
<223> OTHER INFORMATION: Shrimp peptide

<400> SEQUENCE: 619

Arg Ile Gln Leu Leu Glu Glu Asp Leu Glu Arg Ser Glu Glu Arg
1               5                   10                  15

<210> SEQ ID NO 620
<211> LENGTH: 15
<212> TYPE: PRT
<213> ORGANISM: Unknown
<220> FEATURE:
<223> OTHER INFORMATION: Shrimp peptide

<400> SEQUENCE: 620

Glu Glu Asp Leu Glu Arg Ser Glu Glu Arg Leu Asn Thr Ala Thr
1               5                   10                  15
```

```
<210> SEQ ID NO 621
<211> LENGTH: 15
<212> TYPE: PRT
<213> ORGANISM: Unknown
<220> FEATURE:
<223> OTHER INFORMATION: Shrimp peptide

<400> SEQUENCE: 621

Arg Ser Glu Glu Arg Leu Asn Thr Ala Thr Thr Lys Leu Ala Glu
1               5                   10                  15

<210> SEQ ID NO 622
<211> LENGTH: 15
<212> TYPE: PRT
<213> ORGANISM: Unknown
<220> FEATURE:
<223> OTHER INFORMATION: Shrimp peptide

<400> SEQUENCE: 622

Leu Asn Thr Ala Thr Thr Lys Leu Ala Glu Ala Ser Gln Ala Ala
1               5                   10                  15

<210> SEQ ID NO 623
<211> LENGTH: 15
<212> TYPE: PRT
<213> ORGANISM: Unknown
<220> FEATURE:
<223> OTHER INFORMATION: Shrimp peptide

<400> SEQUENCE: 623

Thr Lys Leu Ala Glu Ala Ser Gln Ala Ala Asp Glu Ser Glu Arg
1               5                   10                  15

<210> SEQ ID NO 624
<211> LENGTH: 15
<212> TYPE: PRT
<213> ORGANISM: Unknown
<220> FEATURE:
<223> OTHER INFORMATION: Shrimp peptide

<400> SEQUENCE: 624

Ala Ser Gln Ala Ala Asp Glu Ser Glu Arg Met Arg Lys Val Leu
1               5                   10                  15

<210> SEQ ID NO 625
<211> LENGTH: 15
<212> TYPE: PRT
<213> ORGANISM: Unknown
<220> FEATURE:
<223> OTHER INFORMATION: Shrimp peptide

<400> SEQUENCE: 625

Asp Glu Ser Glu Arg Met Arg Lys Val Leu Glu Asn Arg Ser Leu
1               5                   10                  15

<210> SEQ ID NO 626
<211> LENGTH: 15
<212> TYPE: PRT
<213> ORGANISM: Unknown
<220> FEATURE:
<223> OTHER INFORMATION: Shrimp peptide

<400> SEQUENCE: 626

Met Arg Lys Val Leu Glu Asn Arg Ser Leu Ser Asp Glu Glu Arg
1               5                   10                  15

<210> SEQ ID NO 627
```

```
<211> LENGTH: 15
<212> TYPE: PRT
<213> ORGANISM: Unknown
<220> FEATURE:
<223> OTHER INFORMATION: Shrimp peptide

<400> SEQUENCE: 627

Glu Asn Arg Ser Leu Ser Asp Glu Glu Arg Met Asp Ala Leu Glu
1               5                   10                  15

<210> SEQ ID NO 628
<211> LENGTH: 15
<212> TYPE: PRT
<213> ORGANISM: Unknown
<220> FEATURE:
<223> OTHER INFORMATION: Shrimp peptide

<400> SEQUENCE: 628

Ser Asp Glu Glu Arg Met Asp Ala Leu Glu Asn Gln Leu Lys Glu
1               5                   10                  15

<210> SEQ ID NO 629
<211> LENGTH: 15
<212> TYPE: PRT
<213> ORGANISM: Unknown
<220> FEATURE:
<223> OTHER INFORMATION: Shrimp peptide

<400> SEQUENCE: 629

Met Asp Ala Leu Glu Asn Gln Leu Lys Glu Ala Arg Phe Leu Ala
1               5                   10                  15

<210> SEQ ID NO 630
<211> LENGTH: 15
<212> TYPE: PRT
<213> ORGANISM: Unknown
<220> FEATURE:
<223> OTHER INFORMATION: Shrimp peptide

<400> SEQUENCE: 630

Asn Gln Leu Lys Glu Ala Arg Phe Leu Ala Glu Glu Ala Asp Arg
1               5                   10                  15

<210> SEQ ID NO 631
<211> LENGTH: 15
<212> TYPE: PRT
<213> ORGANISM: Unknown
<220> FEATURE:
<223> OTHER INFORMATION: Shrimp peptide

<400> SEQUENCE: 631

Ala Arg Phe Leu Ala Glu Glu Ala Asp Arg Lys Tyr Asp Glu Val
1               5                   10                  15

<210> SEQ ID NO 632
<211> LENGTH: 15
<212> TYPE: PRT
<213> ORGANISM: Unknown
<220> FEATURE:
<223> OTHER INFORMATION: Shrimp peptide

<400> SEQUENCE: 632

Glu Glu Ala Asp Arg Lys Tyr Asp Glu Val Ala Arg Lys Leu Ala
1               5                   10                  15

<210> SEQ ID NO 633
<211> LENGTH: 15
```

```
<212> TYPE: PRT
<213> ORGANISM: Unknown
<220> FEATURE:
<223> OTHER INFORMATION: Shrimp peptide

<400> SEQUENCE: 633

Lys Tyr Asp Glu Val Ala Arg Lys Leu Ala Met Val Glu Ala Asp
1               5                   10                  15

<210> SEQ ID NO 634
<211> LENGTH: 15
<212> TYPE: PRT
<213> ORGANISM: Unknown
<220> FEATURE:
<223> OTHER INFORMATION: Shrimp peptide

<400> SEQUENCE: 634

Ala Arg Lys Leu Ala Met Val Glu Ala Asp Leu Glu Arg Ala Glu
1               5                   10                  15

<210> SEQ ID NO 635
<211> LENGTH: 15
<212> TYPE: PRT
<213> ORGANISM: Unknown
<220> FEATURE:
<223> OTHER INFORMATION: Shrimp peptide

<400> SEQUENCE: 635

Met Val Glu Ala Asp Leu Glu Arg Ala Glu Glu Arg Ala Glu Thr
1               5                   10                  15

<210> SEQ ID NO 636
<211> LENGTH: 15
<212> TYPE: PRT
<213> ORGANISM: Unknown
<220> FEATURE:
<223> OTHER INFORMATION: Shrimp peptide

<400> SEQUENCE: 636

Leu Glu Arg Ala Glu Glu Arg Ala Glu Thr Gly Glu Ser Lys Ile
1               5                   10                  15

<210> SEQ ID NO 637
<211> LENGTH: 15
<212> TYPE: PRT
<213> ORGANISM: Unknown
<220> FEATURE:
<223> OTHER INFORMATION: Shrimp peptide

<400> SEQUENCE: 637

Glu Arg Ala Glu Thr Gly Glu Ser Lys Ile Val Glu Leu Glu Glu
1               5                   10                  15

<210> SEQ ID NO 638
<211> LENGTH: 15
<212> TYPE: PRT
<213> ORGANISM: Unknown
<220> FEATURE:
<223> OTHER INFORMATION: Shrimp peptide

<400> SEQUENCE: 638

Gly Glu Ser Lys Ile Val Glu Leu Glu Glu Leu Arg Val Val
1               5                   10                  15

<210> SEQ ID NO 639
<211> LENGTH: 15
<212> TYPE: PRT
```

```
<213> ORGANISM: Unknown
<220> FEATURE:
<223> OTHER INFORMATION: Shrimp peptide

<400> SEQUENCE: 639

Val Glu Leu Glu Glu Leu Arg Val Val Gly Asn Asn Leu Lys
1               5                   10                  15

<210> SEQ ID NO 640
<211> LENGTH: 15
<212> TYPE: PRT
<213> ORGANISM: Unknown
<220> FEATURE:
<223> OTHER INFORMATION: Shrimp peptide

<400> SEQUENCE: 640

Glu Leu Arg Val Val Gly Asn Asn Leu Lys Ser Leu Glu Val Ser
1               5                   10                  15

<210> SEQ ID NO 641
<211> LENGTH: 15
<212> TYPE: PRT
<213> ORGANISM: Unknown
<220> FEATURE:
<223> OTHER INFORMATION: Shrimp peptide

<400> SEQUENCE: 641

Gly Asn Asn Leu Lys Ser Leu Glu Val Ser Glu Glu Lys Ala Asn
1               5                   10                  15

<210> SEQ ID NO 642
<211> LENGTH: 15
<212> TYPE: PRT
<213> ORGANISM: Unknown
<220> FEATURE:
<223> OTHER INFORMATION: Shrimp peptide

<400> SEQUENCE: 642

Ser Leu Glu Val Ser Glu Glu Lys Ala Asn Gln Arg Glu Glu Ala
1               5                   10                  15

<210> SEQ ID NO 643
<211> LENGTH: 15
<212> TYPE: PRT
<213> ORGANISM: Unknown
<220> FEATURE:
<223> OTHER INFORMATION: Shrimp peptide

<400> SEQUENCE: 643

Glu Glu Lys Ala Asn Gln Arg Glu Glu Ala Tyr Lys Glu Gln Ile
1               5                   10                  15

<210> SEQ ID NO 644
<211> LENGTH: 15
<212> TYPE: PRT
<213> ORGANISM: Unknown
<220> FEATURE:
<223> OTHER INFORMATION: Shrimp peptide

<400> SEQUENCE: 644

Gln Arg Glu Glu Ala Tyr Lys Glu Gln Ile Lys Thr Leu Thr Asn
1               5                   10                  15

<210> SEQ ID NO 645
<211> LENGTH: 15
<212> TYPE: PRT
<213> ORGANISM: Unknown
```

```
<220> FEATURE:
<223> OTHER INFORMATION: Shrimp peptide

<400> SEQUENCE: 645

Tyr Lys Glu Gln Ile Lys Thr Leu Thr Asn Lys Leu Lys Ala Ala
1               5                   10                  15

<210> SEQ ID NO 646
<211> LENGTH: 15
<212> TYPE: PRT
<213> ORGANISM: Unknown
<220> FEATURE:
<223> OTHER INFORMATION: Shrimp peptide

<400> SEQUENCE: 646

Lys Thr Leu Thr Asn Lys Leu Lys Ala Ala Glu Ala Arg Ala Glu
1               5                   10                  15

<210> SEQ ID NO 647
<211> LENGTH: 15
<212> TYPE: PRT
<213> ORGANISM: Unknown
<220> FEATURE:
<223> OTHER INFORMATION: Shrimp peptide

<400> SEQUENCE: 647

Lys Leu Lys Ala Ala Glu Ala Arg Ala Glu Phe Ala Glu Arg Ser
1               5                   10                  15

<210> SEQ ID NO 648
<211> LENGTH: 15
<212> TYPE: PRT
<213> ORGANISM: Unknown
<220> FEATURE:
<223> OTHER INFORMATION: Shrimp peptide

<400> SEQUENCE: 648

Glu Ala Arg Ala Glu Phe Ala Glu Arg Ser Val Gln Lys Leu Gln
1               5                   10                  15

<210> SEQ ID NO 649
<211> LENGTH: 15
<212> TYPE: PRT
<213> ORGANISM: Unknown
<220> FEATURE:
<223> OTHER INFORMATION: Shrimp peptide

<400> SEQUENCE: 649

Phe Ala Glu Arg Ser Val Gln Lys Leu Gln Lys Glu Val Asp Arg
1               5                   10                  15

<210> SEQ ID NO 650
<211> LENGTH: 15
<212> TYPE: PRT
<213> ORGANISM: Unknown
<220> FEATURE:
<223> OTHER INFORMATION: Shrimp peptide

<400> SEQUENCE: 650

Val Gln Lys Leu Gln Lys Glu Val Asp Arg Leu Glu Asp Glu Leu
1               5                   10                  15

<210> SEQ ID NO 651
<211> LENGTH: 15
<212> TYPE: PRT
<213> ORGANISM: Unknown
<220> FEATURE:
```

```
<223> OTHER INFORMATION: Shrimp peptide

<400> SEQUENCE: 651

Lys Glu Val Asp Arg Leu Glu Asp Glu Leu Val Asn Glu Lys Glu
1               5                   10                  15

<210> SEQ ID NO 652
<211> LENGTH: 15
<212> TYPE: PRT
<213> ORGANISM: Unknown
<220> FEATURE:
<223> OTHER INFORMATION: Shrimp peptide

<400> SEQUENCE: 652

Leu Glu Asp Glu Leu Val Asn Glu Lys Glu Lys Tyr Lys Ser Ile
1               5                   10                  15

<210> SEQ ID NO 653
<211> LENGTH: 15
<212> TYPE: PRT
<213> ORGANISM: Unknown
<220> FEATURE:
<223> OTHER INFORMATION: Shrimp peptide

<400> SEQUENCE: 653

Val Asn Glu Lys Glu Lys Tyr Lys Ser Ile Thr Asp Glu Leu Asp
1               5                   10                  15

<210> SEQ ID NO 654
<211> LENGTH: 15
<212> TYPE: PRT
<213> ORGANISM: Unknown
<220> FEATURE:
<223> OTHER INFORMATION: Shrimp peptide

<400> SEQUENCE: 654

Lys Tyr Lys Ser Ile Thr Asp Glu Leu Asp Gln Thr Phe Ser Glu
1               5                   10                  15

<210> SEQ ID NO 655
<211> LENGTH: 14
<212> TYPE: PRT
<213> ORGANISM: Unknown
<220> FEATURE:
<223> OTHER INFORMATION: Shrimp peptide

<400> SEQUENCE: 655

Thr Asp Glu Leu Asp Gln Thr Phe Ser Glu Leu Ser Gly Tyr
1               5                   10

<210> SEQ ID NO 656
<211> LENGTH: 15
<212> TYPE: PRT
<213> ORGANISM: Unknown
<220> FEATURE:
<223> OTHER INFORMATION: Shrimp peptide

<400> SEQUENCE: 656

Met Asp Ser Leu Asp Glu Glu Gln Ile Glu Thr Leu Arg Lys Ala
1               5                   10                  15

<210> SEQ ID NO 657
<211> LENGTH: 15
<212> TYPE: PRT
<213> ORGANISM: Unknown
<220> FEATURE:
<223> OTHER INFORMATION: Shrimp peptide
```

<400> SEQUENCE: 657

Glu Glu Gln Ile Glu Thr Leu Arg Lys Ala Phe Asp Ser Phe Asp
1               5                   10                  15

<210> SEQ ID NO 658
<211> LENGTH: 15
<212> TYPE: PRT
<213> ORGANISM: Unknown
<220> FEATURE:
<223> OTHER INFORMATION: Shrimp peptide

<400> SEQUENCE: 658

Thr Leu Arg Lys Ala Phe Asp Ser Phe Asp Thr Glu Lys Thr Gly
1               5                   10                  15

<210> SEQ ID NO 659
<211> LENGTH: 15
<212> TYPE: PRT
<213> ORGANISM: Unknown
<220> FEATURE:
<223> OTHER INFORMATION: Shrimp peptide

<400> SEQUENCE: 659

Phe Asp Ser Phe Asp Thr Glu Lys Thr Gly Ser Ile Thr Ala Glu
1               5                   10                  15

<210> SEQ ID NO 660
<211> LENGTH: 15
<212> TYPE: PRT
<213> ORGANISM: Unknown
<220> FEATURE:
<223> OTHER INFORMATION: Shrimp peptide

<400> SEQUENCE: 660

Thr Glu Lys Thr Gly Ser Ile Thr Ala Glu Thr Ile Ala Thr Ile
1               5                   10                  15

<210> SEQ ID NO 661
<211> LENGTH: 15
<212> TYPE: PRT
<213> ORGANISM: Unknown
<220> FEATURE:
<223> OTHER INFORMATION: Shrimp peptide

<400> SEQUENCE: 661

Ser Ile Thr Ala Glu Thr Ile Ala Thr Ile Met Arg Met Met Gly
1               5                   10                  15

<210> SEQ ID NO 662
<211> LENGTH: 15
<212> TYPE: PRT
<213> ORGANISM: Unknown
<220> FEATURE:
<223> OTHER INFORMATION: Shrimp peptide

<400> SEQUENCE: 662

Thr Ile Ala Thr Ile Met Arg Met Met Gly Val Lys Ile Ser Glu
1               5                   10                  15

<210> SEQ ID NO 663
<211> LENGTH: 15
<212> TYPE: PRT
<213> ORGANISM: Unknown
<220> FEATURE:
<223> OTHER INFORMATION: Shrimp peptide

```
<400> SEQUENCE: 663

Met Arg Met Met Gly Val Lys Ile Ser Glu Lys Asn Leu Gln Glu
1               5                   10                  15

<210> SEQ ID NO 664
<211> LENGTH: 15
<212> TYPE: PRT
<213> ORGANISM: Unknown
<220> FEATURE:
<223> OTHER INFORMATION: Shrimp peptide

<400> SEQUENCE: 664

Val Lys Ile Ser Glu Lys Asn Leu Gln Glu Ala Ile Ala Glu Thr
1               5                   10                  15

<210> SEQ ID NO 665
<211> LENGTH: 15
<212> TYPE: PRT
<213> ORGANISM: Unknown
<220> FEATURE:
<223> OTHER INFORMATION: Shrimp peptide

<400> SEQUENCE: 665

Lys Asn Leu Gln Glu Ala Ile Ala Glu Thr Asp Glu Asp Gly Ser
1               5                   10                  15

<210> SEQ ID NO 666
<211> LENGTH: 15
<212> TYPE: PRT
<213> ORGANISM: Unknown
<220> FEATURE:
<223> OTHER INFORMATION: Shrimp peptide

<400> SEQUENCE: 666

Ala Ile Ala Glu Thr Asp Glu Asp Gly Ser Gly Leu Leu Glu Phe
1               5                   10                  15

<210> SEQ ID NO 667
<211> LENGTH: 15
<212> TYPE: PRT
<213> ORGANISM: Unknown
<220> FEATURE:
<223> OTHER INFORMATION: Shrimp peptide

<400> SEQUENCE: 667

Asp Glu Asp Gly Ser Gly Leu Leu Glu Phe Glu Glu Phe Val Glu
1               5                   10                  15

<210> SEQ ID NO 668
<211> LENGTH: 15
<212> TYPE: PRT
<213> ORGANISM: Unknown
<220> FEATURE:
<223> OTHER INFORMATION: Shrimp peptide

<400> SEQUENCE: 668

Gly Leu Leu Glu Phe Glu Glu Phe Val Glu Leu Ser Ala Lys Phe
1               5                   10                  15

<210> SEQ ID NO 669
<211> LENGTH: 15
<212> TYPE: PRT
<213> ORGANISM: Unknown
<220> FEATURE:
<223> OTHER INFORMATION: Shrimp peptide

<400> SEQUENCE: 669
```

```
Glu Glu Phe Val Glu Leu Ser Ala Lys Phe Leu Ile Glu Glu Asp
1               5                   10                  15
```

<210> SEQ ID NO 670
<211> LENGTH: 15
<212> TYPE: PRT
<213> ORGANISM: Unknown
<220> FEATURE:
<223> OTHER INFORMATION: Shrimp peptide

<400> SEQUENCE: 670

```
Leu Ser Ala Lys Phe Leu Ile Glu Glu Asp Glu Glu Ala Leu Lys
1               5                   10                  15
```

<210> SEQ ID NO 671
<211> LENGTH: 15
<212> TYPE: PRT
<213> ORGANISM: Unknown
<220> FEATURE:
<223> OTHER INFORMATION: Shrimp peptide

<400> SEQUENCE: 671

```
Leu Ile Glu Glu Asp Glu Glu Ala Leu Lys Ala Glu Leu Arg Glu
1               5                   10                  15
```

<210> SEQ ID NO 672
<211> LENGTH: 15
<212> TYPE: PRT
<213> ORGANISM: Unknown
<220> FEATURE:
<223> OTHER INFORMATION: Shrimp peptide

<400> SEQUENCE: 672

```
Glu Glu Ala Leu Lys Ala Glu Leu Arg Glu Ala Phe Arg Ile Tyr
1               5                   10                  15
```

<210> SEQ ID NO 673
<211> LENGTH: 15
<212> TYPE: PRT
<213> ORGANISM: Unknown
<220> FEATURE:
<223> OTHER INFORMATION: Shrimp peptide

<400> SEQUENCE: 673

```
Ala Glu Leu Arg Glu Ala Phe Arg Ile Tyr Asp Lys Glu Gly Asn
1               5                   10                  15
```

<210> SEQ ID NO 674
<211> LENGTH: 15
<212> TYPE: PRT
<213> ORGANISM: Unknown
<220> FEATURE:
<223> OTHER INFORMATION: Shrimp peptide

<400> SEQUENCE: 674

```
Ala Phe Arg Ile Tyr Asp Lys Glu Gly Asn Gly Phe Ile Thr Thr
1               5                   10                  15
```

<210> SEQ ID NO 675
<211> LENGTH: 15
<212> TYPE: PRT
<213> ORGANISM: Unknown
<220> FEATURE:
<223> OTHER INFORMATION: Shrimp peptide

<400> SEQUENCE: 675

Asp Lys Glu Gly Asn Gly Phe Ile Thr Thr Asp Val Leu Lys Glu
1               5                   10                  15

<210> SEQ ID NO 676
<211> LENGTH: 15
<212> TYPE: PRT
<213> ORGANISM: Unknown
<220> FEATURE:
<223> OTHER INFORMATION: Shrimp peptide

<400> SEQUENCE: 676

Gly Phe Ile Thr Thr Asp Val Leu Lys Glu Ile Leu Ala Glu Leu
1               5                   10                  15

<210> SEQ ID NO 677
<211> LENGTH: 15
<212> TYPE: PRT
<213> ORGANISM: Unknown
<220> FEATURE:
<223> OTHER INFORMATION: Shrimp peptide

<400> SEQUENCE: 677

Asp Val Leu Lys Glu Ile Leu Ala Glu Leu Asp Pro Arg Leu Thr
1               5                   10                  15

<210> SEQ ID NO 678
<211> LENGTH: 15
<212> TYPE: PRT
<213> ORGANISM: Unknown
<220> FEATURE:
<223> OTHER INFORMATION: Shrimp peptide

<400> SEQUENCE: 678

Ile Leu Ala Glu Leu Asp Pro Arg Leu Thr Pro Ala Asp Leu Glu
1               5                   10                  15

<210> SEQ ID NO 679
<211> LENGTH: 15
<212> TYPE: PRT
<213> ORGANISM: Unknown
<220> FEATURE:
<223> OTHER INFORMATION: Shrimp peptide

<400> SEQUENCE: 679

Asp Pro Arg Leu Thr Pro Ala Asp Leu Glu Asn Ile Ile Glu Glu
1               5                   10                  15

<210> SEQ ID NO 680
<211> LENGTH: 15
<212> TYPE: PRT
<213> ORGANISM: Unknown
<220> FEATURE:
<223> OTHER INFORMATION: Shrimp peptide

<400> SEQUENCE: 680

Pro Ala Asp Leu Glu Asn Ile Ile Glu Glu Val Asp Glu Asp Gly
1               5                   10                  15

<210> SEQ ID NO 681
<211> LENGTH: 15
<212> TYPE: PRT
<213> ORGANISM: Unknown
<220> FEATURE:
<223> OTHER INFORMATION: Shrimp peptide

<400> SEQUENCE: 681

Asn Ile Ile Glu Glu Val Asp Glu Asp Gly Ser Gly Thr Leu Asp

```
<210> SEQ ID NO 682
<211> LENGTH: 15
<212> TYPE: PRT
<213> ORGANISM: Unknown
<220> FEATURE:
<223> OTHER INFORMATION: Shrimp peptide

<400> SEQUENCE: 682

Val Asp Glu Asp Gly Ser Gly Thr Leu Asp Phe Asp Glu Phe Met
1               5                   10                  15

<210> SEQ ID NO 683
<211> LENGTH: 15
<212> TYPE: PRT
<213> ORGANISM: Unknown
<220> FEATURE:
<223> OTHER INFORMATION: Shrimp peptide

<400> SEQUENCE: 683

Ser Gly Thr Leu Asp Phe Asp Glu Phe Met Glu Met Met Asn Gly
1               5                   10                  15
```

PEPTIDES, REAGENTS AND METHODS FOR DETECTING FOOD ALLERGY

CROSS REFERENCE TO SEQUENCE LISTING

The Sequence Listing created on Apr. 11, 2017, and identified as "DSC0056-00US2 ST25.txt" (146.9 KB) is hereby incorporated by reference.

TECHNICAL FIELD

The invention relates to peptide biomarkers for diagnosis of allergy and for determining whether an allergic subject is likely to outgrow the allergy. The invention also relates to diagnostic methods and diagnostic kits employing the peptide biomarkers.

BACKGROUND

Food allergies are a common problem among adults and children, and symptoms may range from mild oral pruritus to potentially life-threatening anaphylactic shock. Food allergies are currently diagnosed by skin prick testing or oral provocation, and measurement of serum levels of specific IgE and in some cases other serum antibodies, such as IgG4. These tests indicate the likelihood of clinical reactivity but do not distinguish the different phenotypes of food allergy or provide prognostic information. They also involve some level of risk to the patient. The relationship between current IgE testing and the actual clinical sensitivity of the patient is a weak one that is usually defined as a combination of reaction severity and the amount of allergen that provokes a reaction. Another limitation of current testing is the inability to determine whether or not pediatric patients will outgrow the allergy during childhood. In this case there is a positive but weak correlation between specific IgE level and the duration of clinical allergy.

More recently, it has been suggested that clinical reactivity to food allergens may correlate better with allergen-specific IgE on the epitope recognition level. It has been reported that patients with persistent or more severe allergic reactions recognize larger numbers of IgE epitopes, suggesting epitope mapping as an additional tool for allergy diagnosis and prediction. Spot membrane-based immunoassays have been used for epitope mapping. In this system, peptides are synthesized on the membrane and incubated with the patient's sera. The process requires a large number of peptides and is therefore error prone, time consuming, labor intensive, and expensive. Immunoassays in this format also require a large volume of patient serum.

Development of multiplex assay technologies, such as microarrays, and advances in peptide synthesis techniques have improved epitope mapping of food allergens. Immunoassays in microarray format can assay thousands of target peptides in parallel using small volumes of diluted serum, greatly reducing the cost and allowing for better replication and statistical approaches to the analysis. Unfortunately, the microarray-based test is not high through-put and it frequently requires multiple replicates to overcome limitations in reproducibility.

High-throughput assay formats have the advantage of rapidly processing multiple patient specimens in an automated fashion, and have been developed for application to multiplex screening methods. Bead-based multiplexing, such as the LUMINEX/xMAP technology, uses 5.6 µm polystyrene beads dyed with red and infrared fluorophores. Using different amounts of each of the two fluorophores, up to 500 different specific spectral signatures can be produced and theoretically up to 500 tests in a single reaction volume is possible. In the typical protein assay, antibodies are conjugated to the surface of the beads to capture the analyte of interest. Biotinylated detection antibodies specific to the analyte of interest are then bound to form an antibody-antigen sandwich. Interaction of biotin with a phycoerythrin-conjugated streptavidin (SA-PE) is used to label the complex. To detect the analyte, the beads are read on a dual-laser flow-based detection instrument. One laser classifies the bead according to the incorporated dyes and determines the analyte that is being detected. The second laser determines the magnitude of the PE-derived signal, which is in direct proportion to the amount of the bound analyte. Such assays reduce the amount of capture antibody and sample required compared to an ELISA plate assay, thus reducing the cost and conserving rare or difficult-to-obtain sample material. The dynamic range and sensitivity of the assay are also generally improved.

Cow's milk allergy (CMA) is one of the most common food allergies in children. It typically involves sensitivity to several of the component proteins of cow's milk. These include proteins in the casein fraction ($\alpha_{s-1}$-, $\alpha_{s-2}$-, $\beta$-, and $\kappa$-casein), $\alpha$-lactalbumin and $\beta$-lactoglobulin. Both conformational and sequential epitopes can elicit antibody responses. Although the majority of children eventually outgrow their CMA (i.e., they become clinically tolerant), some retain their sensitivity into later life. The mechanisms contributing to development of clinical tolerance are not well understood, but it is hypothesized that IgE antibodies of those with persistent CMA may recognize certain epitopes of cow's milk proteins that are not recognized by IgE antibodies from patients who are likely to outgrow their allergy.

Analysis of epitopes, such as sequential epitope recognition, can provide useful information concerning persistence of CMA. Peptide microarray results have shown a correlation with clinical features of milk allergy, i.e., patients with milk allergy and milk-tolerant patients evidenced different epitope recognition patterns. It was also demonstrated that changes in the relative binding of IgE and IgG4 to milk peptides correlated with the presence of allergy or with clinical improvement.

However, there remains a need to identify informative epitopes that are useful for diagnosing CMA and for predicting the clinical outcome of CMA. There also remains a need for new assay platforms that overcome the deficiencies of microarray immunoassays, and provide high-throughput, increased flexibility, reduced sample volume, and lower cost, with a similar workflow. The present invention addresses these needs.

SUMMARY

In a first embodiment, the invention relates to peptides containing allergenic epitopes of cow's milk proteins that are useful for diagnosis of CMA, for detecting development of clinical tolerance to cow's milk proteins, and for monitoring increases and decreases in the intensity of the allergic response.

In a specific aspect of the first embodiment, the allergenic epitope-containing peptides are a plurality of peptides selected from the group consisting of allergenic peptide epitopes of $\alpha$S1-casein, $\alpha$S2-casein, $\beta$-casein, $\beta$-lactoglobulin and $\kappa$-casein. In a further specific embodiment, the allergenic epitope-containing peptides are a plurality of peptides selected from among SEQ ID NOs:1-33:

AlphaS-1 Casein Peptides:

| | | |
|---|---|---|
| alphaS1-03 | KHQGLPQEVLNENLLRFFVA | SEQ ID NO: 1 |
| alphaS1-09 | VAPFPEVFGKEKVNELSKDI | SEQ ID NO: 2 |
| alphaS1-22 | SISSSEEIVPNSVEQKHIQK | SEQ ID NO: 3 |
| alphaS1-27 | KHIQKEDVPSERYLGYLEQL | SEQ ID NO: 4 |
| alphaS1-30 | SERYLGYLEQLLRLKKYKVP | SEQ ID NO: 5 |
| alphaS1-35 | KYKVPQLEIVPNSAEERLHS | SEQ ID NO: 6 |
| alphaS1-44 | QQKEPMIGVNQELAYFYPEL | SEQ ID NO: 7 |
| alphaS1-57 | LGTQYTDAPSFSDIPNPIGS | SEQ ID NO: 8 |
| alphaS1-61 | SDIPNPIGSENSEKTTMPLW | SEQ ID NO: 9 |

AlphaS-2 Casein Peptides:

| | | |
|---|---|---|
| alphaS2-08 | QEKNMAINPSKENLCSTFCK | SEQ ID NO: 10 |
| alphaS2-13 | STFCKEVVRNANEEEYSIGS | SEQ ID NO: 11 |
| alphaS2-26 | KHYQKALNEINQFYQKFPQY | SEQ ID NO: 12 |
| alphaS2-33 | QYLYQGPIVLNPWDQVKRNA | SEQ ID NO: 13 |
| alphaS2-56 | KISQRYQKFALPQYLKTVYQ | SEQ ID NO: 14 |
| alphaS2-60 | QYLKTVYQHQKAMKPWIQPK | SEQ ID NO: 15 |

Beta-Casein Peptides:

| | | |
|---|---|---|
| betacas-01 | RELEELNVPGEIVESLSSSE | SEQ ID NO: 16 |
| betacas-16 | QDKIHPFAQTQSLVYPFPGP | SEQ ID NO: 17 |
| betacas-18 | FAQTQSLVYPFPGPIPNSLP | SEQ ID NO: 18 |
| betacas-25 | NIPPLTQTPVVVPPFLQPEV | SEQ ID NO: 19 |
| betacas-33 | KVKEAMAPKHKEMPFPKYPV | SEQ ID NO: 20 |
| betacas-42 | SLTLTDVENLHLPLPLLQSW | SEQ ID NO: 21 |
| betacas-53 | FPPQSVLSLSQSKVLPVPQK | SEQ ID NO: 22 |
| betacas-58 | PVPQKAVPYPQRDMPIQAFL | SEQ ID NO: 23 |

Beta-Lactoglobulin Peptides:

| | | |
|---|---|---|
| betalac-14 | RVYVEELKPTPEGDLEILLQ | SEQ ID NO: 24 |
| betalac-22 | DECAQKKIIAEKTKIPAVFK | SEQ ID NO: 25 |
| betalac-41 | CLVRTPEVDDEALEKFDKAL | SEQ ID NO: 26 |
| betalac-43 | EVDDEALEKFDKALKALPMH | SEQ ID NO: 27 |

Kappa Casein Peptides:

| | | |
|---|---|---|
| kappacas-04 | RCEKDERFFSDKIAKYIPIQ | SEQ ID NO: 28 |
| kappacas-16 | KPVALINNQFLPYPYYAKPA | SEQ ID NO: 29 |
| kappacas-36 | MAIPPKKNQDKTEIPTINTI | SEQ ID NO: 30 |
| kappacas-44 | PTSTPTTEAVESTVATLEDS | SEQ ID NO: 31 |
| kappacas-49 | TLEDSPEVIESPPEINTVQV | SEQ ID NO: 32 |
| kappacas-21 | YAKPAAVRSPAQILQWQVLS | SEQ ID NO: 33 |

Peptides useful in methods for diagnosis of CMA, for detecting development of clinical tolerance to cow's milk proteins, and for detecting increases and decreases in the intensity of the allergy may also include peptides containing non-reactive epitopes of cow's milk proteins. These peptides are useful as negative controls. In specific aspects the peptides containing negative control epitopes are one or more peptides selected from the group consisting of non-reactive peptide epitopes of αS2-casein, β-casein, and β-lactoglobulin. In a further specific embodiment, the non-reactive epitope-containing peptides are one or more peptides selected from the group consisting of:

AlphaS-2 Peptides:

| | | |
|---|---|---|
| alphas2-42 | NREQLSTSEENSKKTVDMES | SEQ ID NO: 34 |

Beta-Casein Peptides:

| | | |
|---|---|---|
| betacas-09 | RINKKIEKFQSEEQQQTEDE | SEQ ID NO: 35 |

Beta-Lactoglobulin Peptides:

| | | |
|---|---|---|
| betalac-31 | KVLVLDTDYKKYLLVCMENS | SEQ ID NO: 36 |

In a second embodiment, the invention relates to methods for diagnosing CMA using a plurality (i.e., two or more) of the foregoing allergenic epitope-containing peptides. In specific aspects, CMA in a subject is diagnosed by a method comprising:
a) providing a plurality of peptides selected from among SEQ ID NOs:1-33, each peptide conjugated to a separately identifiable solid support;
b) contacting each solid support with serum obtained from the subject under conditions sufficient to permit binding of allergy-associated immunoglobulin (AAI) in the serum to the peptide on each solid support to form a peptide-AAI complex;
c) binding an AAI-specific labeling reagent to the peptide-AAI complex; and
d) analyzing binding of the labeling reagent to each peptide-AAI complex to identify peptides recognized by the AAI in the serum of the subject;
wherein recognition of at least one peptide by the AAI in the serum of the subject indicates that the subject is allergic to cow's milk.

In a further embodiment, the invention relates to methods for detecting development of clinical tolerance in a subject having CMA using a plurality of the foregoing allergenic epitope-containing peptides. In specific aspects, development of clinical tolerance to cow's milk in a subject having CMA is detected by a method comprising:
a) providing an initial profile of allergy associated immunoglobulin (AAI) reactivity in the subject's serum to a plurality of peptides selected from among SEQ ID NOs:1-33, wherein the initial profile defines an initial number of peptides recognized by AAI in the serum of the subject or an initial concentration of AAI in the serum of the subject that recognizes each peptide;
b) providing the plurality of peptides selected from among SEQ ID NOs:1-33, each peptide conjugated to a separately identifiable solid support
b) contacting each solid support with serum obtained from the subject at a time-point subsequent to the initial profile under conditions sufficient to permit binding of AAI in the serum to the peptide on each solid support to form a peptide-AAI complex;
c) binding an AAI-specific labeling reagent to the peptide-AAI complex; and
d) analyzing binding of the labeling reagent to each peptide-AAI complex to identify a subsequent number of peptides recognized by AAI in the serum of the subject or a subsequent concentration of AAI in the serum of the subject that recognizes each peptide;

wherein development of clinical tolerance to cow's milk is indicated when the subsequent number of peptides recognized by AAI in the serum of the subject is less than the initial number of peptides recognized by AAI in the serum of the subject, or when the subsequent concentration of AAI in the serum of the subject that recognizes at least one peptide is less than the initial concentration of AAI in the serum of the subject that recognizes the at least one peptide.

In another embodiment, the initial detection of development of clinical tolerance is used to predict if a patient will either develop a natural tolerance to the allergy or be responsive to therapy. In this embodiment, an allergic subject is exposed to the immunogen (immunotherapy) prior to analyzing the initial profile. If at the subsequent time-point there is a reduction of at least 2-fold in serum concentration of all AAIs that were highly reactive with peptides in the initial profile, it is likely that the subject will develop either clinical or natural tolerance to cow's milk. If at the subsequent time-point there is a reduction of at least 2-fold in serum concentration of fewer than all AAIs that were highly reactive with peptides in the initial profile, the subject is likely to develop only partial clinical or natural tolerance to cow's milk.

In an alternative embodiment, the methods of the invention can be used to detect an increase (or decrease) in the intensity of the allergic response to cow's milk (CMA intensity) in a subject over a period of time. In specific aspects, detection of an increase in intensity of the allergic response may correspond to development of CMA in a previously cow's milk-tolerant subject. Alternatively, detection of an increase in intensity of the allergic response may correspond to an increase in allergy intensity in a subject previously known to have CMA. Detection of a decrease in the intensity of the allergic response to cow's milk is an aspect of development of clinical tolerance to cow's milk proteins, as discussed above.

In specific aspects, an increase in intensity of allergy to cow's milk in a subject over time is detected by a method comprising:
 a) providing an initial profile of allergy associated immunoglobulin (AAI) reactivity in the subject's serum to a plurality of peptides selected from among SEQ ID NOs:1-33, wherein the initial profile defines an initial number of peptides recognized by AAI in the serum of the subject or an initial concentration of AAI in the serum of the subject that recognizes each peptide;
 b) providing the plurality of peptides selected from among SEQ ID NOs:1-33, each peptide conjugated to a separately identifiable solid support
 b) contacting each solid support with serum obtained from the subject at a time-point subsequent to the initial profile under conditions sufficient to permit binding of AAI in the serum to the peptide on each solid support to form a peptide-AAI complex;
 c) binding an AAI-specific labeling reagent to the peptide-AAI complex; and
 d) analyzing the binding of the labeling reagent to each peptide-AAI complex to identify a subsequent number of peptides recognized by AAI in the serum of the subject or a subsequent concentration of AAI in the serum of the subject that recognizes each peptide;
wherein an increase in the subsequent number of peptides recognized by AAI in the serum of the subject compared to the initial number of peptides recognized by AAI in the serum of the subject, or an increase in the subsequent concentration of AAI in the serum of the subject that recognizes at least one peptide compared to the initial concentration of AAI in the serum of the subject that recognizes the at least one peptide, indicates increased intensity of the allergic response to cow's milk in the subject.

Any of the foregoing embodiments and aspects of the methods of the invention may be in the form of a microarray immunoassay, wherein each of the plurality of allergenic epitope-containing peptides is bound to a separate well of a microtiter plate and reacted with serum to bind AAI. Bound AAI is detected by binding of an AAI specific labeling reagent, for example an anti-AAI antibody conjugated to a reporter moiety such as a fluorescent label. Fluorescence of the bound labeling reagent indicates presence of in the serum of antibody to the allergenic epitope contained in the peptide bound to the well. The plurality of allergenic epitope-containing peptides may also be used in a lateral flow immunoassay format, wherein each peptide is immobilized in a discrete area on a porous or chromatographic support, and the serum is wicked through the support to contact the peptides for binding of AAI to the peptides. In this assay, the AAI specific labeling reagent may comprise a chromophore or dye conjugated to anti-AAI antibody. The labeling reagent is also wicked through the support to contact the peptide-AAI complexes for binding of the labeling reagent to the complex, which indicates the presence or absence in the serum of antibody to the allergenic epitope contained in the peptide immobilized at each discrete location of the support.

In an alternative aspect, any of the foregoing embodiments and aspects of the methods of the invention may be in the form of a flow cytometry assay in which each allergenic epitope-containing peptide is conjugated to a separately identifiable solid support suitable for analysis by flow cytometry, such as a bead. Typically, the peptide is conjugated to the solid support by binding to a peptide-specific capture antibody on the solid support or by chemical linkage to the solid support. In this aspect, the bead with the conjugated allergenic epitope-containing peptide is contacted with the serum of a subject to bind any peptide-specific AAI that is present to the bead, forming a peptide-AAI complex on the bead. An AAI-specific labeling reagent comprising a fluorescent reporter moiety is then bound to the peptide-AAI complexes and the beads are analyzed quantitatively or qualitatively by flow cytometry. This detects fluorescence from the bound labeling reagent associated with each bead to which an allergenic epitope-containing peptide is conjugated, thereby identifying the peptide and the presence in the serum of AAI that is reactive to it. Presence of AAI reactive to at least one of a plurality of allergenic epitope-containing peptides selected from among SEQ ID NOs:1-33 indicates that the subject is allergic to cow's milk, and changes over time in the number of reactive peptides, or changes over time in the concentration of AAI reactive to one or more peptides, indicates an increase in intensity of the allergy, a decrease in the intensity of the allergy, or development of clinical tolerance over that time period.

In a further aspect, the flow cytometry assay may be a multiplex assay, such at the LUMINEX xMAP technology, which uses a microsphere array platform for quantitation and detection of peptides and proteins. Each of the plurality of allergenic epitope-containing peptides is bound to a set of beads with different spectral properties which can be used to identify the associated allergenic epitope-containing peptide by flow cytometry. The sets of beads are then contacted with serum of a subject to bind peptide-recognizing AAI to each bead to form a peptide-AAI complex on the bead, and an AAI-specific labeling reagent comprising a fluorescent reporter moiety is bound to the AAI of the complex. The beads are analyzed by monitoring the spectral properties of each bead and the amount of associated fluorescence from the bound labeling reagent. This process allows identification of the peptide on the bead, and the presence or absence of serum AAI that is reactive to it. Results of the assay are interpreted as discussed above.

In a further embodiment, the invention relates to a kit for detection of CMA, detection of an increase or decrease in CMA intensity, or detection of development of clinical tolerance to cow's milk proteins comprising, packaged together and including instructions for use:
 a) a plurality of allergenic epitope-containing peptides selected from among SEQ ID NOs:1-33;
 b) a labeling reagent comprising an anti-allergy associated immunoglobulin (AAI) antibody conjugated to a first reporter moiety; and
 c) optionally, a second reporter moiety that specifically binds to the labeling reagent.

The labeling reagent may be conjugated to a first reporter moiety that is directly detectable, such as a fluorescent dye, radiolabel, or colored dye. In specific examples, a phycoerythrin (PE) molecule can be directly coupled to an anti-allergy associated immunoglobulin and used for detection. Alternatively, the first reporter moiety may be a reporter moiety that is indirectly detectable (e.g., an enzyme label of chromogenic dye) and the kit may optionally include a specific binding partner for the first reporter moiety conjugated to a directly detectable label (the second reporter moiety). For example, the kit may include a biotin-conjugated anti-AAI antibody and a streptavidin-conjugated fluorescent dye for detection of the biotin-conjugated anti-AAI.

Figure 1:
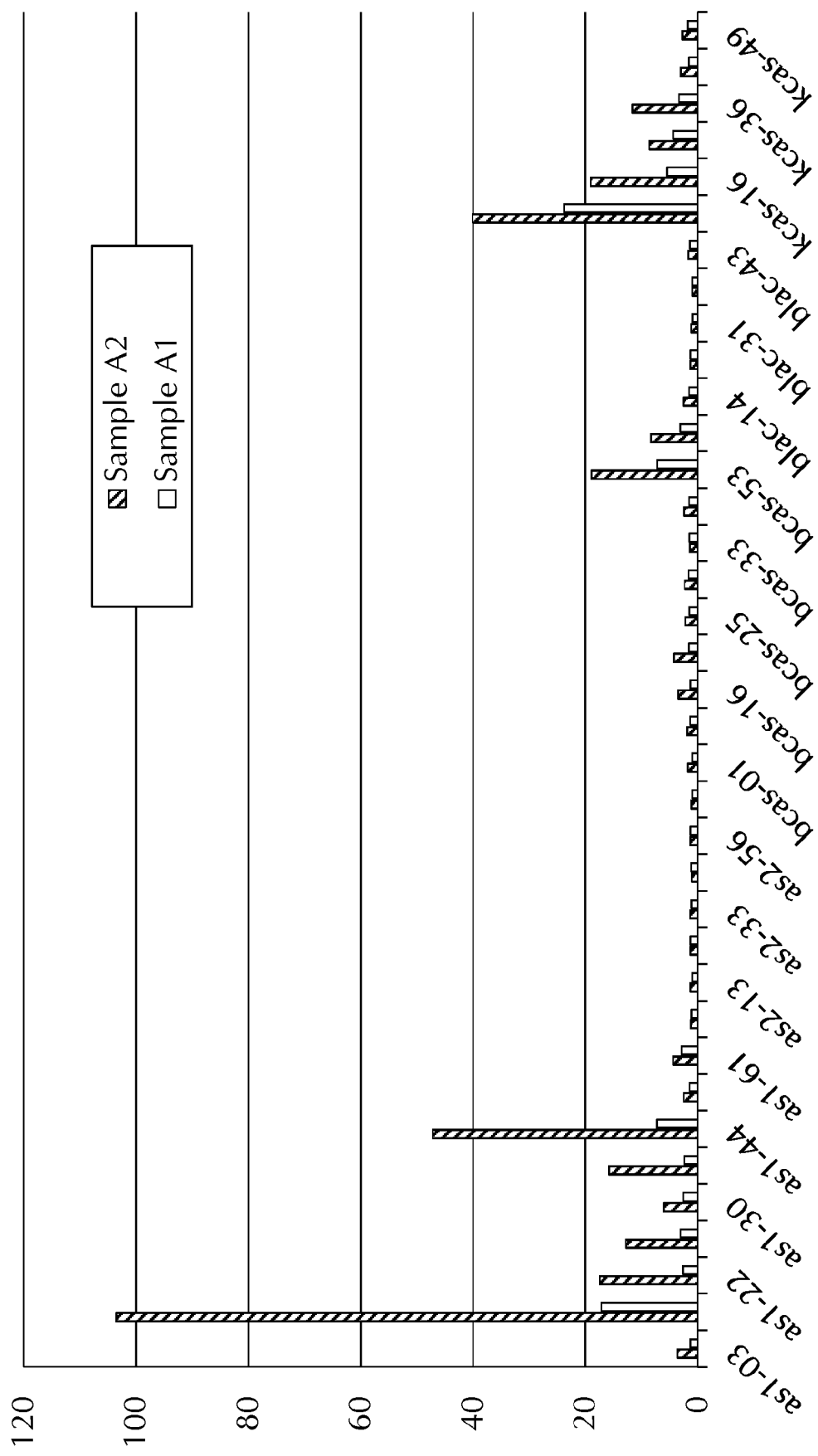
FIG. 1 illustrates serum reactivity over time to the peptide panel of SEQ ID NOs:1-33 of a cow's milk tolerant individual receiving immunotherapy for CMA.

In the drawings, peptides identified beginning with "a" represent "alpha", peptides identified beginning with "b" represent "beta" and peptides identified as beginning with "k" represent "kappa."

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

As used herein, the terms "allergy associated immunoglobulin" and "AAI" refer to immunoglobulins in sera that mediate hypersensitivity to food allergens. These include one or more of IgE, IgA, and IgG (including IgG4).

As used herein, the terms "reactive", "reactivity", "recognize" and the like refer to the ability of an allergy associated immunoglobulin to bind to an allergenic epitope containing peptide. The level of reactivity indicates the concentration of AAI in the serum, with high reactivity associated with higher AAI concentrations and lower reactivity associated with lower AAI concentrations. The relative AAI concentration (i.e., the relative serum reactivity) is determined by the amount of signal detected in the assay. The level of reactivity of AAI to allergenic epitope containing peptides also indicates the intensity of the allergic response, i.e., higher reactivity is associated with a more intense allergic reaction.

As used herein, the term "clinical tolerance" refers to immunological tolerance to a food allergen that is developed by an allergic subject as a result of exposure to the allergen, i.e., tolerance developed as a result of immunotherapy.

As used herein, the term "natural tolerance" refers to immunological tolerance to a food allergen that is developed by an allergic subject as a biochemical process over time, either as a result of natural exposure to the allergen during a lifetime or in the absence of exposure.

It is to be understood that although the allergenic epitope-containing peptides disclosed herein are described as specific embodiments having specific amino acid sequence, one skilled in the art will recognize that each such peptide may be shifted in either the N-terminal or C-terminal direction of the protein from which it is derived to obtain a related peptide sequence that still contains the relevant epitope but in which the relevant epitope is flanked by different amino acids than specified. Accordingly, in all embodiments and aspects the invention includes allergenic epitope containing peptides having amino acid sequences that overlap with the disclosed peptide sequences by 8 or more contiguous amino acids.

The allergenic epitope-containing peptides represented by SEQ ID NOs:1-33 were identified in a library of peptides derived from αS1-casein, αS2-casein, β-casein, β-lactoglobulin, and κ-casein as having a z-score in highly allergic individuals of greater than 10. In highly allergic subjects, all thirty-three peptides of SEQ ID NOs:1-33 are reactive with sera. Conversely, in non-allergic subjects none of the thirty-three peptides of SEQ ID NOs:1-33 are reactive with sera. The individual peptides of SEQ ID NOs:1-33 also provide a continuum of reactivity which is useful for determining the intensity of CMA in an individual, and for monitoring changes in the intensity of CMA over time. Individuals having intensities of allergy to cow's milk that fall between non-reactive and the most highly reactive have sera that are reactive with some, but not all, of the peptides among SEQ ID NOs:1-33. In general, the number of peptides among SEQ ID NOs:1-33 that are reactive with the sera of these individuals is positively correlated with the intensity of the allergy, i.e., the more intense the allergy the more peptides among SEQ ID NOs:1-33 are reactive with the sera. The sera of individuals with mild allergy are reactive with fewer peptides than the sera of individuals with more intense allergy. The invention therefore not only provides methods for diagnosing CMA, it provides methods for determining the intensity of the allergy and methods for determining changes in the intensity of the allergy over time, including detection of development of clinical tolerance to cow's milk proteins.

In certain aspects of the invention, the number of allergenic epitope-containing peptides within the group of SEQ ID NOs:1-33 that are reactive with the sera of a CMA subject has a positive correlation with the intensity of the allergic response, i.e., reactivity with fewer peptides indicates a milder allergic response to cow's milk and reactivity with more peptides indicates the subject is more highly allergic to cow's milk. In another aspect of the invention, the intensity of binding of serum IgE to the peptides represented by SEQ ID NOs:1-33 (a measure of IgE concentration in the sera) correlates with the intensity of the allergic response, i.e., weaker reactivity with all thirty-three peptides, or with a subset of the thirty-three peptides, indicates a more moderate allergic response compared to stronger reactivity with all thirty-three peptides or with the subset of peptides. As used herein, reference to "non-reactive" or "negative" reactivity with an allergenic epitope-containing peptide means a signal-to-noise ratio (S/N) in the assay that is less than about 2. A typical background signal (N) is that generated by a pool of sera from non-allergenic individuals. Alternatively, the invention contemplates use of negative peptides as the basis for establishing the background signal. As used herein, reference to "weak" or "moderate" "moderate" reactivity with an allergenic epitope-containing peptide means a S/N of about 2-10, although this value may vary depending on the peptide and the allergy. As used herein, reference to "high" or "strong" reactivity with an allergenic epitope-containing peptide means a S/N of greater than about 10.

Previously known assays for CMA based on analysis of peptide epitopes in cow's milk proteins are competitive immunoassays which rely on analysis of the relative affinity of binding of IgE and IgG4 to the epitope. The affinity of antibody binding is believed to be related to whether or not the subject will develop clinical tolerance to cow's milk. In contrast, in one aspect, the present invention is based on an analysis of the presence or absence of AAI binding to each individual peptide in a set of key cow's milk protein epitopes that correlates with a diagnosis of CMA, with the intensity of the allergic response, and with the potential of a patient to either develop tolerance or experience an increased allergic response based on the number of epitopes (i.e., peptides) bound by IgE in the serum of the subject. In a second aspect, the invention is based on analysis of the concentration of AAIs in sera that are reactive with each of the allergenic epitope-containing peptides, which also correlates with the intensity of the allergic response.

One embodiment of the invention relates to a method for diagnosing CMA in a subject comprising providing a plurality of peptides selected from among SEQ ID NOs:1-33, each peptide conjugated to a separately identifiable solid support, contacting each solid support with serum obtained from the subject under conditions sufficient to permit binding of AAI in the serum to the peptide on each solid support to form a peptide-AAI complex, binding an AAI-specific labeling reagent to the peptide-AAI complex, and analyzing binding of the labeling reagent to each peptide-AAI complex to identify peptides recognized by the AAI in the serum of the subject. If, following exposure to cow's milk allergens, at least one peptide is moderately or highly reactive with serum AAI (S/N>2) and reactivity of one or more of the reactive peptides does not decrease at least 2-fold within about six months, the subject is diagnosed as having CMA.

Serum reactivity of a cow's milk tolerant individual following administration of CMA immunotherapy is shown in FIG. 1. In this experiment, a cow's milk tolerant individual was treated with immunotherapy for CMA and serum samples were taken 6-12 months apart. It can be seen that the initial response to immunotherapy resulted in moderate to high reactivity with about eleven of the peptides (blue bars, S/N>2). Within six months (orange bars), there was at least about a 2-fold reduction in reactivity for all of these peptides. Although kcas-04 was in the range of slightly less than a 2-fold reduction in reactivity, the most highly reactive peptides (e.g., as1-09, as1-44) exhibited reductions in reactivity within six months that were substantially larger than 2-fold, in the range of at least 5-fold. In addition, none of the reactive peptides (S/N>2) failed to diminish in reactivity at the six month time-point.

In another aspect of the method, the analysis of binding of the labeling reagent to each peptide-AAI complex may include analysis of the extent of binding, which indicates a concentration of each peptide-specific AAI in the serum. A low to moderate serum reactivity with all of the peptides of SEQ ID NOs:1-33, or with a subset thereof, indicates a lower concentration of peptide-specific AAI in the serum and mild to moderate CMA, whereas high serum reactivity with all of the peptides, or a subset thereof, indicates a higher concentration of peptide-specific AAI in the serum and more severe CMA. The analysis of binding for diagnosis of CMA may employ either the number of peptides reactive with sera, the extent of binding of serum AAI to the peptides, or both.

In certain aspects, the invention further relates to peptides of cow's milk proteins that contain epitopes that are non-reactive with the sera of subjects that are allergic to cow's milk, even if the subject is phenotypically highly allergic. The sera of non-allergic subjects are also non-reactive with these peptides. These peptides are represented by SEQ ID NOs:34, 35 and 36, and are useful as negative controls in specific embodiments of the assays for diagnosis of CMA. Having a highly reliable negative control available for this purpose reduces the likelihood of false positive diagnoses and falsely high determinations of reactive AAI concentration.

In specific embodiments, of the methods for diagnosing CMA in a subject using a plurality (two or more) of peptides selected from among SEQ ID NOs:1-33 include solid phase assays. The plurality of peptides selected for use in the solid phase assay may represent all 33 peptides of SEQ ID NOs:1-33, a subset of 5-10 peptides, a subset of 10-15 peptides, or a subset of 15-20 peptides. The methods may also employ two or more such subsets of the peptides. Each of the plurality of peptides selected from among SEQ ID NOs:1-33 is provided conjugated to a solid support, which may be a bead, a microtiter plate, a chromatographic material (e.g., a filter), or any other suitable solid support. Each bead, microtiter plate well, or discrete location on the chromatographic material is occupied by a single peptide selected from among SEQ ID NOs:1-33. The solid supports are then contacted with serum obtained from the subject under conditions appropriate for specific binding of anti-peptide AAIE in the serum (if present) to the peptide on each solid support or discrete location on a solid support to form a peptide-AAI complex on the solid support.

Any peptide-AAI complex formed on a solid support is then detected by contacting the complex on each solid support or discrete location on the solid support with a labeling reagent that specifically binds to the complex, typically by binding to the immobilized serum AAI antibody. A single labeling reagent will generally be used for universal detection of all complexes. The specific peptide-AAI complex may then be identified by its position on the microtiter plate or chromatographic support. When the solid support to which each peptide is conjugated has different spectral properties, the specific peptide-AAI complex may also be identified by analysis of the spectral properties of the solid support associated with the peptide-AAI complex, once the presence of a complex is identified via a detectable signal from the labeling reagent bound to the complex. As an example, the presence or absence of a peptide-AAI complex in each well of a microtiter plate can be determined by binding to the complex an anti-human AAI antibody that is conjugated to a reporter moiety, such as a fluorescent dye, a chromogenic dye, an enzyme label or a radioactive label. Alternatively, the anti-human AAI antibody may be conjugated to a reporter moiety that is not directly detectable, so specific binding of a second, directly detectable reporter moiety to the labeling reagent is necessary for analysis of binding.

In certain aspects, the methods for diagnosis of CMA are qualitative methods, i.e., based only on presence or absence of AAI reactive to each selected peptide. Presence of AAI moderately or highly reactive with any selected peptide can be considered to indicate some degree of CMA, provided that the reactivity does not substantially diminish within a short period of time such as about six months. The methods may also be semi-quantitative, i.e., the greater the number of peptides reactive with the serum of the subject the relatively more intense the allergy and, conversely, the fewer the number of reactive peptides the relatively less intense the allergy. Serum reactivity with 5-15 of the peptides of SEQ ID NOs:1-33 may indicate mild to moderate CMA, with reactivity within the lower end of this range generally characterized as mild CMA. Serum reactivity with 16-33, 16-30, 16-25, 16-20, 16-18 or all 33 peptides of SEQ ID NOs:1-33 may indicate moderate to severe CMA, with reactivity within the lower end of this range generally characterized as moderate CMA. In the midrange, serum reactivity with 10-20, 12-18 or 14-16 of the peptides of SEQ ID NOs:1-33 may generally be considered to indicate moderate CMA. It is a particularly useful feature of the peptides of SEQ ID NOs:1-33 that generally no more than about 8-10 are highly reactive (S/N>10) with the sera of non-allergic individuals and thus provide a higher confidence level in the result of the diagnostic assay than conventional assays.

In other aspects, the methods for diagnosis of CMA are quantitative methods, i.e., based on quantitation of the level of AAI reactivity to each selected peptide. In this example, the level of reactivity correlates with the amount of labeling reagent bound to the peptide-AAI complex, with higher levels of signal from the reporter moiety indicating a higher concentration of a particular peptide-specific AAI in the serum. To obtain the amount or concentration of reporter moiety bound to a particular peptide-AAI complex, the quantity of fluorescence from a fluorescent dye, intensity of color from a colored or chromogenic dye or from an enzyme label, or quantity of radioactivity from a radioactive label is positively correlated with the amount of bound AAI in the complex and therefore its concentration. Methods for measuring these parameters are known in the art. The relative quantities of AAI reactive with any of the peptides can be considered to indicate the degree or intensity of CMA. That is, the higher the level of reactivity of the plurality of selected peptides, or of one or more peptides within the selected peptides, the more intense the allergy. Conversely, the lower the level of reactivity of the plurality of selected peptides, or of one or more peptides within the selected peptides, the less intense the allergy.

A particularly useful quantitative assay for use in any of the methods of the invention is a multiplex peptide-bead assay for flow cytometric analysis, such as the LUMINEX exMAP multiplex bead assay, which is a high-throughput alternative to the ELISA. In this assay, polystyrene beads (microspheres) dyed with distinct proportions of red and near-infrared fluorophores are used as the solid support. The peptides may be chemically linked to the beads or bound thereto through peptide-specific capture antibodies coated on the beads. The proportions of the fluorophores define a "spectral address" for each bead population that can be identified by a flow cytometer using digital signal processing. Detection of a third fluorescence color is used for measurement of the fluorescence intensity of the reporter moiety of the labeling reagent bound to the bead. Multiple analytes can be detected simultaneously by binding each peptide selected from among SEQ ID NOs:1-33 to a bead having a specific "spectral address." Contacting the beads with serum containing AAI that are specific for the peptide bound to it is followed by addition of anti-human AAI antibodies conjugated to a reporter moiety. In one example, the reporter moiety of the anti-human AAI is biotin and binding to phycoerythyrin (PE)-conjugated streptavidin provides the fluorescent signal for detection. Following binding of the labeling reagent, the beads are analyzed on a dual-laser flow-based detection instrument, such as the LUMINEX 200 or Bio-Rad BIO-PLEX analyzer. One laser classifies the bead and identifies the peptide bound to it. The second laser determines the magnitude of the reporter-derived signal, which is in direct proportion to the amount of bound serum AAI.

Because the degree of binding of each peptide-specific AAI to the peptide-AAI complex on the solid support can be quantitated, the plurality of peptides selected from among peptides represented by SEQ ID NOs:1-33 are also useful in methods for detecting an increase in the intensity of CMA over time in a subject diagnosed with CMA or development of CMA over time in a subject initially diagnosed as non-allergic. An initial assay is performed on a plurality of peptides selected from among SEQ ID NOs:1-33 as described above to provide an initial number of reactive peptides or an initial concentration of each peptide-specific AAI. At a time-point subsequent to the initial assay, the analysis is repeated with the same plurality of peptides selected from among SEQ ID NOs:1-33 as the initial profile to obtain a subsequent number of reactive peptides or a subsequent concentration of peptide-specific AAI. This method can be summarized as follows: providing an initial profile of a subject's serum AAI reactivity to a plurality of peptides selected from among SEQ ID NOs:1-33, wherein the initial profile indicates an initial number of peptides recognized (bound) by AAI in the serum of the subject or an initial concentration of AAI in the serum of the subject that recognizes (binds to) each peptide; at a time-point subsequent to the initial profile, contacting each peptide of the same plurality of peptides conjugated to a separately identifiable solid support with serum from the subject under conditions sufficient to permit binding of AAI in the serum to the peptide on each solid support, forming a peptide-AAI complex; binding an AAI-specific labeling reagent to the complex, and; analyzing the binding of the labeling reagent to each peptide-AAI complex to identify a subsequent number of peptides recognized by AAI in the serum of the subject or a subsequent concentration of AAI in the serum of the subject that reacts with each selected peptide.

An alternative assay format useful in the invention is a lateral flow or immunochromatographic assay. In such an assay, the selected allergenic epitope containing peptide(s) are immobilized on the porous support and serum containing the AAI is wicked into contact with the peptide(s) to form immunocomplexes. Further migration of the immunocomplex through the porous support brings it into contact with a specific capture reagent for detection of the immunocomplex using appropriate detection reagents.

The methods for detecting an increase in intensity of the allergy may make use of any appropriate assay format, including those described above. Examples of the types of analyses available for analyzing binding of the labeling reagent are also as described above. An increase in the number of peptides reactive with AAI at the subsequent time-point compared to the initial profile (including an increase compared to no peptides reactive with AAI in the initial profile), or an increase in intensity of binding of AAI to any of the peptides at the subsequent time-point compared to the initial profile (including an increase from no binding to a particular peptide in the initial profile to detectable binding at the subsequent time-point), indicates an increase in the intensity of CMA in a subject previously diagnosed with CMA or development of CMA in the previously non-allergic subject. As discussed above, comparing the initial profile of a subject to that of a subsequent time point may be used to predict the subject's increase in severity or lower tolerance in a particular allergy, or to predict the likelihood of development of clinical or natural tolerance to the allergen.

The plurality of peptides selected from among peptides represented by SEQ ID NOs:1-33 are also useful in methods for detecting development of clinical tolerance to cow's milk proteins in a subject diagnosed with CMA. In these embodiments, the assay generally as described above for detection of an increase in allergy intensity, is performed first at an initial time-point to establish an initial profile of serum AAI reactivity with the plurality of peptides selected from among SEQ ID NOs:1-33. The initial profile is based on semi-quantitative or quantitative analysis of serum reactivity with the selected peptides, as discussed above. The selected peptides conjugated to the solid supports are then contacted with serum from the subject obtained at a time-point subsequent to the initial profile and the assay is conducted as above with semi-quantitation or quantitation of the intensity of CMA at the subsequent time-point. A reduction in the number of peptides reactive with AAI at the subsequent time-point as compared to the initial profile, or a reduction in intensity of binding of AAI to any of the peptides at the subsequent time-point as compared to the initial profile, particularly at least a 2-fold reduction, indicates development of clinical tolerance to cow's milk proteins. It will be appreciated that development of clinical tolerance to cow's milk proteins in a subject previously diagnosed with CMA also indicates a decrease in allergy intensity over the time period between the initial profile and the subsequent time-point, and that the method can also be used to detect and predict such decreases in allergy intensity over time.

Figure 2:
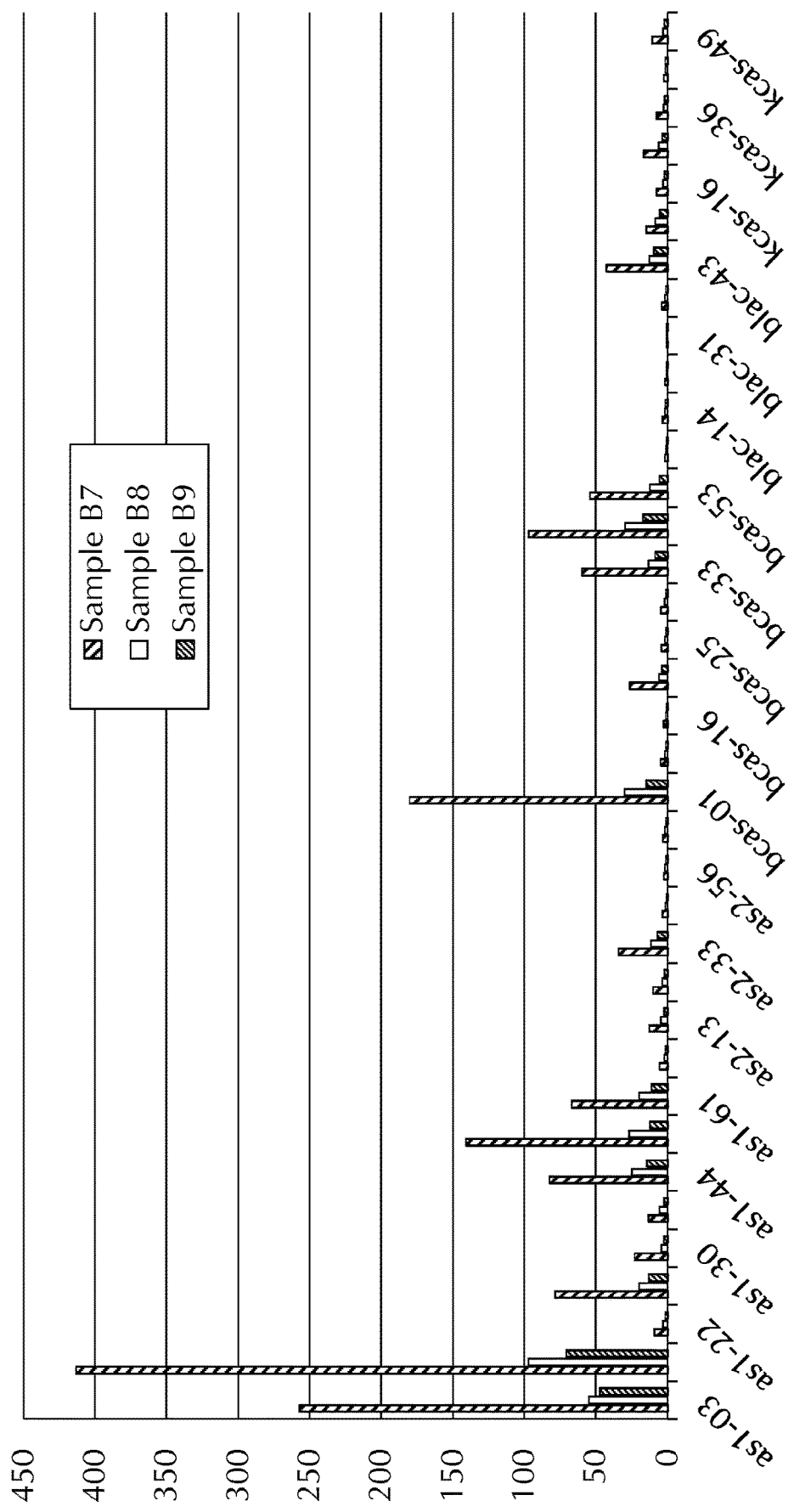
FIG. 2 illustrates serum reactivity over time to the peptide panel of SEQ ID NOs:1-33 of an individual with CMA who became desensitized in response to immunotherapy for CMA.

As an example, serum reactivity of a CMA allergic individual is shown in FIG. 2. In this experiment, an individual allergic to cow's milk was treated with immunotherapy for CMA and serum samples were taken 6 months and 12 months later. It can be seen that the initial response to immunotherapy involved moderate to high reactivity with about 15-17 peptides (i.e., S/N>2, blue bars). At six months, serum reactivity had diminished greater than 2-fold for all of the most reactive peptides (orange bars). Reduction in reactivity for certain peptides was in the range of 4-fold to 7-fold (e.g., as1-03, as1-09, as1-57, as1-44, bcas-01). Little or no further reduction in reactivity was observed at 12 months (gray bars), and none of the initially most reactive peptides returned to non-reactive levels (S/N<2). This individual became desensitized to cow's milk over the course of immunotherapy, showing that the assay successfully detected development of clinical tolerance to cow's milk proteins in a subject diagnosed with CMA Several peptides in the panel were highly reactive with the sera of the individual shown in FIG. 2 (S/N>10). Similarly, sera of the individual tested in FIG. 3 were moderately to highly reactive with at least about 15 peptides, indicating allergy to cow's milk. In contrast, however, at six months (orange bars) fewer than all of the initially most reactive peptides exhibited a reduction in reactivity of at least 2-fold. Examples of minimal reduction in reactivity<2-fold are seen, for example, with as1-61, bcas-25, and bcas-53. The individual shown in FIG. 3 only partially responded to immunotherapy and, although there were greater than 2-fold reductions in reactivity with some of the most highly reactive peptides, the finding that some of the highly reactive peptides did not exhibit a similar reduction in reactivity may be an indication that immunotherapy is less likely to result in complete desensitization or that complete desensitization may require a longer treatment with immunotherapy.

It will also be recognized that analysis of all thirty-three of the peptides represented by SEQ ID NOs:1-33 is not always necessary to obtain useful results in the foregoing methods of the invention. It is only necessary to employ a sufficient number of peptides selected from among the peptides represented by SEQ ID NOs:1-33 to provide a statistically reliable result. For example, if the CMA status of a subject is not known, it is generally desirable to analyze a greater number of allergenic epitope-containing peptides selected from among the peptides represented by SEQ ID NOs:1-33 to ensure that mild to moderate CMA, that may involve reactivity with only a few of the peptides represented by SEQ ID NOs:1-33, is detectable. Conversely, if a subject is known to have high-intensity CMA, fewer allergenic epitope-containing peptides selected from among the peptides represented by SEQ ID NOs:1-33 may be sufficient to detect changes in allergy intensity or development of clinical tolerance, because a larger number of the peptides represented by SEQ ID NOs:1-33 will be initially reactive. However, because changes in allergy intensity and development of clinical tolerance are evidenced by changes in the number of peptides reactive with sera as well as changes in concentration of serum IgE reactive with a particular peptide, it is particularly desirable to include in the assays a large enough set of peptides selected from among the peptides represented by SEQ ID NOs:1-33 to ensure that changes with respect to a peptide that is diagnostic for a particular subject are not missed. Accordingly, the plurality of allergenic epitope-containing peptides selected from among peptides represented by SEQ ID NOs:1-33 for use in any of the foregoing methods may represent all 33 peptides of SEQ ID NOs:1-33, a subset of 20-25 peptides, a subset of 15-20 peptides, a subset of 10-15 peptides, a subset of 5-10 peptides or a subset of 2-5 peptides. By way of example, it has been found that in many cases the betalac peptides (SEQ ID NOs:24-27) are substantially less reactive, or non-reactive, with sera of allergic individuals. Accordingly, it may be desirable to use the SEQ ID NOs:1-23 (the alphaS1, alphaS2, and betacas peptides) alone or with SEQ ID NOs:28-33 (the kappacas peptides) for certain applications. Each of these subgroups may also be used alone in the invention if desired.

For the convenience of the user, the reagents for use in any of the foregoing methods may be packaged together in the form of a kit comprising a plurality of allergenic epitope-containing peptides selected from among the peptides represented by SEQ ID NOs:1-33 or any of the useful subgroups, a labeling reagent comprising an anti-human IgE antibody conjugated to a first reporter moiety and, optionally (if required for indirect detection) a second reporter moiety that specifically binds to the labeling reagent. The kit will typically include instructions for use of these reagents in one or more of the methods of the invention described above.

In certain kit embodiments, as well as in the methods of the invention, the anti-human AAI antibody may be provided conjugated to a reporter moiety that can be directly detected. Directly detectable reporter moieties are those that can be identified and/or quantitated without the need for binding to a specific binding partner. Examples of directly-detectable reporter moieties that may be conjugated to the anti-human AAI antibody include fluorescent dyes, colored dyes, chromogenic dyes and enzyme labels that can be detected by a subsequent chemical reaction, and radiolabels. In other kit embodiments, as in the methods of the invention, the anti-human AAI antibody may be provided conjugated to a reporter moiety that is indirectly detectable, i.e., a reporter moiety that is not itself detectable but which undergoes a reaction or interaction with a second reporter moiety that comprises a directly detectable reporter moiety, such as a specific binding partner for the reporter moiety conjugated to a directly detectable label. Examples of indirectly-detectable reporter moieties include biotin, digoxigenin, and other haptens that are detectable upon subsequent binding of a secondary antibody (e.g., anti-digoxigenin) or other binding partner (e.g., streptavidin) which is labeled for direct detection. It will be understood that any of these labeling reagents and reporter moieties are useful in the appropriate assay format in the foregoing methods of the invention and as components of the kits. In a specific example of a kit for performing the flow cytometry multiplex assay described above, the components of the kit may comprise a plurality of allergenic epitope-containing peptides selected from among the peptides represented by SEQ ID NOs:1-33, a biotinylated anti-human AAI antibody (labeling reagent with first reporter moiety), and streptavidin conjugated to PE (second reporter moiety).

The plurality of allergenic epitope-containing peptides selected from among SEQ ID NOs:1-33 for inclusion in any of the foregoing kits may represent all 33 peptides of SEQ ID NOs:1-33, a subset of 20-25 peptides, a subset of 15-20 peptides, a subset of 10-15 peptides, a subset of 5-10 peptides or a subset of 2-5 peptides. The plurality of allergenic epitope-containing peptides selected from among SEQ ID NOs:1-33 for inclusion in any of the foregoing kits may also represent one or more of the related peptides subgroups (i.e., alphaS1, alphaS2, betacas, betalac and kappacas peptides)

In a further aspect, the invention provides additional allergenic epitope containing peptides derived from cow's milk proteins for use in the foregoing methods, peptide panels and kits. These peptides, and subsets thereof, can be substituted for any or all of SEQ ID NOs:1-33 in any aspect and/or embodiment discussed above. In addition, the peptides and subsets thereof, can be used in addition to SEQ ID NOs:1-33 in any aspect and/or embodiment discussed above. The additional allergenic epitope containing peptides derived from cow's milk proteins include:

| | | |
|---|---|---|
| alphas1-07 | NLLRFFVAPFPEVFGKEKVN | SEQ ID NO: 37 |
| alphas1-25 | PNSVEQKHIQKEDVPSERYL | SEQ ID NO: 38 |
| alphas1-28 | QKEDVPSERYLGYLEQLLRL | SEQ ID NO: 39 |
| alphas1-37 | LEIVPNSAEERLHSMKEGIH | SEQ ID NO: 40 |
| alphas1-40 | ERLHSMKEGIHAQQKEPMIG | SEQ ID NO: 41 |
| alphas1-43 | IHAQQKEPMIGVNQELAYFY | SEQ ID NO: 42 |
| alphas1-46 | IGVNQELAYFYPELFRQFYQ | SEQ ID NO: 43 |
| alphas1-54 | PSGAWYYVPLGTQYTDAPSF | SEQ ID NO: 44 |
| alphas1-55 | AWYYVPLGTQYTDAPSFSDI | SEQ ID NO: 45 |
| alphas2-05 | SIISQETYKQEKNMAINPSK | SEQ ID NO: 46 |
| alphas2-10 | INPSKENLCSTFCKEVVRNA | SEQ ID NO: 47 |
| alphas2-21 | SAEVATEEVKITVDDKHYQK | SEQ ID NO: 48 |
| alphas2-44 | TSEENSKKTVDMESTEVFTK | SEQ ID NO: 49 |
| alphas2-51 | TKLTEEEKNRLNFLKKISQR | SEQ ID NO: 50 |
| alphas2-62 | YQHQKAMKPWIQPKTKVIPY | SEQ ID NO: 51 |
| betacas-21 | PFPGPIPNSLPQNIPPLTQT | SEQ ID NO: 52 |
| betacas-27 | QTPVVVPPFLQPEVMGVSKV | SEQ ID NO: 53 |
| betacas-44 | VENLHLPLPLLQSWMHQPHQ | SEQ ID NO: 54 |
| betacas-48 | SWMHQPHQPLPPTVMFPPQS | SEQ ID NO: 55 |
| betacas-56 | SQSKVLPVPQKAVPYPQRDM | SEQ ID NO: 56 |
| betalac-18 | GDLEILLQKWENDECAQKKI | SEQ ID NO: 57 |
| betalac-44 | DEALEKFDKALKALPMHIRL | SEQ ID NO: 58 |
| kappacas-06 | RFFSDKIAKYIPIQYVLSRY | SEQ ID NO: 59 |
| kappacas-16 | KPVALINNQFLPYPYYAKPA | SEQ ID NO: 60 |
| kappacas-21 | YAKPAAVRSPAQILQWQVLS | SEQ ID NO: 61 |
| kappacas-24 | PAQILQWQVLSNTVPAKSCQ | SEQ ID NO: 62 |
| kappacas-30 | CQAQPTTMARHPHPHLSFMA | SEQ ID NO: 63 |
| kappacas-33 | RHPHPHLSFMAIPPKKNQDK | SEQ ID NO: 64 |
| kappacas-41 | TINTIASGEPTSTPTTEAVE | SEQ ID NO: 65 |
| kappacas-50 | DSPEVIESPPEINTVQVTST | SEQ ID NO: 66 |
| kappacas-51 | PEVIESPPEINTVQVTSTAV | SEQ ID NO: 67 |
| betalac-39 | QSLVCQCLVRTPEVDDEALE | SEQ ID NO: 68 |

EXAMPLES

Figure 3:
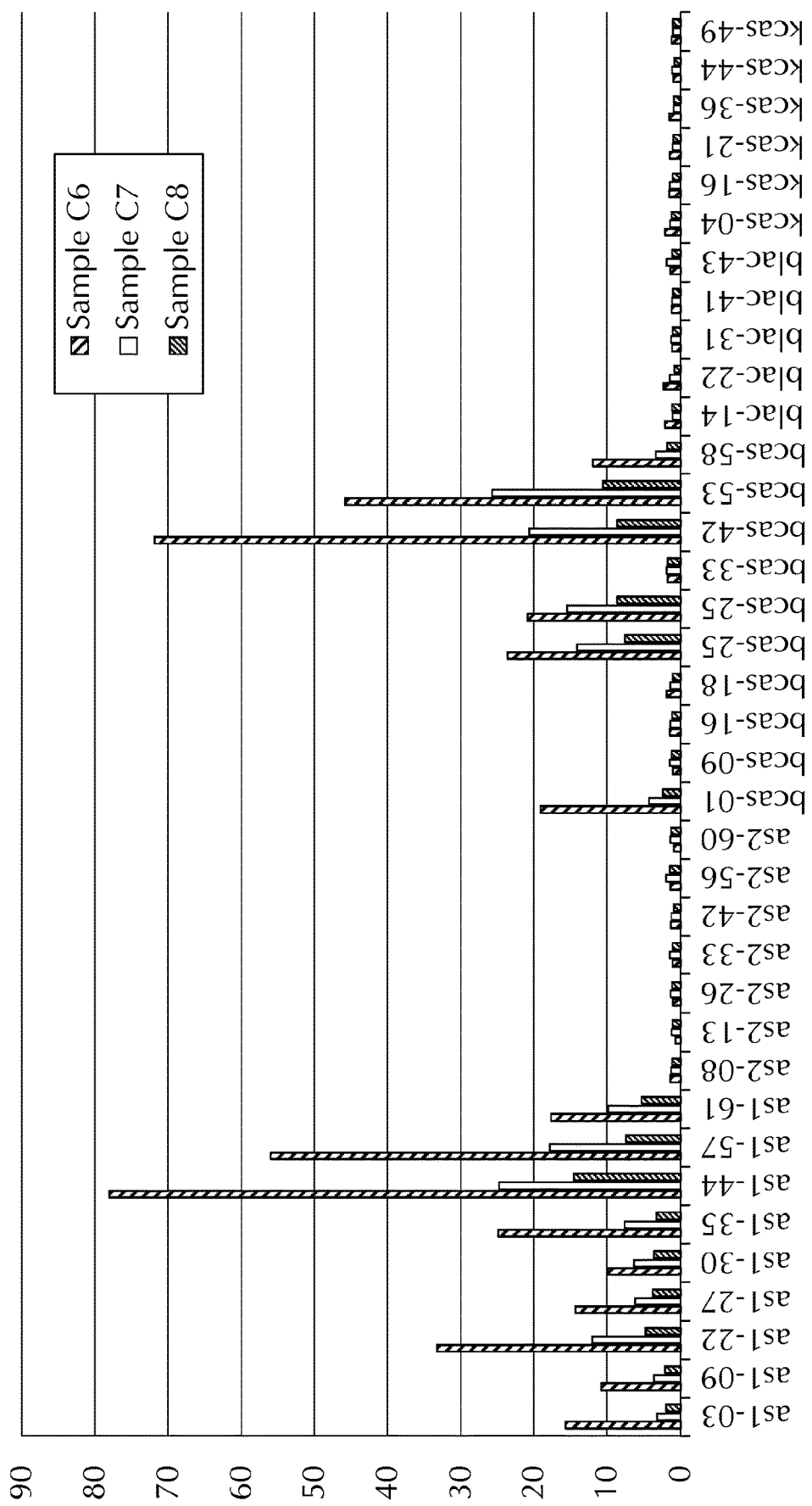
FIG. 3 illustrates serum reactivity over time to the peptide panel of SEQ ID NOs:1-33 of an individual with CMA who partially responded to immunotherapy for CMA.

Sera were obtained from CM tolerant and CMA individuals and assayed in the LUMINEX assay to obtain the representative results shown in FIGS. 1-3. Wash buffer, sera, beads and antibody dilutions were prepared according to the manufacturer's directions. The filter plate was pre-wet with buffer for 1 min. and the buffer was removed by vacuum. 100 µl of the bead cocktail was added to each well, the buffer was removed by vacuum, and the beads were washed twice with 100 μl buffer. 100 μl of sera dilution was added to each well and incubated for 2 hrs. with shaking. Vacuum was applied to remove liquid. Beads were again washed twice with buffer. 50 μl of the antibody dilution was applied to each well and incubated for 30 min. with shaking. After application of vacuum the well was washed three times. 100 μl of buffer was added to the wells and the samples were transferred to a fixed plate. The wells were read on the LUMINEX instrument. Results are shown in FIGS. 1-3 and discussed above.

Additional Applications of the Methods

The concepts of the invention with respect to allergenic epitope-containing peptides derived from cow's milk and their use for diagnosis of CMA, for detecting development of clinical tolerance to cow's milk proteins, and for detecting increases and decreases in the intensity of the allergy can also be applied to development of other allergenic epitope-containing peptide panels and their use in diagnosing, detecting tolerance, and detecting increases and development of tolerance to other allergenic proteins.

For example, allergenic epitope-containing peptide panels derived from allergenic peanut proteins, particularly the Ara h protein family, may be utilized in methods similar to those discussed above. Such a panel may include one or more peptides from the following list (SEQ ID NOs:69-277):

| | | | |
|---|---|---|---|
| ara h 1.006 | VLASVSATHAKSSPY | SEQ ID NO: | 69 |
| ara h 1.007 | SVSATHAKSSPYQKK | SEQ ID NO: | 70 |
| ara h 1.008 | ATHAKSSPYQKKTEN | SEQ ID NO: | 71 |
| ara h 1.012 | TENPCAQRCLQSCQQ | SEQ ID NO: | 72 |
| ara h 1.013 | PCAQRCLQSCQQEPD | SEQ ID NO: | 73 |
| ara h 1.015 | LQSCQQEPDDLKQKA | SEQ ID NO: | 74 |
| ara h 1.016 | CQQEPDDLKQKACES | SEQ ID NO: | 75 |
| ara h 1.017 | EPDDLKQKACESRCT | SEQ ID NO: | 76 |
| ara h 1.019 | QKACESRCTKLEYDP | SEQ ID NO: | 77 |
| ara h 1.020 | CESRCTKLEYDPRCV | SEQ ID NO: | 78 |
| ara h 1.021 | RCTKLEYDPRCVYDP | SEQ ID NO: | 79 |
| ara h 1.022 | KLEYDPRCVYDPRGH | SEQ ID NO: | 80 |
| ara h 1.023 | YDPRCVYDPRGHTGT | SEQ ID NO: | 81 |
| ara h 1.025 | YDPRGHTGTTNQRSP | SEQ ID NO: | 82 |
| ara h 1.026 | RGHTGTTNQRSPPGE | SEQ ID NO: | 83 |
| ara h 1.028 | TNQRSPPGERTRGRQ | SEQ ID NO: | 84 |
| ara h 1.029 | RSPPGERTRGRQPGD | SEQ ID NO: | 85 |
| ara h 1.030 | PGERTRGRQPGDYDD | SEQ ID NO: | 86 |
| ara h 1.031 | RTRGRQPGDYDDDRR | SEQ ID NO: | 87 |
| ara h 1.032 | GRQPGDYDDDRRQPR | SEQ ID NO: | 88 |
| ara h 1.033 | PGDYDDDRRQPRREE | SEQ ID NO: | 89 |
| ara h 1.034 | YDDDRRQPRREEGGR | SEQ ID NO: | 90 |
| ara h 1.035 | DRRQPRREEGGRWGP | SEQ ID NO: | 91 |
| ara h 1.036 | QPRREEGGRWGPAGP | SEQ ID NO: | 92 |
| ara h 1.037 | REEGGRWGPAGPRER | SEQ ID NO: | 93 |
| ara h 1.038 | GGRWGPAGPRERERE | SEQ ID NO: | 94 |
| ara h 1.039 | WGPAGPREREREEDW | SEQ ID NO: | 95 |
| ara h 1.040 | AGPREREREEDWRQP | SEQ ID NO: | 96 |
| ara h 1.041 | REREREEDWRQPRED | SEQ ID NO: | 97 |
| ara h 1.042 | EREEDWRQPREDWRR | SEQ ID NO: | 98 |
| ara h 1.043 | EDWRQPREDWRRPSH | SEQ ID NO: | 99 |
| ara h 1.044 | RQPREDWRRPSHQQP | SEQ ID NO: | 100 |
| ara h 1.045 | REDWRRPSHQQPRKI | SEQ ID NO: | 101 |
| ara h 1.046 | WRRPSHQQPRKIRPE | SEQ ID NO: | 102 |
| ara h 1.047 | PSHQQPRKIRPEGRE | SEQ ID NO: | 103 |
| ara h 1.048 | QQPRKIRPEGREGEQ | SEQ ID NO: | 104 |
| ara h 1.049 | RKIRPEGREGEQEWG | SEQ ID NO: | 105 |
| ara h 1.050 | RPEGREGEQEWGTPG | SEQ ID NO: | 106 |
| ara h 1.051 | GREGEQEWGTPGSHV | SEQ ID NO: | 107 |
| ara h 1.052 | GEQEWGTPGSHVREE | SEQ ID NO: | 108 |
| ara h 1.053 | EWGTPGSHVREETSR | SEQ ID NO: | 109 |
| ara h 1.056 | REETSRNNPFYFPSR | SEQ ID NO: | 110 |
| ara h 1.057 | TSRNNPFYFPSRRFS | SEQ ID NO: | 111 |
| ara h 1.058 | NNPFYFPSRRFSTRY | SEQ ID NO: | 112 |
| ara h 1.089 | RIPSGFISYILNRHD | SEQ ID NO: | 113 |
| ara h 1.090 | SGFISYILNRHDNQN | SEQ ID NO: | 114 |
| ara h 1.094 | NQNLRVAKISMPVNT | SEQ ID NO: | 115 |
| ara h 1.095 | LRVAKISMPVNTPGQ | SEQ ID NO: | 116 |
| ara h 1.096 | AKISMPVNTPGQFED | SEQ ID NO: | 117 |
| ara h 1.097 | SMPVNTPGQFEDFFP | SEQ ID NO: | 118 |
| ara h 1.098 | VNTPGQFEDFFPASS | SEQ ID NO: | 119 |
| ara h 1.099 | PGQFEDFFPASSRDQ | SEQ ID NO: | 120 |
| ara h 1.100 | FEDFFPASSRDQSSY | SEQ ID NO: | 121 |
| ara h 1.102 | ASSRDQSSYLQGFSR | SEQ ID NO: | 122 |
| ara h 1.103 | RDQSSYLQGFSRNTL | SEQ ID NO: | 123 |
| ara h 1.104 | SSYLQGFSRNTLEAA | SEQ ID NO: | 124 |
| ara h 1.105 | LQGFSRNTLEAAFNA | SEQ ID NO: | 125 |
| ara h 1.112 | RVLLEENAGGEQEER | SEQ ID NO: | 126 |
| ara h 1.113 | LEENAGGEQEERGQR | SEQ ID NO: | 127 |
| ara h 1.114 | NAGGEQEERGQRRWS | SEQ ID NO: | 128 |
| ara h 1.115 | GEQEERGQRRWSTRS | SEQ ID NO: | 129 |
| ara h 1.116 | EERGQRRWSTRSSEN | SEQ ID NO: | 130 |
| ara h 1.129 | KKGSEEEGDITNPIN | SEQ ID NO: | 131 |
| ara h 1.130 | SEEEGDITNPINLRE | SEQ ID NO: | 132 |

| | | |
|---|---|---|
| ara h 1.131 | EGDITNPINLREGEP | SEQ ID NO: 133 |
| ara h 1.132 | ITNPINLREGEPDLS | SEQ ID NO: 134 |
| ara h 1.133 | PINLREGEPDLSNNF | SEQ ID NO: 135 |
| ara h 1.134 | LREGEPDLSNNFGKL | SEQ ID NO: 136 |
| ara h 1.135 | GEPDLSNNFGKLFEV | SEQ ID NO: 137 |
| ara h 1.136 | DLSNNFGKLFEVKPD | SEQ ID NO: 138 |
| ara h 1.137 | NNFGKLFEVKPDKKN | SEQ ID NO: 139 |
| ara h 1.138 | GKLFEVKPDKKNPQL | SEQ ID NO: 140 |
| ara h 1.141 | KKNPQLQDLDMMLTC | SEQ ID NO: 141 |
| ara h 1.142 | PQLQDLDMMLTCVEI | SEQ ID NO: 142 |
| ara h 1.143 | QDLDMMLTCVEIKEG | SEQ ID NO: 143 |
| ara h 1.144 | DMMLTCVEIKEGALM | SEQ ID NO: 144 |
| ara h 1.145 | LTCVEIKEGALMLPH | SEQ ID NO: 145 |
| ara h 1.146 | VEIKEGALMLPHFNS | SEQ ID NO: 146 |
| ara h 1.147 | KEGALMLPHFNSKAM | SEQ ID NO: 147 |
| ara h 1.165 | SNREVRRYTARLKEG | SEQ ID NO: 148 |
| ara h 1.166 | EVRRYTARLKEGDVF | SEQ ID NO: 149 |
| ara h 1.167 | RYTARLKEGDVFIMP | SEQ ID NO: 150 |
| ara h 1.168 | ARLKEGDVFIMPAAH | SEQ ID NO: 151 |
| ara h 1.169 | KEGDVFIMPAAHPVA | SEQ ID NO: 152 |
| ara h 1.170 | DVFIMPAAHPVAINA | SEQ ID NO: 153 |
| ara h 1.173 | PVAINASSELHLLGF | SEQ ID NO: 154 |
| ara h 1.174 | INASSELHLLGFGIN | SEQ ID NO: 155 |
| ara h 1.175 | SSELHLLGFGINAEN | SEQ ID NO: 156 |
| ara h 1.176 | LHLLGFGINAENNHR | SEQ ID NO: 157 |
| ara h 1.177 | LGFGINAENNHRIFL | SEQ ID NO: 158 |
| ara h 1.178 | GINAENNHRIFLAGD | SEQ ID NO: 159 |
| ara h 1.179 | AENNHRIFLAGDKDN | SEQ ID NO: 160 |
| ara h 1.180 | NHRIFLAGDKDNVID | SEQ ID NO: 161 |
| ara h 1.181 | IFLAGDKDNVIDQIE | SEQ ID NO: 162 |
| ara h 1.182 | AGDKDNVIDQIEKQA | SEQ ID NO: 163 |
| ara h 1.183 | KDNVIDQIEKQAKDL | SEQ ID NO: 164 |
| ara h 1.184 | VIDQIEKQAKDLAFP | SEQ ID NO: 165 |
| ara h 1.185 | QIEKQAKDLAFPGSG | SEQ ID NO: 166 |
| ara h 1.186 | KQAKDLAFPGSGEQV | SEQ ID NO: 167 |
| ara h 1.187 | KDLAFPGSGEQVEKL | SEQ ID NO: 168 |
| ara h 1.188 | AFPGSGEQVEKLIKN | SEQ ID NO: 169 |
| ara h 1.189 | GSGEQVEKLIKNQKE | SEQ ID NO: 170 |
| ara h 1.190 | EQVEKLIKNQKESHF | SEQ ID NO: 171 |
| ara h 1.191 | EKLIKNQKESHFVSA | SEQ ID NO: 172 |
| ara h 1.192 | IKNQKESHFVSARPQ | SEQ ID NO: 173 |
| ara h 1.193 | QKESHFVSARPQSQS | SEQ ID NO: 174 |
| ara h 1.194 | SHFVSARPQSQSQSP | SEQ ID NO: 175 |
| ara h 1.195 | VSARPQSQSQSPSSP | SEQ ID NO: 176 |
| ara h 1.196 | RPQSQSQSPSSPEKE | SEQ ID NO: 177 |
| ara h 1.197 | SQSQSPSSPEKESPE | SEQ ID NO: 178 |
| ara h 1.198 | QSPSSPEKESPEKED | SEQ ID NO: 179 |
| ara h 1.199 | SSPEKESPEKEDQEE | SEQ ID NO: 180 |
| ara h 1.200 | EKESPEKEDQEEENQ | SEQ ID NO: 181 |
| ara h 1.201 | SPEKEDQEEENQGGK | SEQ ID NO: 182 |
| ara h 1.202 | KEDQEEENQGGKGPL | SEQ ID NO: 183 |
| ara h 1.203 | QEEENQGGKGPLLSI | SEQ ID NO: 184 |
| ara h 2.005 | AAHASARQQWELQGD | SEQ ID NO: 185 |
| ara h 2.006 | ASARQQWELQGDRRC | SEQ ID NO: 186 |
| ara h 2.007 | RQQWELQGDRRCQSQ | SEQ ID NO: 187 |
| ara h 2.008 | WELQGDRRCQSQLER | SEQ ID NO: 188 |
| ara h 2.009 | QGDRRCQSQLERANL | SEQ ID NO: 189 |
| ara h 2.010 | RRCQSQLERANLRPC | SEQ ID NO: 190 |
| ara h 2.011 | QSQLERANLRPCEQH | SEQ ID NO: 191 |
| ara h 2.012 | LERANLRPCEQHLMQ | SEQ ID NO: 192 |
| ara h 2.013 | ANLRPCEQHLMQKIQ | SEQ ID NO: 193 |
| ara h 2.014 | RPCEQHLMQKIQRDE | SEQ ID NO: 194 |
| ara h 2.015 | EQHLMQKIQRDEDSY | SEQ ID NO: 195 |
| ara h 2.016 | LMQKIQRDEDSYERD | SEQ ID NO: 196 |
| ara h 2.017 | KIQRDEDSYERDPYS | SEQ ID NO: 197 |
| ara h 2.018 | RDEDSYERDPYSPSQ | SEQ ID NO: 198 |
| ara h 2.019 | DSYERDPYSPSQDPY | SEQ ID NO: 199 |
| ara h 2.020 | ERDPYSPSQDPYSPS | SEQ ID NO: 200 |
| ara h 2.021 | PYSPSQDPYSPSPYD | SEQ ID NO: 201 |
| ara h 2.022 | PSQDPYSPSPYDRRG | SEQ ID NO: 202 |
| ara h 2.023 | DPYSPSPYDRRGAGS | SEQ ID NO: 203 |
| ara h 2.024 | SPSPYDRRGAGSSQH | SEQ ID NO: 204 |
| ara h 2.025 | PYDRRGAGSSQHQER | SEQ ID NO: 205 |
| ara h 2.029 | QERCCNELNEFENNQ | SEQ ID NO: 206 |
| ara h 2.030 | CCNELNEFENNQRCM | SEQ ID NO: 207 |
| ara h 2.031 | ELNEFENNQRCMCEA | SEQ ID NO: 208 |
| ara h 2.032 | EFENNQRCMCEALQQ | SEQ ID NO: 209 |
| ara h 2.034 | RCMCEALQQIMENQS | SEQ ID NO: 210 |
| ara h 2.035 | CEALQQIMENQSDRL | SEQ ID NO: 211 |

| ara h 2.036 | LQQIMENQSDRLQGR | SEQ ID NO: 212 |
| ara h 2.037 | IMENQSDRLQGRQQE | SEQ ID NO: 213 |
| ara h 2.038 | NQSDRLQGRQQEQQF | SEQ ID NO: 214 |
| ara h 2.039 | DRLQGRQQEQQFKRE | SEQ ID NO: 215 |
| ara h 2.040 | QGRQQEQQFKRELRN | SEQ ID NO: 216 |
| ara h 2.041 | QQEQQFKRELRNLPQ | SEQ ID NO: 217 |
| ara h 2.042 | QQFKRELRNLPQQCG | SEQ ID NO: 218 |
| ara h 2.043 | KRELRNLPQQCGLRA | SEQ ID NO: 219 |
| ara h 2.045 | LPQQCGLRAPQRCDL | SEQ ID NO: 220 |
| ara h 2.046 | QCGLRAPQRCDLDVE | SEQ ID NO: 221 |
| ara h 2.047 | LRAPQRCDLDVESGG | SEQ ID NO: 222 |
| ara h 3.008 | RIESEGGYIETWNPN | SEQ ID NO: 223 |
| ara h 3.013 | NQEFECAGVALSRLV | SEQ ID NO: 224 |
| ara h 3.015 | AGVALSRLVLRRNAL | SEQ ID NO: 225 |
| ara h 3.016 | ALSRLVLRRNALRRP | SEQ ID NO: 226 |
| ara h 3.017 | RLVLRRNALRRPFYS | SEQ ID NO: 227 |
| ara h 3.018 | LRRNALRRPFYSNAP | SEQ ID NO: 228 |
| ara h 3.019 | NALRRPFYSNAPQEI | SEQ ID NO: 229 |
| ara h 3.030 | HYEEPHTQGRRSQSQ | SEQ ID NO: 230 |
| ara h 3.031 | EPHTQGRRSQSQRPP | SEQ ID NO: 231 |
| ara h 3.032 | TQGRRSQSQRPPRRL | SEQ ID NO: 232 |
| ara h 3.033 | RRSQSQRPPRRLQGE | SEQ ID NO: 233 |
| ara h 3.036 | RRLQGEDQSQQQRDS | SEQ ID NO: 234 |
| ara h 3.037 | QGEDQSQQQRDSHQK | SEQ ID NO: 235 |
| ara h 3.060 | NTEQEFLRYQQQSRQ | SEQ ID NO: 236 |
| ara h 3.061 | QEFLRYQQQSRQSRR | SEQ ID NO: 237 |
| ara h 3.068 | PYSPQSQPRQEEREF | SEQ ID NO: 238 |
| ara h 3.069 | PQSQPRQEEREFSPR | SEQ ID NO: 239 |
| ara h 3.070 | QPRQEEREFSPRGQH | SEQ ID NO: 240 |
| ara h 3.071 | QEEREFSPRGQHSRR | SEQ ID NO: 241 |
| ara h 3.073 | SPRGQHSRRERAGQE | SEQ ID NO: 242 |
| ara h 3.074 | GQHSRRERAGQEEEN | SEQ ID NO: 243 |
| ara h 3.075 | SRRERAGQEEENEGG | SEQ ID NO: 244 |
| ara h 3.077 | GQEEENEGGNIFSGF | SEQ ID NO: 245 |
| ara h 3.078 | EENEGGNIFSGFTPE | SEQ ID NO: 246 |
| ara h 3.079 | EGGNIFSGFTPEFLE | SEQ ID NO: 247 |
| ara h 3.080 | NIFSGFTPEFLEQAF | SEQ ID NO: 248 |
| ara h 3.081 | SGFTPEFLEQAFQVD | SEQ ID NO: 249 |
| ara h 3.082 | TPEFLEQAFQVDDRQ | SEQ ID NO: 250 |
| ara h 3.090 | ESEEEGAIVTVRGGL | SEQ ID NO: 251 |
| ara h 3.091 | EEGAIVTVRGGLRIL | SEQ ID NO: 252 |
| ara h 3.092 | AIVTVRGGLRILSPD | SEQ ID NO: 253 |
| ara h 3.093 | TVRGGLRILSPDRKR | SEQ ID NO: 254 |
| ara h 3.094 | GGLRILSPDRKRRAD | SEQ ID NO: 255 |
| ara h 3.095 | RILSPDRKRRADEEE | SEQ ID NO: 256 |
| ara h 3.097 | RKRRADEEEEYDEDE | SEQ ID NO: 257 |
| ara h 3.098 | RADEEEEYDEDEYEY | SEQ ID NO: 258 |
| ara h 3.099 | EEEEYDEDEYEYDEE | SEQ ID NO: 259 |
| ara h 3.100 | EYDEDEYEYDEEDRR | SEQ ID NO: 260 |
| ara h 3.101 | EDEYEYDEEDRRRGR | SEQ ID NO: 261 |
| ara h 3.102 | YEYDEEDRRRGRGSR | SEQ ID NO: 262 |
| ara h 3.103 | DEEDRRRGRGSRGRG | SEQ ID NO: 263 |
| ara h 3.104 | DRRRGRGSRGRGNGI | SEQ ID NO: 264 |
| ara h 3.105 | RGRGSRGRGNGIEET | SEQ ID NO: 265 |
| ara h 3.106 | GSRGRGNGIEETICT | SEQ ID NO: 266 |
| ara h 3.107 | GRGNGIEETICTASA | SEQ ID NO: 267 |
| ara h 3.108 | NGIEETICTASAKKN | SEQ ID NO: 268 |
| ara h 3.152 | IANLAGENSVIDNLP | SEQ ID NO: 269 |
| ara h 3.153 | LAGENSVIDNLPEEV | SEQ ID NO: 270 |
| ara h 3.154 | ENSVIDNLPEEVVAN | SEQ ID NO: 271 |
| ara h 3.155 | VIDNLPEEVVANSYG | SEQ ID NO: 272 |
| ara h 3.161 | EQARQLKNNNPFKFF | SEQ ID NO: 273 |
| ara h 3.162 | RQLKNNNPFKFFVPP | SEQ ID NO: 274 |
| ara h 3.163 | KNNNPFKFFVPPSQQ | SEQ ID NO: 275 |
| ara h 3.164 | NPFKFFVPPSQQSPR | SEQ ID NO: 276 |
| ara h 3.165 | KFFVPPSQQSPRAVA | SEQ ID NO: 277 |

In a further example, allergenic epitope-containing peptide panels derived from allergenic egg proteins, particularly ovalbumin (ova) and/or ovomucoid (ovm), may be utilized in methods similar to those discussed above. Such a panel may include one or more peptides from the following list (SEQ ID NOs:278-460):

| ova-1 | MGSIGAASMEFCFDV | SEQ ID NO: 278 |
| ova-2 | IGAASMEFCFDVFKE | SEQ ID NO: 279 |
| ova-3 | ASMEFCFDVFKELKV | SEQ ID NO: 280 |
| ova-4 | EFCFDVFKELKVHHA | SEQ ID NO: 281 |
| ova-5 | FDVFKELKVHHANEN | SEQ ID NO: 282 |
| ova-6 | FKELKVHHANENIFY | SEQ ID NO: 283 |
| ova-7 | LKVHHANENIFYCPI | SEQ ID NO: 284 |
| ova-8 | HHANENIFYCPIAIM | SEQ ID NO: 285 |

| | | |
|---|---|---|
| ova-9 | NENIFYCPIAIMSAL | SEQ ID NO: 286 |
| ova-10 | IFYCPIAIMSALAMV | SEQ ID NO: 287 |
| ova-11 | CPIAIMSALAMVYLG | SEQ ID NO: 288 |
| ova-12 | AIMSALAMVYLGAKD | SEQ ID NO: 289 |
| ova-13 | SALAMVYLGAKDSTR | SEQ ID NO: 290 |
| ova-14 | AMVYLGAKDSTRTQI | SEQ ID NO: 291 |
| ova-15 | YLGAKDSTRTQINKV | SEQ ID NO: 292 |
| ova-16 | AKDSTRTQINKVVRF | SEQ ID NO: 293 |
| ova-17 | STRTQINKVVRFDKL | SEQ ID NO: 294 |
| ova-18 | TQINKVVRFDKLPGF | SEQ ID NO: 295 |
| ova-19 | NKVVRFDKLPGFGDS | SEQ ID NO: 296 |
| ova-20 | VRFDKLPGFGDSIEA | SEQ ID NO: 297 |
| ova-21 | DKLPGFGDSIEAQCG | SEQ ID NO: 298 |
| ova-22 | PGFGDSIEAQCGTSV | SEQ ID NO: 299 |
| ova-23 | GDSIEAQCGTSVNVH | SEQ ID NO: 300 |
| ova-24 | IEAQCGTSVNVHSSL | SEQ ID NO: 301 |
| ova-25 | QCGTSVNVHSSLRDI | SEQ ID NO: 302 |
| ova-26 | TSVNVHSSLRDILNQ | SEQ ID NO: 303 |
| ova-27 | NVHSSLRDILNQITK | SEQ ID NO: 304 |
| ova-28 | SSLRDILNQITKPND | SEQ ID NO: 305 |
| ova-29 | RDILNQITKPNDVYS | SEQ ID NO: 306 |
| ova-30 | LNQITKPNDVYSFSL | SEQ ID NO: 307 |
| ova-31 | ITKPNDVYSFSLASR | SEQ ID NO: 308 |
| ova-32 | PNDVYSFSLASRLYA | SEQ ID NO: 309 |
| ova-33 | VYSFSLASRLYAEER | SEQ ID NO: 310 |
| ova-34 | FSLASRLYAEERYPI | SEQ ID NO: 311 |
| ova-35 | ASRLYAEERYPILPE | SEQ ID NO: 312 |
| ova-36 | LYAEERYPILPEYLQ | SEQ ID NO: 313 |
| ova-37 | EERYPILPEYLQCVK | SEQ ID NO: 314 |
| ova-38 | YPILPEYLQCVKELY | SEQ ID NO: 315 |
| ova-39 | LPEYLQCVKELYRGG | SEQ ID NO: 316 |
| ova-40 | YLQCVKELYRGGLEP | SEQ ID NO: 317 |
| ova-41 | CVKELYRGGLEPINF | SEQ ID NO: 318 |
| ova-42 | ELYRGGLEPINFQTA | SEQ ID NO: 319 |
| ova-43 | RGGLEPINFQTAADQ | SEQ ID NO: 320 |
| ova-44 | LEPINFQTAADQARE | SEQ ID NO: 321 |
| ova-45 | INFQTAADQARELIN | SEQ ID NO: 322 |
| ova-46 | QTAADQARELINSWV | SEQ ID NO: 323 |
| ova-47 | ADQARELINSWVESQ | SEQ ID NO: 324 |
| ova-48 | ARELINSWVESQTNG | SEQ ID NO: 325 |
| ova-49 | LINSWVESQTNGIIR | SEQ ID NO: 326 |
| ova-50 | SWVESQTNGIIRNVL | SEQ ID NO: 327 |
| ova-51 | ESQTNGIIRNVLQPS | SEQ ID NO: 328 |
| ova-52 | TNGIIRNVLQPSSVD | SEQ ID NO: 329 |
| ova-53 | IIRNVLQPSSVDSQT | SEQ ID NO: 330 |
| ova-54 | NVLQPSSVDSQTAMV | SEQ ID NO: 331 |
| ova-55 | QPSSVDSQTAMVLVN | SEQ ID NO: 332 |
| ova-56 | SVDSQTAMVLVNAIV | SEQ ID NO: 333 |
| ova-57 | SQTAMVLVNAIVFKG | SEQ ID NO: 334 |
| ova-58 | AMVLVNAIVFKGLWE | SEQ ID NO: 335 |
| ova-59 | LVNAIVFKGLWEKAF | SEQ ID NO: 336 |
| ova-60 | AIVFKGLWEKAFKDE | SEQ ID NO: 337 |
| ova-61 | FKGLWEKAFKDEDTQ | SEQ ID NO: 338 |
| ova-62 | LWEKAFKDEDTQAMP | SEQ ID NO: 339 |
| ova-63 | KAFKDEDTQAMPFRV | SEQ ID NO: 340 |
| ova-64 | KDEDTQAMPFRVTEQ | SEQ ID NO: 341 |
| ova-65 | DTQAMPFRVTEQESK | SEQ ID NO: 342 |
| ova-66 | AMPFRVTEQESKPVQ | SEQ ID NO: 343 |
| ova-67 | FRVTEQESKPVQMMY | SEQ ID NO: 344 |
| ova-68 | TEQESKPVQMMYQIG | SEQ ID NO: 345 |
| ova-69 | ESKPVQMMYQIGLFR | SEQ ID NO: 346 |
| ova-70 | PVQMMYQIGLFRVAS | SEQ ID NO: 347 |
| ova-71 | MMYQIGLFRVASMAS | SEQ ID NO: 348 |
| ova-72 | QIGLFRVASMASEKM | SEQ ID NO: 349 |
| ova-73 | LFRVASMASEKMKIL | SEQ ID NO: 350 |
| ova-74 | VASMASEKMKILELP | SEQ ID NO: 351 |
| ova-75 | MASEKMKILELPFAS | SEQ ID NO: 352 |
| ova-76 | EKMKILELPFASGTM | SEQ ID NO: 353 |
| ova-77 | KILELPFASGTMSML | SEQ ID NO: 354 |
| ova-78 | ELPFASGTMSMLVLL | SEQ ID NO: 355 |
| ova-79 | FASGTMSMLVLLPDE | SEQ ID NO: 356 |
| ova-80 | GTMSMLVLLPDEVSG | SEQ ID NO: 357 |
| ova-81 | SMLVLLPDEVSGLEQ | SEQ ID NO: 358 |
| ova-82 | VLLPDEVSGLEQLES | SEQ ID NO: 359 |
| ova-83 | PDEVSGLEQLESIIN | SEQ ID NO: 360 |
| ova-84 | VSGLEQLESIINFEK | SEQ ID NO: 361 |
| ova-85 | LEQLESIINFEKLTE | SEQ ID NO: 362 |
| ova-86 | LESIINFEKLTEWTS | SEQ ID NO: 363 |
| ova-87 | IINFEKLTEWTSSNV | SEQ ID NO: 364 |

| | | |
|---|---|---|
| ova-88 | FEKLTEWTSSNVMEE | SEQ ID NO: 365 |
| ova-89 | LTEWTSSNVMEERKI | SEQ ID NO: 366 |
| ova-90 | WTSSNVMEERKIKVY | SEQ ID NO: 367 |
| ova-91 | SNVMEERKIKVYLPR | SEQ ID NO: 368 |
| ova-92 | MEERKIKVYLPRMKM | SEQ ID NO: 369 |
| ova-93 | RKIKVYLPRMKMEEK | SEQ ID NO: 370 |
| ova-94 | KVYLPRMKMEEKYNL | SEQ ID NO: 371 |
| ova-95 | LPRMKMEEKYNLTSV | SEQ ID NO: 372 |
| ova-96 | MKMEEKYNLTSVLMA | SEQ ID NO: 373 |
| ova-97 | EEKYNLTSVLMAMGI | SEQ ID NO: 374 |
| ova-98 | YNLTSVLMAMGITDV | SEQ ID NO: 375 |
| ova-99 | TSVLMAMGITDVFSS | SEQ ID NO: 376 |
| ova-100 | LMAMGITDVFSSSAN | SEQ ID NO: 377 |
| ova-101 | MGITDVFSSSANLSG | SEQ ID NO: 378 |
| ova-102 | TDVFSSSANLSGISS | SEQ ID NO: 379 |
| ova-103 | FSSSANLSGISSAES | SEQ ID NO: 380 |
| ova-104 | SANLSGISSAESLKI | SEQ ID NO: 381 |
| ova-105 | LSGISSAESLKISQA | SEQ ID NO: 382 |
| ova-106 | ISSAESLKISQAVHA | SEQ ID NO: 383 |
| ova-107 | AESLKISQAVHAAHA | SEQ ID NO: 384 |
| ova-108 | LKISQAVHAAHAEIN | SEQ ID NO: 385 |
| ova-109 | SQAVHAAHAEINEAG | SEQ ID NO: 386 |
| ova-110 | VHAAHAEINEAGREV | SEQ ID NO: 387 |
| ova-111 | AHAEINEAGREVVGS | SEQ ID NO: 388 |
| ova-112 | EINEAGREVVGSAEA | SEQ ID NO: 389 |
| ova-113 | EAGREVVGSAEAGVD | SEQ ID NO: 390 |
| ova-114 | REVVGSAEAGVDAAS | SEQ ID NO: 391 |
| ova-115 | VGSAEAGVDAASVSE | SEQ ID NO: 392 |
| ova-116 | AEAGVDAASVSEEFR | SEQ ID NO: 393 |
| ova-117 | GVDAASVSEEFRADH | SEQ ID NO: 394 |
| ova-118 | AASVSEEFRADHPFL | SEQ ID NO: 395 |
| ova-119 | VSEEFRADHPFLFCI | SEQ ID NO: 396 |
| ova-120 | EFRADHPFLFCIKHI | SEQ ID NO: 397 |
| ova-121 | ADHPFLFCIKHIATN | SEQ ID NO: 398 |
| ova-122 | PFLFCIKHIATNAVL | SEQ ID NO: 399 |
| ova-123 | FCIKHIATNAVLFFG | SEQ ID NO: 400 |
| ova-124 | KHIATNAVLFFGRCV | SEQ ID NO: 401 |
| ova-125 | ATNAVLFFGRCVSP | SEQ ID NO: 402 |
| ovm-1 | AEVDCSRFPNATDKE | SEQ ID NO: 403 |
| ovm-2 | DCSRFPNATDKEGKD | SEQ ID NO: 404 |
| ovm-3 | RFPNATDKEGKDVLV | SEQ ID NO: 405 |
| ovm-4 | NATDKEGKDVLVCNK | SEQ ID NO: 406 |
| ovm-5 | DKEGKDVLVCNKDLR | SEQ ID NO: 407 |
| ovm-6 | GKDVLVCNKDLRPIC | SEQ ID NO: 408 |
| ovm-7 | VLVCNKDLRPICGTD | SEQ ID NO: 409 |
| ovm-8 | CNKDLRPICGTDGVT | SEQ ID NO: 410 |
| ovm-9 | DLRPICGTDGVTYTN | SEQ ID NO: 411 |
| ovm-10 | PICGTDGVTYTNDCL | SEQ ID NO: 412 |
| ovm-11 | GTDGVTYTNDCLLCA | SEQ ID NO: 413 |
| ovm-12 | GVTYTNDCLLCAYSI | SEQ ID NO: 414 |
| ovm-13 | YTNDCLLCAYSIEFG | SEQ ID NO: 415 |
| ovm-14 | DCLLCAYSIEFGTNI | SEQ ID NO: 416 |
| ovm-15 | LCAYSIEFGTNISKE | SEQ ID NO: 417 |
| ovm-16 | YSIEFGTNISKEHDG | SEQ ID NO: 418 |
| ovm-17 | EFGTNISKEHDGECK | SEQ ID NO: 419 |
| ovm-18 | TNISKEHDGECKETV | SEQ ID NO: 420 |
| ovm-19 | SKEHDGECKETVPMN | SEQ ID NO: 421 |
| ovm-20 | HDGECKETVPMNCSS | SEQ ID NO: 422 |
| ovm-21 | ECKETVPMNCSSYAN | SEQ ID NO: 423 |
| ovm-22 | ETVPMNCSSYANTTS | SEQ ID NO: 424 |
| ovm-23 | PMNCSSYANTTSEDG | SEQ ID NO: 425 |
| ovm-24 | CSSYANTTSEDGKVM | SEQ ID NO: 426 |
| ovm-25 | YANTTSEDGKVMVLC | SEQ ID NO: 427 |
| ovm-26 | TTSEDGKVMVLCNRA | SEQ ID NO: 428 |
| ovm-27 | EDGKVMVLCNRAFNP | SEQ ID NO: 429 |
| ovm-28 | KVMVLCNRAFNPVCG | SEQ ID NO: 430 |
| ovm-29 | VLCNRAFNPVCGTDG | SEQ ID NO: 431 |
| ovm-30 | NRAFNPVCGTDGVTY | SEQ ID NO: 432 |
| ovm-31 | FNPVCGTDGVTYDNE | SEQ ID NO: 433 |
| ovm-32 | VCGTDGVTYDNECLL | SEQ ID NO: 434 |
| ovm-33 | TDGVTYDNECLLCAH | SEQ ID NO: 435 |
| ovm-34 | VTYDNECLLCAHKVE | SEQ ID NO: 436 |
| ovm-35 | DNECLLCAHKVEQGA | SEQ ID NO: 437 |
| ovm-36 | CLLCAHKVEQGASVD | SEQ ID NO: 438 |
| ovm-37 | CAHKVEQGASVDKRH | SEQ ID NO: 439 |
| ovm-38 | KVEQGASVDKRHDGG | SEQ ID NO: 440 |
| ovm-39 | QGASVDKRHDGGCRK | SEQ ID NO: 441 |
| ovm-40 | SVDKRHDGGCRKELA | SEQ ID NO: 442 |
| ovm-41 | KRHDGGCRKELAAVS | SEQ ID NO: 443 |

-continued

| | | |
|---|---|---|
| ovm-42 | DGGCRKELAAVSVDC | SEQ ID NO: 444 |
| ovm-43 | CRKELAAVSVDCSEY | SEQ ID NO: 445 |
| ovm-44 | ELAAVSVDCSEYPKP | SEQ ID NO: 446 |
| ovm-45 | AVSVDCSEYPKPDCT | SEQ ID NO: 447 |
| ovm-46 | VDCSEYPKPDCTAED | SEQ ID NO: 448 |
| ovm-47 | SEYPKPDCTAEDRPL | SEQ ID NO: 449 |
| ovm-48 | PKPDCTAEDRPLCGS | SEQ ID NO: 450 |
| ovm-49 | DCTAEDRPLCGSDNK | SEQ ID NO: 451 |
| ovm-50 | AEDRPLCGSDNKTYG | SEQ ID NO: 452 |
| ovm-51 | RPLCGSDNKTYGNKC | SEQ ID NO: 453 |
| ovm-52 | CGSDNKTYGNKCNFC | SEQ ID NO: 454 |
| ovm-53 | DNKTYGNKCNFCNAV | SEQ ID NO: 455 |
| ovm-54 | TYGNKCNFCNAVVES | SEQ ID NO: 456 |
| ovm-55 | NKCNFCNAVVESNGT | SEQ ID NO: 457 |
| ovm-56 | NFCNAVVESNGTLTL | SEQ ID NO: 458 |
| ovm-57 | NAVVESNGTLTLSHF | SEQ ID NO: 459 |
| ovm-58 | VESNGTLTLSHFGKC | SEQ ID NO: 460 |

In a further example, allergenic epitope-containing peptide panels derived from allergenic shrimp proteins, particularly arginine kinase (ak), myosin light chain (mlc), sarcoplasmic calcium binding protein (scp), tropomyosin (tm) and Troponin C (tpc), may be utilized in methods similar to those discussed above. Such a panel may include one or more peptides from the following list SEQ ID NOs:461-683):

| | | |
|---|---|---|
| ak-01 | H-MADAAVIEKLEAGFK-OH | SEQ ID NO: 461 |
| ak-02 | H-VIEKLEAGFKKLEAA-OH | SEQ ID NO: 462 |
| ak-03 | H-EAGFKKLEAATDCKS-OH | SEQ ID NO: 463 |
| ak-04 | H-KLEAATDCKSLLKKY-OH | SEQ ID NO: 464 |
| ak-05 | H-TDCKSLLKKYLTKEV-OH | SEQ ID NO: 465 |
| ak-06 | H-LLKKYLTKEVFDKLK-OH | SEQ ID NO: 466 |
| ak-07 | H-LTKEVFDKLKDKKTS-OH | SEQ ID NO: 467 |
| ak-08 | H-FDKLKDKKTSLGATL-OH | SEQ ID NO: 468 |
| ak-09 | H-DKKTSLGATLLDVIQ-OH | SEQ ID NO: 469 |
| ak-10 | H-LGATLLDVIQSGVEN-OH | SEQ ID NO: 470 |
| ak-11 | H-LDVIQSGVENLDSGV-OH | SEQ ID NO: 471 |
| ak-12 | H-SGVENLDSGVGIYAP-OH | SEQ ID NO: 472 |
| ak-13 | H-LDSGVGIYAPDAEAY-OH | SEQ ID NO: 473 |
| ak-14 | H-GIYAPDAEAYTLFAP-OH | SEQ ID NO: 474 |
| ak-15 | H-DAEAYTLFAPLFDPI-OH | SEQ ID NO: 475 |
| ak-16 | H-TLFAPLFDPIIEDYH-OH | SEQ ID NO: 476 |
| ak-17 | H-LFDPIIEDYHVGFKQ-OH | SEQ ID NO: 477 |
| ak-18 | H-IEDYHVGFKQTDKHP-OH | SEQ ID NO: 478 |
| ak-19 | H-VGFKQTDKHPNKDFG-OH | SEQ ID NO: 479 |
| ak-20 | H-TDKHPNKDFGDVNSF-OH | SEQ ID NO: 480 |
| ak-21 | H-NKDFGDVNSFVNVDP-OH | SEQ ID NO: 481 |
| ak-22 | H-DVNSFVNVDPEGKFV-OH | SEQ ID NO: 482 |
| ak-23 | H-VNVDPEGKFVISTRV-OH | SEQ ID NO: 483 |
| ak-24 | H-EGKFVISTRVRCGRS-OH | SEQ ID NO: 484 |
| ak-25 | H-ISTRVRCGRSMQGYP-OH | SEQ ID NO: 485 |
| ak-26 | H-RCGRSMQGYPFNPCL-OH | SEQ ID NO: 486 |
| ak-27 | H-MQGYPFNPCLTESQY-OH | SEQ ID NO: 487 |
| ak-28 | H-FNPCLTESQYKEMEA-OH | SEQ ID NO: 488 |
| ak-29 | H-TESQYKEMEAKVSST-OH | SEQ ID NO: 489 |
| ak-30 | H-KEMEAKVSSTLSSLE-OH | SEQ ID NO: 490 |
| ak-31 | H-KVSSTLSSLEGELKG-OH | SEQ ID NO: 491 |
| ak-32 | H-LSSLEGELKGTYYPL-OH | SEQ ID NO: 492 |
| ak-33 | H-GELKGTYYPLTGMSK-OH | SEQ ID NO: 493 |
| ak-34 | H-TYYPLTGMSKEVQQK-OH | SEQ ID NO: 494 |
| ak-35 | H-TGMSKEVQQKLIDDH-OH | SEQ ID NO: 495 |
| ak-36 | H-EVQQKLIDDHFLFKE-OH | SEQ ID NO: 496 |
| ak-37 | H-LIDDHFLFKEGDRFL-OH | SEQ ID NO: 497 |
| ak-38 | H-FLFKEGDRFLQAANA-OH | SEQ ID NO: 498 |
| ak-39 | H-GDRFLQAANACRYWP-OH | SEQ ID NO: 499 |
| ak-40 | H-QAANACRYWPAGRGI-OH | SEQ ID NO: 500 |
| ak-41 | H-CRYWPAGRGIYHNDN-OH | SEQ ID NO: 501 |
| ak-42 | H-AGRGIYHNDNKTFLV-OH | SEQ ID NO: 502 |
| ak-43 | H-YHNDNKTFLVWVNEE-OH | SEQ ID NO: 503 |
| ak-44 | H-KTFLVWVNEEDHLRI-OH | SEQ ID NO: 504 |
| ak-45 | H-WVNEEDHLRIISMQM-OH | SEQ ID NO: 505 |
| ak-46 | H-DHLRIISMQMGGDLG-OH | SEQ ID NO: 506 |
| ak-47 | H-ISMQMGGDLGQVFRR-OH | SEQ ID NO: 507 |
| ak-48 | H-GGDLGQVFRRLTSAV-OH | SEQ ID NO: 508 |
| ak-49 | H-QVFRRLTSAVNEIEK-OH | SEQ ID NO: 509 |
| ak-50 | H-LTSAVNEIEKRIPFS-OH | SEQ ID NO: 510 |
| ak-51 | H-NEIEKRIPFSHHDRL-OH | SEQ ID NO: 511 |
| ak-52 | H-RIPFSHHDRLGFLTF-OH | SEQ ID NO: 512 |
| ak-53 | H-HHDRLGFLTFCPTNL-OH | SEQ ID NO: 513 |
| ak-54 | H-GFLTFCPTNLGTTVR-OH | SEQ ID NO: 514 |
| ak-55 | H-CPTNLGTTVRASVHI-OH | SEQ ID NO: 515 |
| ak-56 | H-GTTVRASVHIKLPKL-OH | SEQ ID NO: 516 |

| | | |
|---|---|---|
| ak-57 | H-ASVHIKLPKLAANRE-OH | SEQ ID NO: 517 |
| ak-58 | H-KLPKLAANREKLEEV-OH | SEQ ID NO: 518 |
| ak-59 | H-AANREKLEEVAGKYN-OH | SEQ ID NO: 519 |
| ak-60 | H-KLEEVAGKYNLQVRG-OH | SEQ ID NO: 520 |
| ak-61 | H-AGKYNLQVRGTRGEH-OH | SEQ ID NO: 521 |
| ak-62 | H-LQVRGTRGEHTEAEG-OH | SEQ ID NO: 522 |
| ak-63 | H-TRGEHTEAEGGIYDI-OH | SEQ ID NO: 523 |
| ak-64 | H-TEAEGGIYDISNKRR-OH | SEQ ID NO: 524 |
| ak-65 | H-GIYDISNKRRMGLTE-OH | SEQ ID NO: 525 |
| ak-66 | H-SNKRRMGLTEFQAVK-OH | SEQ ID NO: 526 |
| ak-67 | H-MGLTEFQAVKEMQDG-OH | SEQ ID NO: 527 |
| ak-68 | H-FQAVKEMQDGILELI-OH | SEQ ID NO: 528 |
| ak-69 | H-EMQDGILELIKIEKE-OH | SEQ ID NO: 529 |
| mlc-01 | H-MSRKSGSRSSSKRSK-OH | SEQ ID NO: 530 |
| mlc-02 | H-GSRSSSKRSKKSGGG-OH | SEQ ID NO: 531 |
| mlc-03 | H-SKRSKKSGGGSNVFD-OH | SEQ ID NO: 532 |
| mlc-04 | H-KSGGGSNVFDMFTQR-OH | SEQ ID NO: 533 |
| mlc-05 | H-SNVFDMFTQRVAEF-OH | SEQ ID NO: 534 |
| mlc-06 | H-MFTQRVAEFKEGFQ-OH | SEQ ID NO: 535 |
| mlc-07 | H-QVAEFKEGFQLMDRD-OH | SEQ ID NO: 536 |
| mlc-08 | H-KEGFQLMDRDKDGVI-OH | SEQ ID NO: 537 |
| mlc-09 | H-LMDRDKDGVIGKTDL-OH | SEQ ID NO: 538 |
| mlc-10 | H-KDGVIGKTDLRGTFD-OH | SEQ ID NO: 539 |
| mlc-11 | H-GKTDLRGTFDEIGRI-OH | SEQ ID NO: 540 |
| mlc-12 | H-RGTFDEIGRIATDQE-OH | SEQ ID NO: 541 |
| mlc-13 | H-EIGRIATDQELDEML-OH | SEQ ID NO: 542 |
| mlc-14 | H-ATDQELDEMLADAPA-OH | SEQ ID NO: 543 |
| mlc-15 | H-LDEMLADAPAPINFT-OH | SEQ ID NO: 544 |
| mlc-16 | H-ADAPAPINFTMLLNM-OH | SEQ ID NO: 545 |
| mlc-17 | H-PINFTMLLNMFAERQ-OH | SEQ ID NO: 546 |
| mlc-18 | H-MLLNMFAERQTGESD-OH | SEQ ID NO: 547 |
| mlc-19 | H-FAERQTGESDDDDVV-OH | SEQ ID NO: 548 |
| mlc-20 | H-TGESDDDDVVAKAFL-OH | SEQ ID NO: 549 |
| mlc-21 | H-DDDVVAKAFLAFADE-OH | SEQ ID NO: 550 |
| mlc-22 | H-AKAFLAFADEEGNID-OH | SEQ ID NO: 551 |
| mlc-23 | H-AFADEEGNIDCDTFR-OH | SEQ ID NO: 552 |
| mlc-24 | H-EGNIDCDTFRHALMT-OH | SEQ ID NO: 553 |
| mlc-25 | H-CDTFRHALMTWGDKF-OH | SEQ ID NO: 554 |
| mlc-26 | H-HALMTWGDKFSSQEA-OH | SEQ ID NO: 555 |
| mlc-27 | H-WGDKFSSQEADDALD-OH | SEQ ID NO: 556 |
| mlc-28 | H-SSQEADDALDQMDID-OH | SEQ ID NO: 557 |
| mlc-29 | H-DDALDQMDIDDGGKI-OH | SEQ ID NO: 558 |
| mlc-30 | H-QMDIDDGGKIDVQGV-OH | SEQ ID NO: 559 |
| mlc-31 | H-DGGKIDVQGVIQMLT-OH | SEQ ID NO: 560 |
| mlc-32 | H-DVQGVIQMLTAGGGD-OH | SEQ ID NO: 561 |
| mlc-33 | H-IQMLTAGGGDDAAAE-OH | SEQ ID NO: 562 |
| mlc-34 | H-AGGGDDAAAEEA-OH | SEQ ID NO: 563 |
| scp-01 | H-MAYSWDNRVKYVVRY-OH | SEQ ID NO: 564 |
| scp-02 | H-DNRVKYVVRYMYDID-OH | SEQ ID NO: 565 |
| scp-03 | H-YVVRYMYDIDNNGFL-OH | SEQ ID NO: 566 |
| scp-04 | H-MYDIDNNGFLDKNDF-OH | SEQ ID NO: 567 |
| scp-05 | H-NNGFLDKNDFECLAV-OH | SEQ ID NO: 568 |
| scp-06 | H-DKNDFECLAVRNTLI-OH | SEQ ID NO: 569 |
| scp-07 | H-ECLAVRNTLIEGRGE-OH | SEQ ID NO: 570 |
| scp-08 | H-RNTLIEGRGEFSADA-OH | SEQ ID NO: 571 |
| scp-09 | H-EGRGEFSADAYANNQ-OH | SEQ ID NO: 572 |
| scp-10 | H-FSADAYANNQKIMRN-OH | SEQ ID NO: 573 |
| scp-11 | H-YANNQKIMRNLWNEI-OH | SEQ ID NO: 574 |
| scp-12 | H-KIMRNLWNEIAELAD-OH | SEQ ID NO: 575 |
| scp-13 | H-LWNEIAELADFNKDG-OH | SEQ ID NO: 576 |
| scp-14 | H-AELADFNKDGEVTVD-OH | SEQ ID NO: 577 |
| scp-15 | H-FNKDGEVTVDEFKQA-OH | SEQ ID NO: 578 |
| scp-16 | H-EVTVDEFKQAVQKHC-OH | SEQ ID NO: 579 |
| scp-17 | H-EFKQAVQKHCQGKKY-OH | SEQ ID NO: 580 |
| scp-18 | H-VQKHCQGKKYGDFPG-OH | SEQ ID NO: 581 |
| scp-19 | H-QGKKYGDFPGAFKVF-OH | SEQ ID NO: 582 |
| scp-20 | H-GDFPGAFKVFIANQF-OH | SEQ ID NO: 583 |
| scp-21 | H-AFKVFIANQFKAIDV-OH | SEQ ID NO: 584 |
| scp-22 | H-IANQFKAIDVNGDGK-OH | SEQ ID NO: 585 |
| scp-23 | H-KAIDVNGDGKVGLDE-OH | SEQ ID NO: 586 |
| scp-24 | H-NGDGKVGLDEYRLDC-OH | SEQ ID NO: 587 |
| scp-25 | H-VGLDEYRLDCITRSA-OH | SEQ ID NO: 588 |
| scp-26 | H-YRLDCITRSAFAEVK-OH | SEQ ID NO: 589 |
| scp-27 | H-ITRSAFAEVKEIDDA-OH | SEQ ID NO: 590 |
| scp-28 | H-FAEVKEIDDAYNKLT-OH | SEQ ID NO: 591 |
| scp-29 | H-EIDDAYNKLTTEDDR-OH | SEQ ID NO: 592 |
| scp-30 | H-YNKLTTEDDRKAGGL-OH | SEQ ID NO: 593 |
| scp-31 | H-TEDDRKAGGLTLERY-OH | SEQ ID NO: 594 |
| scp-32 | H-KAGGLTLERYQDLYA-OH | SEQ ID NO: 595 |

-continued

| | | |
|---|---|---|
| scp-33 | H-TLERYQDLYAQFISN-OH | SEQ ID NO: 596 |
| scp-34 | H-QDLYAQFISNPDESC-OH | SEQ ID NO: 597 |
| scp-35 | H-QFISNPDESCSACYL-OH | SEQ ID NO: 598 |
| scp-36 | H-PDESCSACYLFGPLK-OH | SEQ ID NO: 599 |
| scp-37 | H-SACYLFGPLKVVQ-OH | SEQ ID NO: 600 |
| tm-01 | H-MDAIKKKMQAMKLEK-OH | SEQ ID NO: 601 |
| tm-02 | H-KKMQAMKLEKDNAMD-OH | SEQ ID NO: 602 |
| tm-03 | H-MKLEKDNAMDRADTL-OH | SEQ ID NO: 603 |
| tm-04 | H-DNAMDRADTLEQQNK-OH | SEQ ID NO: 604 |
| tm-05 | H-RADTLEQQNKEANNR-OH | SEQ ID NO: 605 |
| tm-06 | H-EQQNKEANNRAEKSE-OH | SEQ ID NO: 606 |
| tm-07 | H-EANNRAEKSEEEVHN-OH | SEQ ID NO: 607 |
| tm-08 | H-AEKSEEEVHNLQKRM-OH | SEQ ID NO: 608 |
| tm-09 | H-EEVHNLQKRMQQLEN-OH | SEQ ID NO: 609 |
| tm-10 | H-LQKRMQQLENDLDQV-OH | SEQ ID NO: 610 |
| tm-11 | H-QQLENDLDQVQESLL-OH | SEQ ID NO: 611 |
| tm-12 | H-DLDQVQESLLKANIQ-OH | SEQ ID NO: 612 |
| tm-13 | H-QESLLKANIQLVEKD-OH | SEQ ID NO: 613 |
| tm-14 | H-KANIQLVEKDKALSN-OH | SEQ ID NO: 614 |
| tm-15 | H-LVEKDKALSNAEGEV-OH | SEQ ID NO: 615 |
| tm-16 | H-KALSNAEGEVAALNR-OH | SEQ ID NO: 616 |
| tm-17 | H-AEGEVAALNRRIQLL-OH | SEQ ID NO: 617 |
| tm-18 | H-AALNRRIQLLEEDLE-OH | SEQ ID NO: 618 |
| tm-19 | H-RIQLLEEDLERSEER-OH | SEQ ID NO: 619 |
| tm-20 | H-EEDLERSEERLNTAT-OH | SEQ ID NO: 620 |
| tm-21 | H-RSEERLNTATTKLAE-OH | SEQ ID NO: 621 |
| tm-22 | H-LNTATTKLAEASQAA-OH | SEQ ID NO: 622 |
| tm-23 | H-TKLAEASQAADESER-OH | SEQ ID NO: 623 |
| tm-24 | H-ASQAADESERMRKVL-OH | SEQ ID NO: 624 |
| tm-25 | H-DESERMRKVLENRSL-OH | SEQ ID NO: 625 |
| tm-26 | H-MRKVLENRSLSDEER-OH | SEQ ID NO: 626 |
| tm-27 | H-ENRSLSDEERMDALE-OH | SEQ ID NO: 627 |
| tm-28 | H-SDEERMDALENQLKE-OH | SEQ ID NO: 628 |
| tm-29 | H-MDALENQLKEARFLA-OH | SEQ ID NO: 629 |
| tm-30 | H-NQLKEARFLAEEADR-OH | SEQ ID NO: 630 |
| tm-31 | H-ARFLAEEADRKYDEV-OH | SEQ ID NO: 631 |
| tm-32 | H-EEADRKYDEVARKLA-OH | SEQ ID NO: 632 |
| tm-33 | H-KYDEVARKLAMVEAD-OH | SEQ ID NO: 633 |
| tm-34 | H-ARKLAMVEADLERAE-OH | SEQ ID NO: 634 |
| tm-35 | H-MVEADLERAEERAET-OH | SEQ ID NO: 635 |
| tm-36 | H-LERAEERAETGESKI-OH | SEQ ID NO: 636 |
| tm-37 | H-ERAETGESKIVELEE-OH | SEQ ID NO: 637 |
| tm-38 | H-GESKIVELEEELRVV-OH | SEQ ID NO: 638 |
| tm-39 | H-VELEEELRVVGNNLK-OH | SEQ ID NO: 639 |
| tm-40 | H-ELRVVGNNLKSLEVS-OH | SEQ ID NO: 640 |
| tm-41 | H-GNNLKSLEVSEEKAN-OH | SEQ ID NO: 641 |
| tm-42 | H-SLEVSEEKANQREEA-OH | SEQ ID NO: 642 |
| tm-43 | H-EEKANQREEAYKEQI-OH | SEQ ID NO: 643 |
| tm-44 | H-QREEAYKEQIKTLTN-OH | SEQ ID NO: 644 |
| tm-45 | H-YKEQIKTLTNKLKAA-OH | SEQ ID NO: 645 |
| tm-46 | H-KTLTNKLKAAEARAE-OH | SEQ ID NO: 646 |
| tm-47 | H-KLKAAEARAEFAERS-OH | SEQ ID NO: 647 |
| tm-48 | H-EARAEFAERSVQKLQ-OH | SEQ ID NO: 648 |
| tm-49 | H-FAERSVQKLQKEVDR-OH | SEQ ID NO: 649 |
| tm-50 | H-VQKLQKEVDRLEDEL-OH | SEQ ID NO: 650 |
| tm-51 | H-KEVDRLEDELVNEKE-OH | SEQ ID NO: 651 |
| tm-52 | H-LEDELVNEKEKYKSI-OH | SEQ ID NO: 652 |
| tm-53 | H-VNEKEKYKSITDELD-OH | SEQ ID NO: 653 |
| tm-54 | H-KYKSITDELDQTFSE-OH | SEQ ID NO: 654 |
| tm-55 | H-TDELDQTFSELSGY-OH | SEQ ID NO: 655 |
| tpc-01 | H-MDSLDEEQIETLRKA-OH | SEQ ID NO: 656 |
| tpc-02 | H-EEQIETLRKAFDSFD-OH | SEQ ID NO: 657 |
| tpc-03 | H-TLRKAFDSFDTEKTG-OH | SEQ ID NO: 658 |
| tpc-04 | H-FDSFDTEKTGSITAE-OH | SEQ ID NO: 659 |
| tpc-05 | H-TEKTGSITAETIATI-OH | SEQ ID NO: 660 |
| tpc-06 | H-SITAETIATIMRMMG-OH | SEQ ID NO: 661 |
| tpc-07 | H-TIATIMRMMGVKISE-OH | SEQ ID NO: 662 |
| tpc-08 | H-MRMMGVKISEKNLQE-OH | SEQ ID NO: 663 |
| tpc-09 | H-VKISEKNLQEAIAET-OH | SEQ ID NO: 664 |
| tpc-10 | H-KNLQEAIAETDEDGS-OH | SEQ ID NO: 665 |
| tpc-11 | H-AIAETDEDGSGLLEF-OH | SEQ ID NO: 666 |
| tpc-12 | H-DEDGSGLLEFEEFVE-OH | SEQ ID NO: 667 |
| tpc-13 | H-GLLEFEEFVELSAKF-OH | SEQ ID NO: 668 |
| tpc-14 | H-EEFVELSAKFLIEED-OH | SEQ ID NO: 669 |
| tpc-15 | H-LSAKFLIEEDEEALK-OH | SEQ ID NO: 670 |
| tpc-16 | H-LIEEDEEALKAELRE-OH | SEQ ID NO: 671 |
| tpc-17 | H-EEALKAELREAFRIY-OH | SEQ ID NO: 672 |
| tpc-18 | H-AELREAFRIYDKEGN-OH | SEQ ID NO: 673 |
| tpc-19 | H-AFRIYDKEGNGFITT-OH | SEQ ID NO: 674 |

| | | |
|---|---|---|
| tpc-20 | H-DKEGNGFITTDVLKE-OH | SEQ ID NO: 675 |
| tpc-21 | H-GFITTDVLKEILAEL-OH | SEQ ID NO: 676 |
| tpc-22 | H-DVLKEILAELDPRLT-OH | SEQ ID NO: 677 |
| tpc-23 | H-ILAELDPRLTPADLE-OH | SEQ ID NO: 678 |
| tpc-24 | H-DPRLTPADLENIIEE-OH | SEQ ID NO: 679 |
| tpc-25 | H-PADLENIIEEVDEDG-OH | SEQ ID NO: 680 |
| tpc-26 | H-NIIEEVDEDGSGTLD-OH | SEQ ID NO: 681 |
| tpc-27 | H-VDEDGSGTLDFDEFM-OH | SEQ ID NO: 682 |
| tpc-28 | H-SGTLDFDEFMEMMNG-OH | SEQ ID NO: 683 |

Accordingly, the invention encompasses a method for diagnosing a food allergy in a subject comprising:

a) providing a plurality of peptides derived from one or more allergenic proteins found in the food, each peptide conjugated to a separately identifiable solid support;

b) contacting each solid support with serum obtained from the subject under conditions sufficient to permit binding of IgE in the serum to the peptide on each solid support to form a peptide-IgE complex;

c) binding an IgE-specific labeling reagent to the peptide-IgE complex; and d) analyzing binding of the labeling reagent to each peptide-IgE complex to identify peptides recognized by the IgE in the serum of the subject;

wherein recognition of at least one peptide by IgE in the serum of the subject indicates that the subject is allergic to the food.

In another aspect the invention provides a method for detecting development of clinical tolerance to a food in a subject initially allergic to the food comprising:

a) providing an initial profile of the subject's serum IgE reactivity to a plurality of peptides derived from one or more allergenic proteins found in the food, wherein the initial profile defines an initial number of peptides recognized by IgE in the serum of the subject or an initial concentration of IgE in the serum of the subject that recognizes each peptide;

b) providing the plurality of peptides each conjugated to a separately identifiable solid support;

c) contacting each solid support with serum obtained from the subject at a time-point subsequent to the initial profile under conditions sufficient to permit binding of IgE in the serum to the peptide on each solid support to form a peptide-IgE complex;

d) binding an IgE-specific labeling reagent to the peptide-IgE complex; and e) analyzing binding of the labeling reagent to each peptide-IgE complex to identify a subsequent number of peptides recognized by IgE in the serum of the subject or a subsequent concentration of IgE in the serum of the subject that recognizes each peptide;

wherein development of clinical tolerance to the food is indicated when the subsequent number of peptides recognized by IgE in the serum of the subject is less than the initial number of peptides recognized by IgE in the serum of the subject, or when the subsequent concentration of IgE in the serum of the subject that recognizes at least one peptide is less than the initial concentration of IgE in the serum of the subject that recognizes the at least one peptide.

In a further aspect, the invention provides a method for detecting an increase in intensity of allergy to cow's milk in a subject over time, the method comprising:

a) providing an initial profile of the subject's serum IgE reactivity to a plurality of peptides derived from one or more allergenic proteins found in the food, wherein the initial profile defines an initial number of peptides recognized by IgE in the serum of the subject or an initial concentration of IgE in the serum of the subject that recognizes each peptide;

b) providing the plurality of peptides each conjugated to a separately identifiable solid support c) contacting each solid support with serum obtained from the subject at a time-point subsequent to the initial profile under conditions sufficient to permit binding of IgE in the serum to the peptide on each solid support to form a peptide-IgE complex;

d) binding an IgE-specific labeling reagent to the peptide-IgE complex; and e) analyzing the binding of the labeling reagent to each peptide-IgE complex to identify a subsequent number of peptides recognized by IgE in the serum of the subject or a subsequent concentration of IgE in the serum of the subject that recognizes each peptide;

wherein an increase in the subsequent number of peptides recognized by IgE in the serum of the subject compared to the initial number of peptides recognized by IgE in the serum of the subject, or an increase in the subsequent concentration of IgE in the serum of the subject that recognizes at least one peptide compared to the initial concentration of IgE in the serum of the subject that recognizes the at least one peptide, indicates increased intensity in the subject of the allergic response to the food.

The reagents and materials used in any of the foregoing methods may be packaged in the form of a kit in which the plurality of allergenic epitope-containing peptides, a labeling reagent comprising an anti-IgE antibody conjugated to a first reporter moiety and, optionally, a second reporter moiety that specifically binds to the labeling reagent are packaged together.

It will also be understood that any of the peptide panels disclosed herein, and subsets thereof, that are useful in the methods of the invention are also an aspect of the invention.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A set of allergenic epitope-containing peptides for detection of milk allergy consisting of a plurality of peptides represented by SEQ ID NOs:1-33, wherein the plurality of peptides consists of all 33 peptides of SEQ ID NOs:1-33, a subset of 20-25 peptides, a subset of 15-20 peptides, or a subset of 10-15 peptides, and wherein each peptide is conjugated to a solid support.

2. The set of allergenic epitope-containing peptides of claim 1, wherein the solid support is a bead, a microtiter plate, or a chromatographic material.

3. The set of allergenic epitope-containing peptides of claim 1, wherein each peptide is conjugated to a separately identifiable solid support.

4. The set of allergenic epitope-containing peptides of claim 1, wherein the plurality of peptides consists of all 33 peptides of SEQ ID NOs:1-33.

5. The set of allergenic epitope-containing peptides of claim 1, wherein the plurality of peptides consists of the subset of 20-25 peptides.

6. The set of allergenic epitope-containing peptides of claim 1, wherein the plurality of peptides consists of the subset of 15-20.

7. The set of allergenic epitope-containing peptides of claim 1, wherein the plurality of peptides consists of the subset of 10-15 peptides.

* * * * *